United States Patent [19]

Asai et al.

[11] 4,361,650
[45] Nov. 30, 1982

[54] FERMENTATION PROCESS OF PREPARING DEMETHYL MAYTANSINOIDS

[75] Inventors: Mitsuko Asai, Osaka; Kazuo Nakahama, Kyoto; Motowo Izawa, Hyogo, all of Japan

[73] Assignee: Takeda Chemical Industries, Ltd., Osaka, Japan

[21] Appl. No.: 290,943

[22] Filed: Aug. 7, 1981

Related U.S. Application Data

[60] Division of Ser. No. 153,522, May 27, 1980, Pat. No. 4,307,016, which is a continuation-in-part of Ser. No. 19,612, Mar. 12, 1979, abandoned.

[30] Foreign Application Priority Data

Mar. 24, 1978 [JP] Japan ................... 53/34645
Dec. 22, 1978 [JP] Japan ................... 53/160787
Sep. 17, 1979 [JP] Japan ................... 54/119959
Mar. 12, 1979 [KR] Rep. of Korea ........... 2968(1979)[U]

[51] Int. Cl.³ .............................................. C12P 17/18
[52] U.S. Cl. .................................................. 435/119
[58] Field of Search ...................................... 435/119

[56] References Cited

U.S. PATENT DOCUMENTS 4,151,042  4/1979  Higashide et al. ................ 435/119
4,225,494  9/1980  Higashide et al. ................ 435/119
4,322,348  3/1982  Asai et al. ........................ 435/119

*Primary Examiner*—Alvin E. Tanenholtz
*Attorney, Agent, or Firm*—Wegner & Bretschneider

[57] ABSTRACT

Novel demethylmaytansinoids representable by the formula:

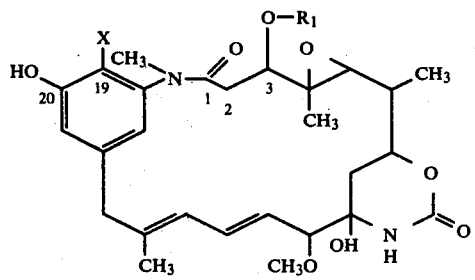

(wherein X is Cl or H; $R_1$ is H or acyl group) are produced from maytansinoids by means of enzymic transformation. The demethylmaytansinoids are useful as antifungal, antiprotozoal or antitumor agents.

8 Claims, No Drawings

FERMENTATION PROCESS OF PREPARING DEMETHYL MAYTANSINOIDS

This application is a divisional of application Ser. No. 153,522 filed May 27, 1980, now U.S. Pat. No. 4,307,016, which is a continuation-in-part of Ser. No. 19,612 filed Mar. 12, 1979, now abandoned.

This invention is directed to: (1) a demethylmaytansinoid compound of the formula (I):

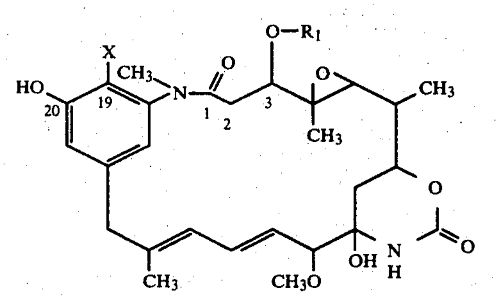

(I)

(wherein X is Cl or H; $R_1$ is H or acyl group); (2) a method for producing a demethylmaytansinoid compound of the formula (III):

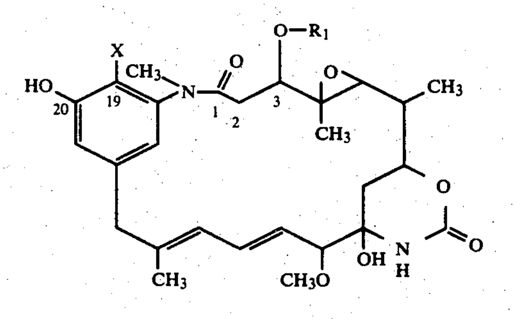

(III)

(wherein X is Cl or H; $R_1$ is H or acyl group) characterized in that a maytansinoid compound of the formula (II):

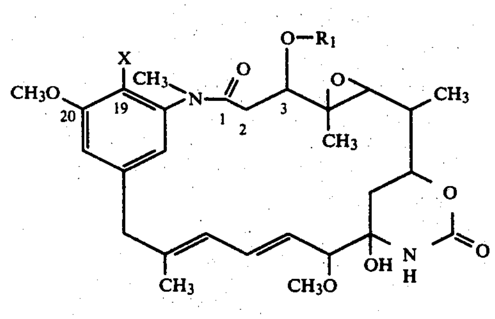

(II)

(wherein X and $R_1$ are as respectively defined above) is contacted with a culture broth, inclusive of a processed matter of the culture broth, of a microorganism belonging to the genus Bacillus, the genus Streptomyces or the genus Actinomyces which is able to transform the 20-methoxy group of said compound (II) into a hydroxy group; and (3) a method for producing a demethylmaytansinoid compound of the formula (VI):

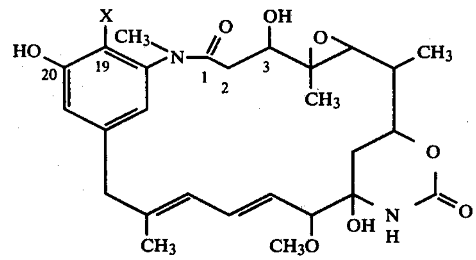

(VI)

(wherein X is Cl or H) characterized in that a maytansinoid compound (IV) which corresponds to compound (II) wherein $R_1$ is an acyl group $R'_1$ is contacted with a culture broth, inclusive of a processed matter of the culture broth, of a microorganism belonging to the genus Bacillus, the genus Streptomyces or the genus Actinomyces which is able to transform the 20-methoxy group of compound (IV) into a hydroxy group to obtain a compound (V) which corresponds to compound (III) wherein $R_1$ is an acyl group $R'_1$ and this latter compound (V) is then deacylated.

The compounds (I) are useful as antifungal, antiprotozoal and antitumor agents. That such compounds are useful as antifungal and antiprotozoal agents has been established through testing the nineteen representatives of the compounds of the formula (I) with *Hamigera avellanea* IFO 7721 and *Tetrahymena pyriformis W.* Antitumor activity of the compounds (I) has been established through testing representatives of the compounds of the formula (I) with tumor P-388 cells in mice.

Referring, now, to the general formulas given hereinbefore, the acyl group represented by $R_1$, $R'_1$ is an acyl group derived from a carboxylic acid, carbamic acid or carbonic acid derivative having a molecular weight of no more than about 300 or an acyl group containing about 1 to about 20 carbon atoms. The term "acyl group" encompasses, among others, saturated and unsaturated aliphatic acyl groups, saturated and unsaturated alicyclic acyl groups; aromatic acyl groups; saturated and unsaturated heterocyclic acyl groups; N-acyl-α-amino acid type acyl groups; carbamoyl type acyl group and an acyl group derived from half ester or carbonic acid.

Thus, such acyl groups may for example be the groups represented by the formula:

$$-CO-R_2$$

(wherein $R_2$ is hydrogen or an optionally substituted or unsubstituted alkyl, alkenyl, cycloalkyl, cycloalkenyl, aryl or heterocyclic group, said cycloalkyl, cycloalkenyl, aryl or heterocyclic group being optionally attached to the carbonyl carbon through an alkylene chain), the groups having the formula:

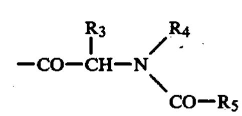

(wherein $R_3$ is hydrogen or an optionally substituted or unsubstituted alkyl, cycloalkyl, aryl, indolyl or imidazolyl group, said cycloalkyl, aryl, indolyl or imidazolyl group being optionally attached to the alpha-carbon atom through an alkylene chain; $R_4$ is hydrogen or an optionally substituted or unsubstituted alkyl, cycloalkyl, cycloalkylalkyl, aryl or benzyl group; $R_5$ is hydrogen, alkoxy, bornyloxy, isobornyloxy, benzyloxy or an optionally substituted or unsubstituted alkyl, alkenyl, cycloalkyl, cycloalkenyl, aryl or heterocyclic group, said cycloalkyl, cycloalkenyl, aryl or heterocyclic group being optionally attached to the carbonyl carbon atom adjacent the nitrogen atom through an alkylene chain), or the groups represented by the formula:

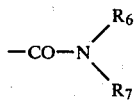

(wherein $R_6$ and $R_7$ may be the same or different and each is hydrogen or an optionally substituted or unsubstituted hydrocarbon residue or heterocyclic group, $R_6$ and $R_7$ optionally forming a heterocyclic group as taken together with the adjacent nitrogen atom), or the groups represented by the formula:

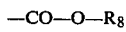

(wherein $R_8$ may be an optionally substituted or unsubstituted hydrocarbon residue).

When the acyl group represented by $R_1$ and $R'_1$ is a group having the formula:

(wherein $R_2$ is as defined hereinbefore), the alkyl group as represented by $R_2$ may be an alkyl group having about 1 to about 18 carbon atoms (e.g. methyl, ethyl, propyl, isopropyl, butyl, isobutyl, sec-butyl, tert-butyl, pentyl, isopentyl, 1-methylpropyl, hexyl, isohexyl, heptyl, 3-heptyl, octyl, nonyl, decyl, undecyl, dodecyl, tridecyl, tetradecyl, pentadecyl, hexadecyl, heptadecyl, octadecyl, 1,2-dimethylpropyl, 1-ethylpropyl, 1,2,2-trimethylpropyl, 1-propylbutyl, 2-ethylhexyl, etc.), although alkyl groups of about 1 to 6 carbon atoms are preferable. Preferred examples of alkenyl group $R_2$ are alkenyls of about 2 to 18 carbon atoms (e.g. vinyl, allyl, 1-methylvinyl, 2-methylvinyl, 1-octenyl, 1-decenyl, 1,3-pentadienyl, oleyl, etc.), with alkenyls of about 2 to 4 carbon atoms being particularly desirable.

As examples of cycloalkyl group $R_2$, there may be mentioned cycloalkyls of about 3 to 10 carbon atoms (e.g. cyclopropyl, cyclobutyl, cyclopentyl, cyclohexyl, cycloheptyl, cyclooctyl, norbornyl, adamantyl, etc.), to which a benzene ring may be optionally fused, as in e.g. 1- or 2-indanyl, benzocyclobutyl, etc.

As examples of cycloalkenyl group $R_2$, there may be mentioned cycloalkenyls of about 3 to 10 carbon atoms (e.g. 1-cyclobutenyl, 1-, 2- or 3-cyclopentenyl, 1-, 2- or 3-cyclohexenyl, 4-cycloheptenyl, 4-cyclooctenyl, 1,4-cyclohexadienyl, 4-norbornenyl, 2,4,6-cycloheptatrienyl, etc.).

The aryl group $R_2$ may for example be phenyl, α- or β-naphthyl or the like, although phenyl is especially desirable.

The heterocyclic group $R_2$ may for example be a 4-, 5- or 6-membered heterocyclic group including N, O or/and S, whether saturated or unsaturated, and may have a benzene ring fused thereto. As examples of such N-containing 4,5- or 6-membered heterocyclic group, there may be mentioned azetidinyl, pyridyl (e.g. 2-, 3- or 4-pyridyl), 1,2,3,4-tetrahydropyridyl, piperidyl, quinolyl, 1,2-dihydroquinolyl, 3- or 4-isoquinolyl, 1,2-dihydroisoquinolyl, pyrrolyl, pyrrolinyl, pyrrolidinyl, indolyl, etc. The oxygen-containing 5- or 6-membered heterocyclic group may for example be furyl, pyranyl, dihydropyranyl, benzofuryl or benzopyranyl, while said sulfur-containing 5- or 6-membered heterocyclic group may for example be thienyl, benzothienyl or the like. The above heterocyclic groups may each include 2 to 4 hetero-atoms, which may be the same or different, such as N, O or/and S. As examples of such heterocyclic groups, there may be mentioned imidazolyl, pyrazolyl, pyrazinyl, pyrimidinyl, pyridazinyl, 2-imidazolyl, imidazolidinyl, benzoimidazolyl, indazolyl, quinoxalyl, quinazolinyl, cinnolinyl, 1,4-dioxanyl, 1,4-benzodioxanyl, 1,2- or 1,3-dithiolanyl, 1,3-dithianyl, isooxazolyl, oxazolyl, morpholinyl, benzoisoxazolyl, benzoxazolyl, isothiazolyl, thiazolyl, benzoisothiazolyl, benzothiazolyl, benzothiazinyl, 1,2,4-, 1,2,5- or 1,3,4-oxadiazolyl, 1,2,3-, 1,2,4-, 1,2,5- or 1,3,4-thiadiazolyl, 1,2,3-, 1,2,5- or 1,3,4-triazolyl, 1,3,5-triazinyl, benzotriazolyl, 1,2,3,4-tetrazolyl, etc. Generally speaking, when said heterocyclic groups are strongly basic groups having a NH group, such as azetidinyl, 1,2,3,4-tetrahydropyridyl, piperidyl, 1,2-dihydroquinolyl, 1,2-dihydroisoquinolyl, pyrrolyl, pyrrolinyl, pyrrolidinyl, pyrazolyl, 2-imidazolinyl, imidazolidinyl, indazolyl, morpholinyl, 1,2,3-, 1,2,5- or 1,3,4-triazolyl, benzotriazolyl, 1,2,3,4-tetrazolyl, etc., it is desirable that a suitable substituent, which will be described hereinafter, be present in the N-position or an alkylene group, which will also be described hereinafter, be attached to the N atom.

The cyclic group $R_2$ (i.e. said optionally substituted cycloalkyl, cycloalkenyl or aryl or heterocyclic group) may optionally be attached to the carbonyl carbon of —CO—$R_2$ through an alkylene chain. Therefore, when said cyclic group is attached to an alkylene chain, $R_2$ represents an optionally substituted cycloalkylalkyl, cycloalkenylalkyl, aralkyl or heterocycle-alkyl group. The alkylene chain may consist in a straight-chain or branched alkylene group of about 1 to 4 carbon atoms (e.g. methylene, ethylene, methylmethylene (ethylidene), propylene, butylene, 1-, 2- or 3-methylpropylene, 1- or 2-ethylethylene, propylmethylene, 1,1- or 1,2-dimethylethylene, isopropylmethylene, etc.). As examples of said cycloalkylalkyl group, there may be mentioned 1-adamantylmethyl, cyclohexylmethyl, 3-cyclohexylpropyl, 2-cyclopentenylmethyl, 2-cyclopentylethyl, cyclopropylmethyl, cyclobutylethyl, cyclopentylmethyl, 2-cyclohexylethyl, 2-methyl-2-cyclohexylpropyl and so on.

As examples of said cycloalkenylalkyl group, there may be mentioned 1-, 2- or 3-cyclopentenylmethyl, 1-, 2- or 3-cyclohexenylmethyl, 4-cycloheptenyl-3-propyl, 1,4-cyclohexadienylmethyl and so on.

Typical examples of said aralkyl group are benzyl, phenethyl, 3-phenylpropyl, α-methylbenzyl, 1-methyl-3-phenylpropyl, 4-phenylbutyl and so on.

As examples of said heterocyclic-alkyl group, there may be mentioned 3-indolylmethyl, 3-(3-indolyl)propyl, 2-pyridylmethyl, 3-pyridylmethyl, 4-pyridylmethyl, 3-(2-thienyl)propyl, 2-benzothiazolylmethyl, 2-benzoxazolylmethyl, 3-benzoisothiazolylmethyl, 3-benzoisoxazolylmethyl, furfuryl, 2-thenyl and so on.

When $R_2$ is an N-containing heterocyclic group, with its N atom linked to the carbonyl carbon of the acyl group —CO—$R_2$, the particular heterocyclic group is defined as being always attached to the carbonyl group through the alkylene chain mentioned above. As examples of such heterocycle-alkyl group with an alkylene chain attached to its N atom, there may be mentioned 1-pyrrolylmethyl, 2-oxo-1-pyrrolidinylmethyl, 1-imidazolylmethyl, 3,5-dimethyl-1-pyrazolylmethyl, 1-piperidylethyl (or 1-piperidinoethyl), 4-morpholinylmethyl (or 4-morpholinomethyl), 1-tetrazolylmethyl, 2,5-dioxo-1-pyrrolidinylmethyl, 1,3-dioxo-2-isoindolylmethyl, 2-thioxo-4-oxo-3-thiazolidinylmethyl, 3,5-diiodo-4-oxo-1,4-dihydropyridyl-1-methyl, 4-methyl-1-piperazinylmethyl, 1-indolylethyl and so on.

The alkyl, alkenyl, cycloalkyl, cycloalkenyl, aryl or heterocyclic group $R_2$ may optionally be substituted, the substituents being exemplified by alkoxy groups of 1 to 4 carbon atoms (e.g. methoxy, ethoxy, propoxy, isopropoxy, butoxy, isobutoxy, sec-butoxy, tert-butoxy, etc.), alkanoyl groups of 2 to 4 carbon atoms (e.g. acetyl, propionyl, butyryl, isobutyryl, etc.), alkanoyloxy groups of 2 to 4 carbon atoms (e.g. acetyloxy, propionyloxy, butyryloxy, isobutyryloxy, etc.), alkoxycarbonyl groups of 2 to 4 carbon atoms (e.g. methoxycarbonyl, ethoxycarbonyl, propoxycarbonyl, isopropoxycarbonyl, etc.), halogens (e.g. chlorine, fluorine, bromine and iodine), nitro, cyano, trifluoromethyl, di-$C_{1-4}$ alkylamino (e.g. dimethylamino, diethylamino, dipropylamino, diisopropylamino, dibutylamino, etc.), $C_{1-4}$ alkylthio (e.g. methylthio, ethylthio, n-propylthio, isopropylthio, butylthio, isobutylthio, sec-butylthio, tert-butylthio, etc.), methylsulfinyl, methylsulfonyl, oxo, thioxo, $C_{1-4}$ alkanoylamido (e.g. formamido, acetamido, propionylamino, butyrylamino, isobutyrylamino, etc.) and so on. When $R_2$ is a cyclic group (i.e. cycloalkyl, cycloalkenyl, aryl or heterocyclic), alkyl groups of 1 to 4 carbon atoms (e.g. methyl, ethyl, propyl, isopropyl, butyl, isobutyl, sec-butyl, tert-butyl, etc.) may also be mentioned as the substituents. These substituents may be the same or different and may be present in the number of 1 to 3.

The substituted $C_{1-18}$ alkyl group $R_2$ may for example be methoxymethyl, butoxymethyl, methylthiomethyl, 2-methylthioethyl, 2-ethylthioethyl, 2-isopropylthioethyl, 2-butylthioethyl, 2-isobutylthioethyl, acetyloxymethyl, 2-acetyloxyethyl, ethoxycarbonylmethyl, 2-butoxycarbonylethyl, fluoromethyl, chloromethyl, 2-chloroethyl, 3-chloropropyl, 4-chlorobutyl, 3,3,3-trichloropropyl, trifluoromethyl, bromomethyl, 4-bromobutyl, 5-bromopentyl, iodomethyl, 2-iodoethyl, 1,1-dimethyl-2,2-dichloroethyl, 2-chloro-1-chloromethyl-1-methylethyl, cyanomethyl, 2-methylsulfinylethyl or methylsulfonylmethyl. 1-Chlorovinyl may be mentioned as an example of said substituted $C_{2-10}$ alkenyl group $R_2$.

As examples of substituted cyclo-$C_{3-10}$ alkyl group $R_2$, there may be mentioned 2,2-dimethylcyclopropyl, 2-propylcyclopropyl, 2-butylcyclopropyl, 4-isobutylcyclohexyl, 2-bromocyclopropyl, 2-chlorocyclobutyl, 4-chlorocyclohexyl, 2-iodocyclohexyl, 2,2-difluorocyclobutyl, 3-methoxycyclohexyl, 2,2-dimethyl-3-acetylcyclobutyl, 4-acetylcyclohexyl, 2-cyanocyclohexyl, 2-cyanocyclobutyl, 4-cyanocyclohexyl, 4-dimethylaminocyclohexyl and so on.

As examples of substituted cyclo-$C_{3-10}$ alkenyl group $R_2$, there may be mentioned 2-cyano-2-cyclohexenyl, 3,3-dimethyl-4-cyclobutenyl, 4-ethoxycarbonyl-1-cyclohexenyl, 4-butoxycarbonyl-1-cyclohexenyl and so on.

Typical examples of substituted aryl group $R_2$ are 2-, 3- or 4-methylphenyl, 4-tert-butylphenyl, 2-, 3- or 4-chlorophenyl, 2-, 3- or 4-bromophenyl, 2-, 3- or 4-indophenyl, 2-, 3- or 4-fluorophenyl, 2- or 4-methoxyphenyl, 4-butoxyphenyl, 4-methoxycarbonylphenyl, 3-acetylphenyl, 2-, 3- or 4-nitrophenyl, 3- or 4-cyanophenyl, 4-dimethylaminophenyl, 4-diethylaminophenyl, 4-acetoxyphenyl, 4-butyryloxyphenyl, 2,4-, 2,5-, 2,6-, 3,4- or 3,5-dichlorophenyl, 3,4-dimethoxyphenyl, 3,4,5-trimethoxyphenyl, 3,4-methylenedioxyphenyl, 3-trifluoromethylphenyl, 4-methylthiophenyl, 4-methylsulfonylphenyl, 4-acetamidophenyl and so on.

The optionally substituted or unsubstituted 4, 5- or 6-membered heterocyclic group $R_2$ may for example be 1-acetyl-2-azetidinyl, 1-methyl-2-pyrrolyl, 3-methoxy-2-furyl, 3-methyl-2-furyl, 5-methyl-2-furyl, 5-nitro-2-furyl, 3-methyl-2-thienyl, 3-bromo-4,5-dimethyl-2-thienyl, 2-methyl-4-thiazolyl, 1,2-dimethyl-4-chloro-5-imidazolyl, 1-butyl-4-pyrazolyl, 2,4-dichloro-4-isothiazolyl, 5-methyl-1,2,3-4-thiadiazolyl, 3,5-dimethyl-4-isooxazolyl, 2-methyl-5-diisopropylamino-4-oxazolyl, 5-methyl-1, 2,5-oxadiazolyl-3,4-methoxy-1,2,5-oxadiazolyl-3, 5-methyl-1,3,4-oxadiazolyl-2, 3-methyl-1,2,3-thiadiazolyl-5, 5-methyl-1,3,4-thiadiazolyl-2, 5-methyl-1,2,3-thiadiazolyl-4, 1-methyl-1,2,3-triazolyl-4, 2-ethyl-1,2,3,4-tetrazolyl-5, 5-nitro-2-pyridinyl, 6-ethyl-4-pyridinyl, 5-ethoxycarbonyl-3-pyridinyl, 5-chloro-3-pyridinyl, 1-butyryl-2-piperidyl, 2-oxo-5-pyranyl, 7-methoxy-3,4-dihydro-2H-pyranyl-2,1-acethyl-2-pyrrolidinyl 1-propyl-5-oxo-3-pyrrolidinyl, 3-methyl-2,4-dioxo-5-thiazolinyl, 4-, 5-, 6- or 7-nitro-3-indolyl, 5-fluoro-2-indolyl, 2-methyl-5-methoxy-3-indolyl, 1-methyl-2-indolyl, 5-chloro-2-benzothienyl, 3-methyl-2-benzofuryl, 1-methyl-2-benzoimidazolyl, 6-nitro-2-benzothiazolyl, 4-chloro-3-quinolyl, 6-methoxy-2-quinolyl, 2,4-dimethoxy-3-quinolyl, 2-methyl-1-oxo-3-isocarbostyryl, 7-methyl-3-coumaryl, 4-methyl-2-quinazolyl, 3-propyl-2,4-dioxo-5-imidazolinyl, 7-methoxycarbonyl-2-oxo-1,2-dihydro-3-quinazolyl, 2-furyl, 2-thienyl, 3-isoxazolyl, 4-imidazolyl, 1,2,5-thiadiazolyl-3, 2-, 3- or 4-pyridyl, 2-pyrazinyl, 2-pyrimidinyl, 2-s-triazinyl, 1,2-dithiolanyl, 3-indolyl, 2-benzothienyl, 2-benzofuryl, 3-benzopyrazolyl, 2-benzoimidazolyl, 2-benzoxazolyl, 3-benzoisoxazolyl, 3-benzoisothiazolyl, 2-benzothiazolyl, 2-benzo-1,4-oxazinyl, 3-quinolyl or 1-isoquinolyl.

As examples of the substituted cycloalkylalkyl group $R_2$, there may be mentioned 3-acetyl-2,2-dimethyl-1-cyclobutylmethyl, 3-acetoxy-2,2-dimethyl-1-cyclobutylmethyl, 2-(3-chloro-1-cyclobutyl)ethyl, 2,3-dimethyl-1-cyclopentylmethyl, 2-isopropyl-1-cyclopentylmethyl, cis- or trans-4-acetamido-1-cyclohexylmethyl, cis- or trans-4-tert-butyl-1-cyclohexylmethyl, cis- or trans-2-(4-acetamido-1-cyclohexyl)ethyl and so on.

As examples of the substituted cycloalkenylalkyl group $R_2$, there may be mentioned 2-(4-isopropyl-1-cyclohexenyl)ethyl, 1-ethyl-2-(4-isopropyl-1-cyclohexenyl)ethyl, 3-methoxy-4-methyl-3-cyclohexenylmethyl and so on.

The substituted aralkyl group $R_2$ may for example be 4-bromobenzyl, 2-, 3- or 4-chlorobenzyl, 2,5-or 3,4-dimethoxybenzyl, 4-ethoxybenzyl, 4-fluorobenzyl, 3- or 4-methoxybenzyl, 4-methoxyphenethyl, 1- or 2-naphthylmethyl, 2-, 3- or 4-nitrobenzyl, 3-nitrophenethyl, benzyl, 1-, 2- or 3-phenylpropyl, 2-, 3- or 4-methylbenzyl, 3,4,5-trimethoxybenzyl or α-methylphenethyl.

As examples of the substituted heterocycle-alkyl group $R_2$, there may be mentioned 5-ethyl-3-indolylmethyl, 5-fluoro-3-indolylmethyl, 5-methoxy-3-indolylmethyl, 5-methyl-3-indolylmethyl, 1-methyl-5-tetrazolylmethyl, 2-(1-piperidinyl)ethyl and so on.

When the acyl group R₁ or R′₁ is a group of the formula:

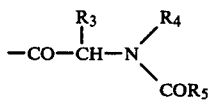

(wherein R₃, R₄ and R₅ are as respectively defined hereinbefore), the alkyl, cycloalkyl and aryl groups represented by R₃, R₄ and R₅ may for example be the corresponding groups mentioned for R₂. Thus, as examples of the cycloalkylalkyl group, there may be mentioned the corresponding groups mentioned for R₂.

As examples of the alkenyl, cycloalkenyl or heterocyclic group R₅, there may be mentioned the corresponding groups mentioned for R₂.

As examples of the alkoxy group R₅, there may be mentioned alkoxy groups of about 1 to 7 carbon atoms (e.g. methoxy, ethoxy, propoxy, isopropoxy, butoxy, isobutoxy, sec-butoxy, tert-butoxy, pentoxy, hexyloxy, heptyloxy, etc.), although alkoxy groups of about 1 to 4 carbon atoms are preferred.

The cycloalkyl, aryl, indolyl or imidazolyl group R₃ may optionally be attached to the α-carbon atom through an alkylene chain. Moreover, the cycloalkyl, cycloalkenyl, aryl or heterocyclic group R₅ may optionally be attached to the carbonyl carbon adjacent the nitrogen atom through an alkylene chain. As examples of such alkylene chains, there may be mentioned the alkylene chains given hereinbefore for R₂.

Therefore, when such an alkylene chain is interposed, R₃ represents cycloalkylalkyl, aralkyl, indolylalkyl, imidazolylalkyl, cycloalkenylalkyl or heterocycle-alkyl groups.

An examples of such cycloalkylalkyl, cycloalkenylalkyl, aralkyl- and heterocycle-alkyl groups, there may be mentioned the corresponding groups given for R₂.

The indolylalkyl group may for example be 3-indolylmethyl, 2-(3-indolyl)ethyl, 3-(3-indolyl)propyl or 4-(3-indolyl)butyl. The imidazolylalkyl group may for example be 4-imidazolylmethyl, 2-(4-imidazolyl)ethyl, 3-(4-imidazolyl)propyl, 4-(4-imidazolyl)butyl.

The groups represented by R₃ and R₄, as well as the alkyl, alkenyl, cycloalkyl, cycloalkenyl, aryl, heterocyclic, cycloalkylalkyl, cycloalkenylalkyl, aralkyl and heterocycle-alkyl group represented by R₅, may optionally be substituted and such substituents may be similar to those mentioned as substituents on the groups represented by R₂.

As examples of such substituted groups R₃, R₄ and R₅, there may be mentioned the corresponding substituted groups R₂.

As examples of substituted indolyl R₃, there may be mentioned 5-bromo-2-indolyl, 5-chloro-2-indolyl, 5-fluoro-2-indolyl, 5-methoxy-2-indolyl, 1-methyl-2-indolyl, 5-methyl-2-indolyl and so on. The substituted imidazolyl group R₃ may for example be 1-methyl-5-imidazolyl, 3-methyl-5-imidazolyl or 2-methyl-4-imidazolyl.

As examples of the substituted indolylalkyl group R₃, there may be mentioned 5-bromo-2-indolylmethyl, 5-bromo-2-indolylethyl, 5-chloro-2-indolylmethyl, 5-chloro-2-indolylethyl, 5-fluoro-2-indolylmethyl, 5-fluoro-2-indolylethyl, 5-methoxy-2-indolylmethyl, 5-methoxy-2-indolylethyl, 1-methyl-2-indolylmethyl, 1-methyl-2-indolylethyl, 5-methyl-2-indolylmethyl, 5-methyl-2-indolylethyl and so on.

As examples of substituted imidazolylalkyl, R₃, there may be mentioned 1-methyl-5-imidazolylmethyl, 1-methyl-5-imidazolylethyl, 3-methyl-5-imidazolylmethyl, 3-methyl-5-imidazolylethyl, 2-methyl-4-imidazolylmethyl, 2-methyl-4-imidazolylethyl, 1-methyl-4-imidazolylmethyl, 1-methyl-4-imidazolylethyl and so on.

As examples of substituted benzyl R₄, there may be mentioned 4-bromobenzyl, 2-, 3- or 4-chlorobenzyl, 4-fluorobenzyl, 4-methoxybenzyl, 4-ethoxybenzyl, 2-, 3- or 4-methylbenzyl, 3,4-dimethoxybenzyl and so on.

As typical examples of the above-described N-acyl-α-aminoacyl group:

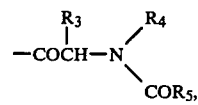

there may be mentioned N-acetyl-N-methylglycyl, N-benzoyl-N-methylglycyl, N-(4-chlorobenzoyl)-N-methylglycyl, N-acetyl-N-benzylalanyl, N-acetyl-N-methylleucyl, N-acetyl-N-methylphenylalanyl, 2-(N-acetyl-N-methyl)amino-3-methoxycarbonylpropionyl, 2-(N-acetyl-N-methyl)amino-3-methylmercaptopropionyl, 2-(N-acetyl-N-methyl)amino-3-ethylmercaptopropionyl, N$^{\alpha}$-acetyl-N$^{\alpha}$, N′-dimethylhistidinyl, N-acetyl-N-methylisoleucyl, N-acetyl-N-methylleucyl, N-acetyl-N-methylmethionyl, N-acetyl-N-methylphenylalanyl, N-acetyl-N-methyltriptophanyl, N-acetyl-N-methyl-4′-acetoxytyrosinyl, N-benzyl-N-methylvalyl, N-acetyl-N-methylphenylglycyl, N-isonicotinoyl-N-methyl-α-aminobutyryl, (N-acetyl-N-methyl)amino-3-cyanopropionyl, N-acetyl-N-methyl-α-(2-thiazolyl)glycyl, N-acetyl-N-methyl-(4′-dimethylamino)-phenylalanyl and so on.

When the acyl group represented by R₁ or R′₁ is a group of the formula:

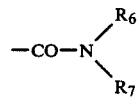

(wherein R₆ and R₇ are as respectively defined hereinbefore), the hydrocarbon residues R₆ and R₇ may for example be alkyl, alkenyl, cycloalkyl, cycloalkenyl, cycloalkylalkyl, cycloalkenylalkyl, aryl, aralkyl, phenylcycloalkyl, cycloalkylphenyl, biphenyl, etc.

As examples of said alkyl, alkenyl, cycloalkyl, cycloalkenyl, cycloalkylalkyl, cycloalkenylalkyl, aryl and aralkyl groups, there may be mentioned the corresponding groups already given for R₂.

As examples of said phenylcycloalkyl group, there may be mentioned, among others, said cycloalkyl groups of 3 to 10 carbon atoms (particularly, 3 to 7 carbon atoms) substituted by a phenyl group, e.g. 2-phenylcyclopropyl, 4-phenylcyclohexyl, etc. As examples of the cycloalkylphenyl group, there may be mentioned a phenyl group substituted by one of said cycloalkyl groups, e.g. 4-cyclopentylphenyl, 4-cyclohexylphenyl, etc. The biphenyl group may for example be 4-biphenyl.

As examples of the heterocyclic groups R₆ and R₇, there may be mentioned 4-, 5- or 6-membered heterocyclic groups including N, O or/and S atoms, which may optionally be saturated or unsaturated, and optionally be fused to a benzene ring. As examples of such heterocyclic groups, there may be mentioned azetidinyl, pyrrolyl, furyl, thienyl, thiazolyl, isothiazolyl, oxazolyl, isoxazolyl, pyrazolyl, imidazolyl, pyridyl, pyrimidinyl, pyrazinyl, triazinyl, quinolyl, quinazolyl, quinoxalyl, indolyl, benzofuranyl, benzothienyl, etc.

Optionally, $R_6$ and $R_7$ may, taken together, form a heterocyclic group in combination with the adjacent N atom and, as examples of such heterocyclic group, there may be mentioned azetidinyl, pyrrolidinyl, piperadinyl, morpholinyl and so on.

The hydrocarbon residues and heterocyclic groups, as represented by $R_6$ and $R_7$, as well as the heterocyclic group

may optionally be substituted. As examples of the substituents thereon, there may be mentioned alkoxy groups of 1 to 4 carbon atoms (e.g. methoxy, ethoxy, propoxy, isopropoxy, butoxy, isobutoxy, sec-butoxy, etc.), $C_{1-4}$ alkylthio (e.g. methylthio, ethylthio, propylthio, isopropylthio, butylthio, etc.), phenoxy, phenythio, cyclohexyloxy, halogen (e.g. fluorine, chlorine, bromine, iodine), cyano, $C_{2-5}$ alkoxycarbonyl (e.g. methoxycarbonyl, ethoxycarbonyl, propoxycarbonyl, isopropoxycarbonyl, butoxycarbonyl, isobutoxycarbonyl, sec-butoxycarbonyl, etc.), benzyloxycarbonyl, nitro, aminosulfonyl, dialkylamino (e.g. dimethylamino, diethylamino, diisopropylamino, dibutylamino, etc.) and so on. These substituents may be the same or different and may be present in the number of 1 to 3.

As to substituents on the cyclic hydrocarbon moieties, of said hydrocarbon residues, and on heterocyclic groups mentioned above, there may be mentioned, in addition to the above-mentioned substituent groups, alkyl groups of about 1 to 4 carbon atoms (which may be further substituted by said hydrocarbon residues $R_6$ and $R_7$), such as methyl, ethyl, propyl, isopropyl, butyl, trifluoromethyl, chloromethyl, 2-cyanoethyl, methoxymethyl, ethoxycarbonylmethyl, dimethylaminomethyl, etc.

As examples of substituents on alkyls $R_6$ and $R_7$, there may be mentioned the groups given as substituents on said hydrocarbon residues as well as heterocyclic groups (which may be substituted) similar to those mentioned as the heterocyclic groups $R_6$ and $R_7$.

As examples of substituted hydrocarbon residues $R_6$ and $R_7$, there may be mentioned 2-methoxyethyl, 3-methoxypropyl, 2-methoxy-1-methylethyl, 3-isopropoxypropyl, 3-sec-butoxypropyl, 3-cyclohexyloxypropyl, 3-phenoxypropyl, 2-chloroethyl, 3-chloropropyl, 4-chlorobutyl, 2-propylthioethyl, 2-phenylthioethyl, 2-cyanoethyl, 5-cyanopentyl, 4-cyanocyclohexylmethyl, methoxycarbonylmethyl, ethoxycarbonylmethyl, 1- or 2-methoxycarbonylethyl, 1-methoxycarbonylisobutyl, 5-methoxycarbonylpentyl, 5-dimethylaminopentyl, trifluoromethyl, 2-, 3- or 4-tolyl, xylyl, 2,4,5- or 2,4,6-trimethylphenyl, 2-, 3- or 4-chlorophenyl, 2,5-dichlorophenyl, 2-, 3- or 4-fluorophenyl, 4-bromophenyl, 4-iodophenyl, 2- or 3-trifluorophenyl, 2-, 3- or 4-nitrophenyl, 4-chloro-3-trifluoromethylphenyl, 2-methyl-4-nitrophenyl, 5-nitro-1-naphthyl, 8-chloro-1-naphthyl, 4-methoxycarbonylphenyl, 4-ethoxycarbonylphenyl, 4-amino-sulfonylphenyl, 2-, 3- or 4-methoxyphenyl, 4-ethoxyphenyl, 2,5-dimethoxyphenyl, 1-methoxycarbonyl-2-phenethyl, 1-methoxycarbonyl-1-phenylmethyl, 2-, 3- or 4-methylbenzyl, 2-, 3- or 4-chlorobenzyl, 2- or 3-fluorobenzyl, 3-iodobenzyl, 2,4- or 3,4-dichlorobenzyl, 4-methoxybenzyl, α-methylbenzyl, 1,1-dimethylphenethyl, 4-methoxyphenethyl, 2-, 3- or 4-picolyl, 5-methyl-2-thenyl, 5-methylfurfuryl, 3-piperazinopropyl, 2-morpholinoethyl, 4-methyl-1-piperazinylpropyl, 2-(1-methyl-2-pyrrolidinyl)ethyl, 2-thiazolylmethyl, 2-methyl-4-oxazolylmethyl, 5-chloro-1-methyl-3-indolylethyl and so on.

As examples of the optionally substituted or unsubstituted heterocyclic groups $R_6$ and $R_7$, there may be mentioned 1-methyl-2-azetidinyl, 1-methyl-2-pyrrolyl, 5-methyl-2-furyl, 5-nitro-2-furyl, 3-methyl-2-thienyl, 4,5-dichloro-2-thienyl, 2-methyl-4-thiazolyl, 1,1-methyl-4-imidazolyl, 2-dimethyl-4-chloro-5-imidazolyl, 3,5-bismethylthio-4-isothiazolyl, 3-methyl-5-isoxazolyl, 2-methyl-4-oxazolyl, 1-methyl-3-pyrazolyl, 2-, 3- or 4-pyridyl, 4,5,6-trichloro-2-pyrimidinyl, 3,5,6-trichloro-2-pyrazinyl, 4,6-dichloro-2-s-triazinyl, 3- or 4-quinolyl, 2-quinazolyl, 2-quinoxazolyl, 5-fluoro-1-methyl-3-indolyl, 2-benzofuryl, 2-benzothienyl, etc. When the heterocyclic group of

is substituted, the resultant group may for example may be 2-, 3- or 4-methyl-1-piperidinyl, 4-methyl-1-piperazinyl, 2,6-dimethylmorpholino or 2-propyl-1-piperidinyl.

As typical examples of

wherein both $R_6$ and $R_7$ are other than hydrogen, there may be mentioned dimethylamino, diethylamino, dipropylamino, diisopropylamino, diisobutylamino, dibenzylamino, diphenethylamino, diphenylpropylaminol, (N-methyl-N-benzyl)amino, (N-ethyl-N-butyl)amino, (N-methyl-N-cyclopentyl)amino, (N-methyl-N-cyclohexyl)amino, (N-methyl-N-furfuryl)amino and so on.

When the acyl group represented by $R_1$ or $R'_1$ is a group of the formula:

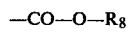

(wherein $R_8$ is as defined hereinbefore), the hydrocarbon residue $R_8$ may for example be alkyl, cycloalkyl, aryl and aralkyl.

As examples of said alkyl group $R_8$, there may be mentioned alkyl groups of 1 to 18 carbon atoms (e.g. methyl, ethyl, propyl, isopropyl, butyl, isobutyl, sec-butyl, tert-butyl, pentyl, hexyl, benzyl, octyl, nonyl, decyl, undecyl, dodecyl, tetradecyl, hexadecyl, octadecyl, 1-ethylpropyl, neopentyl, 1-ethylpentyl, 1- or 2-ethyhexyl), although, among others, alkyl groups of about 1 to 8 carbon atoms are preferable.

As examples of said cycloalkyl group $R_8$, there may be mentioned cycloalkyl group of 3 to 10 carbon atoms (e.g. cyclopropyl, cyclobutyl, cyclopentyl, cyclohexyl, cycloheptyl, cyclooctyl, ademantyl).

As examples of said aryl group $R_8$, there may be mentioned phenyl, α- or β-naphthyl.

As examples of said aralkyl group $R_8$, there may be mentioned those alkyl groups of about 1 to 4 carbon atoms substituted by a said aryl group, especially a phenyl group (e.g. benzyl, phenethyl, 1- or 3-phenylpropyl, 1-phenylethyl, 1-methyl-3-phenylpropyl, 4-phenylbutyl).

The hydrocarbon residue $R_8$ mentioned above may optionally be substituted, the substituents being exemplified by alkoxy groups of 1 to 4 carbon atoms (e.g. methoxy, ethoxy, propoxy, isopropoxy, butoxy, isobutoxy, sec-butoxy), phenoxy, benzyloxy, halogens (e.g. fluorine, chlorine, bromine and iodine) and cyano. These substituents may be the same or different and may be present in the number of 1 to 3.

As to substituents on the cyclic hydrocarbon moieties of said hydrocarbon groups (e.g. cycloalkyl, aryl moieties), there may be mentioned, in addition to the above-mentioned substituent groups, alkyl groups of about 1 to 4 carbon atoms (e.g. methyl, ethyl, propyl, isopropyl, butyl), and halogenated alkyl of 1 to 4 carbon atoms (e.g. chloromethyl, bromomethyl, dichloromethyl, chlorodifluoromethyl, trifluoromethyl).

As examples of said substituted alkyl groups $R_8$, there may be mentioned, among others, 2-methoxyethyl, 2-ethoxyethyl, 2-butoxyethyl, 4-ethoxybutyl, chloromethyl, 1- or 2-chloroethyl, 2-bromoethyl, 2-fluoroethyl, 3-chloropropyl, 2,3-dichloropropyl, 2-chloroisopropyl, 1-chloromethyl-2-chloroethyl, 2,2,2-trichloroethyl, 2,2,2-trifluoroethyl and 1- or 2-cyanopropyl.

As examples of said substituted cycloalkyl group $R_8$, there may be mentioned, among others, 1-methylcyclobutyl, 1-methylcyclopentyl and 1-methylcyclohexyl. Typical examples of said substituted aralkyl groups $R_8$ are, among others, 2-, 3- or 4-chlorobenzyl, 4-bromobenzyl, 4-methoxybenzyl, 2,5- or 3,4-dimethoxybenzyl and 3-chloro-4-methylbenzyl. Typical examples of said substituted aryl groups $R_8$ are, among others, 2-, 3- or 4-methylphenyl, 2-, 3- or 4-methoxyphenyl, 4-ethoxyphenyl, 2-, 3- or 4-chlorophenyl, 4-fluorophenyl, 2,4-dichlorophenyl, 2-, 3- or 4-chloromethylphenyl, 4-trifluoromethylphenyl, 4-bromophenyl and 3-dimetylaminophenyl.

The microorganism employable in the method of this invention may be any microorganism of the genus Bacillus, the genus Streptomyces or the genus Actinomyces, inclusive of any mutants thereof, which is able to transform the 20-methoxy group of maytansinoid compound (II) into a hydroxy group. As examples of such microorganism, there may be mentioned *Bacillus megaterium* IFO 12108 (NRRL B-349), *Streptomyces flavotricini* IFO 12770 (ATCC 23621 & 19757), *Streptomyces platensis* IFO 12901 (ATCC 23948), *Streptomyces libani* IFO 13452 (ATCC 23732) and *Actinomyces nigresens* IFO 12894 (ATCC 23941).

The microorganisms assigned the above-mentioned IFO numbers are found on Institute for Fermentation Osaka List of Cultures 1978 sixth edition, published by the Institute for Fermentation, Osaka (IFO), Japan. The above-mentioned microorganisms assigned the IFO numbers of IFO 12108, IFO 12770, IFO 12901, IFO 12894 are also found on Institute for Fermentation Osaka List of Cultures 1972 fifth edition, and the microorganism assigned the IFO number of IFO 13452 is also found on Institute for Fermentation Osaka List of Cultures 1975 Supplement of the fifth edition. The microorganisms appearing on the above-mentioned Lists can be obtained from the same Institute.

Generally speaking, microorganisms of the genera Bacillus, Streptomyces and Actinomyces are liable to vary in characters and mutants can be easily derived therefrom, for example by such artificial mutagenic treatments as irradiation with X-rays, ultraviolet ray or other radiation, or by means of an artificial mutagen (e.g. nitrosoguanidine, ethylenimine). All such mutants can be employed in the practice of this invention, insofar as they are able to transform the 20-methoxy group of maytansinoid compound (II) into a hydroxy group.

The medium used in the cultivation of the above microorganism may be any fluid or solid medium containing the nutrients which the particular microorganisms are able to utilize, although a fluid medium is preferable for commercial scale operations. The culture medium is prepared using the carbon sources which will be assimilated by the microorganism and the nitrogen sources, inorganic materials, trace nutrients, etc. which will be digested by the microorganism. Thus, as such carbon sources, there may be employed glucose, lactose, sucrose, maltose, dextrin, starch, glycerin, mannitol, sorbitol, fats and oils (e.g. soybean oil, lard oil, chicken oil, etc.) and so on, while the nitrogen sources may be meat extract, yeast extract, dried yeast, soybean meal, corn steep liquor, peptone, cottonseed meal, spent nolasses, urea, ammonium salts (e.g. ammonium sulfate, ammonium chloride, ammonium nitrate, ammonium acetate, etc.) and so on. The medium may further contain appropriate amounts of salts, such as sodium, potassium, calcium, magnesium, etc., metal salts such as salts of iron, manganese, zinc, cobalt, nickel, etc., salts of phosphoric acid and boric acid, and salts of organic acids such as acetic acid, propionic acid, etc. The medium may also contain other components such as amino acids (e.g. glutamic acid, aspartic acid, alanine, glycine, lysine, methionine, proline, etc.), peptides (e.g. dipeptides, tripeptides, etc.), vitamins (e.g. $B_1$, $B_2$, nicotinic acid, $B_{12}$, C, E, etc.), nucleic acids (e.g. purine, pyrimidine and their derivatives, etc.) and so on. It is, of course, possible to add inorganic or organic acids, alkalies, buffers, etc. for the purpose of adjusting the pH of the medium, or to add suitable amounts of oils, surfactants, etc. for defoaming purposes.

The cultivation may be carried out by any procedure such as stationary, shake or aerobic stirred culture. Of course, submerged aerobic culture is preferred for commercial operations. While the cultural conditions depend on the condition and composition of the medium, the microorganisms, the cultural procedure and so on, it is normally desirable that the cultivation be carried out at a temperature of 20° to 45° C. and at an initial pH of substantial neutrality. The temperature in the intermediate stage of cultivation is desirably between 24° C. and 37° C., and the initial pH of the medium is desirably between 6.5 and 8.5. While the cultivation is completed in about 6 to 100 hours, the incubation period of 16 to 60 hours is particularly satisfactory.

The term "culture broth" as used herein means the product obtained by the cultivation process described above. The term "processed matter of the culture broth" as used herein means the cells or disrupted cells containing a demethylation enzyme system which are obtainable by subjecting the above-mentioned culture broth to any of such physical or chemical treatments as filtration, centrifugation, ultrasonic disruption, treating with a French press, alumina grinding or treatment with a bacteriolytic enzyme, a surfactant or an organic solvent.

The demethylation enzyme system purified by the conventional procedure and the bacterial cells or demethylation enzyme system immobilized by the conventional procedure may also be successfully utilized.

The method of this invention comprises bringing the starting compound (II) into contact with said culture broth or the processed matter of the culture broth. The concentration of the starting compound in the reaction system is within the range of 1 to 400 µg/ml, advantageously 1 to 200 µg/ml, and preferably 50 to 200 µg/ml. The preferred reaction temperature is 20° to 50° C. and the preferred pH is 5 to 10, although temperatures from 24° to 40° C. and pH levels from 6 to 9 are especially desirable. The reaction time may range from 10 minutes to 100 hours, preferably, 1 to 48 hours and more preferably 8 to 48 hours. While the reaction may be carried out under stationary, shake, aerobic submerged or stirred conditions, it is more advantageous to conduct the reaction under shake, aerated or stirred culture conditions. If desired, a reaction stimulator, an enzyme stabilizer and other agents may be added to the reaction system.

As examples of said reaction stimulator, there may be mentioned coenzymes such as nicotinamideadenine dinucleotide (NAD), nicotinamideadenine dinucleotide phosphate (NADP), flavine mononucleotide (FMN), flavine-adenine dinucleotide (FAD), etc., their precursors (e.g. adenine, adenosine, adenylic acid, nicotinamide, flavine, riboflavine, etc.), metal salts (e.g. magnesium chloride, manganese chloride, ferrous chloride, ferric chloride, zinc chloride, etc.), surfactants [e.g. Triton X-100 (Rohm and Haas Co., U.S.A.), Brij-58 (Kao-Atlas Co., Japan), etc.], 3', 5'-cyclic adenylic acid and so on. The enzyme stabilizer may for instance be cysteine, 2-mercaptoethanol, dithiothreitol, sucrose or glycerol.

The novel substance (III) thus produced can be detected by thin-layer chromatography (hereinafter referred to briefly as TLC.). First, the reaction mixture is extracted with ethyl acetate, the extract is concentrated to one-hundredth of its initial volume and TLC is carried out on the concentrate using a procoated silica gel plate (Kieselgel 60 $F_{254}$, Merck, Germany, 0.25 mm, 20×20 cm) and a 9:1 mixture of chloroform and methanol. The chromatogram is irradiated with ultraviolet light at 2537 A to detect the desired compound.

The product compound (III) can be isolated from the reaction mixture by utilizing the purification procedures normally used for the recovery of microbial metabolites, by taking advantage of the weakly acidic and lipophilic property of compounds of this class. By way of example, the procedure utilizing the difference in solubility between the compound (III) and impurity, the procedure which takes advantage of the differential adsorptive affinity of various adsorbents, e.g. activated charcoal, macroporous nonionic resins, silica gel, alumina, etc., for the compound (III) versus impurities and the procedure or removing impurities by means of ion exchange resins may be employed alone, in combination or in repetition. When resorted to the procedure relying on the solubility difference, use is made of a suitable extraction solvent such as water-immiscible organic solvents, e.g. fatty acid esters (e.g. ethyl acetate, amyl acetate, etc.), alcohols (e.g. butanol), halogenated hydrocarbons (e.g. chloroform), ketones (e.g. methyl isobutyl ketone, etc.) and so on. The extraction procedure is carried out in the weakly acidic region; preferably, the compound (III) is extracted with ethyl acetate from the culture broth filtrate preadjusted to pH 6. The extract thus obtained is washed with water and concentrated under reduced pressure. To the residue is added a nonpolar solvent such as petroleum ether and the crude product (i) containing the active compound is recovered. Since the TLC of this crude product gives many spots other than that of the novel demethylmaytansinoid compound (III), the following stepwise purification procedure is carried out. Thus, normally various adsorption chromatographic techniques are useful for this purpose and, as the adsorbents, the common supports such as silica gel, alumina, macroporous nonionic adsorbent resins can be utilized. However, for the purification of crude product (i), silica gel is the most advantageous of all the adsorbents. Development is started with petroleum ether and hexane, followed by the elution of the novel demethylmaytansinoid compound (III) with a solvent admixed with one or more polar solvent such as ethyl acetate, acetone, ethanol or methanol. By way of example, column chromatography is carried out using silica gel (Merck, Germany, 0.05 to 0.2 mm) as the carrier and with incremental ratios of ethyl acetate to hexane. The eluate is assayed by TLC and the fractions containing demethylmaytansinoid compound (III) are pooled, concentrated under reduced pressure and treated with petroleum ether or hexane to recover a crude product (ii). Because this produce still includes impurities, it is further purified as follows. Thus, for exaple, this second purification process is carried out on a second silica gel column using a different solvent system.

The development is started with halogenated hydrocarbon such as dichloromethane or chloroform, followed by elution with solvent admixed with a polar solvent such as an alcohol (e.g. ethanol, methanol, etc.) or a ketone (e.g. acetone, methyl ethyl ketone, etc.) to recover the novel demethylmaytansinoid compound (III). The solvent systems for the first and the second silica gel column chromatography may be reversed in order and it is also possible to employ other suitable combinations of common organic solvents which are usually available.

When a macroporous adsorbent resin is employed for the purification of crude product (ii), the novel demethylmaytansinoid compound (III) may be separated by elution with a mixture of a lower alcohol, a lower ketone or an ester with water. As examples of the lower alcohols, there may be mentioned, among others methanol, ethanol, propanol and butanol and so on. The lower ketone may for example be acetone or methyl ethyl ketone. The ester may for example be ethyl acetate. Thus, by way of illustration, crude product (ii) is first dissolved in 50 V/V % aqueous methanol and adsorbed on a column of Piaion HP-10 (Mitsubishi Chemical Industries Ltd.). The column is then washed with 50 V/V % methanol, followed by elution with 90 V/V% aqueous methanol to obtain the desired novel demethylmaytansinoid compound (III).

The demethylmaytansinoid compound (III) thus obtained is concentrated under reduced pressure and crystallized from ethyl acetate. Alternatively, after the concentration, petroleum ether is added to the concentrate and the resulting powders are recovered.

Moreover, by deacylating the compound (V) which is a demethylmaytansinoid compound (III) wherein $R_1$ is an acyl group $R'_1$, there can be obtained a demethylmaytansinoid compound (VI).

Thus, deacylation of demethylmaytansinoid compound (V) gives a demethylmaytansinoid compound (VI) which is a compound (III) wherein $R_1$ is hydrogen. In this connection, since the acyl group is present in the β-position of the carbonyl group, the conventional reductive cleavage reaction procedure can be utilized with advantage. Thus, the compound (VI) can be obtained by the reductive cleavage of the O-ester bond in 3-position with use of a complex metal hydride compound [e.g. lithium aluminum hydride ($LiAlH_4$)] at a low temperature (e.g. $-20°$ to $0°$ C.) the reaction being thus accomplished without affecting the other functional groups such as carbonyl, epoxy, carbon-carbon double bond, etc. The compound (VI) can be isolated and purified by the procedure mentioned hereinbefore.

When the above demethylmaytansinoid compound (I) contains stereoisomerism in acyl group $R_1$ (e.g. D- and L-forms), the compound (I) encompasses such isomers and a mixture thereof. Generally, such an isomeric configuration may already be present in the starting compound (II) and, as will be described in detail, there are cases in which compound (II) has already been resolved into the component isomers during the process of its production by the per se conventional separatory procedure such as silica gel chromatography or high pressure liquid chromatography.

In the method of this invention, the isomeric relationship in compound (I) is in many cases identical with that in compound (II).

Moreover, when a mixture of such isomers is employed as the starting compound (II), the product compound (I) is obtained as a mixture of isomers. These isomers can be separated from each other generally by a procedure known per se, e.g. by silica gel chromatography.

The compound (I) according to this invention can be used as an antifungal, antiprotozoal and antitumour agent. Toxicity of the compound (I) is low.

The compound (I) can also be used as a intermediate for the synthesis of useful medicines.

A test on biological activity was performed on the compounds obtained in the Examples given hereinafter.

Biological Activity (A) Antimicrobial Activity

With trypticase-soy-agar medium (Baltimore Biologicals Limited, U.S.A.) as the assay medium, the minimal inhibitory concentrations of the compound (I) were assayed against the microorganisms mentioned below employing the paper disc method. Thus, on the plates of those microorganisms, the antibacterial activity of compound (I) was assayed with paper discs immersed with 0.02 ml of a 300 μg/ml solution of demethylmaytansinoid compound (I). (The paper discs supplied by Toyo Seisakusho, Japan, thin-type, 8 mm diam.). The results showed that the demethylmaytansinoid compound (I) was inactive against the following microorganisms. *Escherichia coli, Proteus vulgaris, Proteus mirabilis, Pseudomonas aeruginosa, Staphylococcus aureus, Bacillus subtilis, Bacillus cereus, Krebsiella pneumoniae, Serratia marcescens* and *Mycobacterium avium*.

On the other hand, on agar plates [3.5 g disodium hydrogen phosphate, 0.5 g monopotassium phosphate, 5 g of yeast extract (Difco), 10 g glucose, 15 g agar, 1000 ml distilled water, pH 7.0], the antifungal activity of the test compound was assayed against *Hamigera avellanea* IPO 7721 by the paper disc method. Thus, on the plates inoculated with the above microorganism, the zones of growth inhibition were determined using paper discs immersed with 0.02 ml of a 100 μg/ml solution of demethylmaytansinoid compound (I).

The results showed that the demethylmaytansinoid compound (I) inhibited growth of the said microorganism. The zones of growth inhibition by compound (I) are shown in Table 1.

Then, with *Tetrahymena pyriformis* W as the test organism and a medium composed of 20 g tryptose-peptone (Difco Co.), 1 g yeast extract, 2 g glucose, 1000 ml distilled water, 10 ml 1 M phosphate buffer (pH 7.0) as the assay medium, the microorganism was incubated at 28° C. for 44 to 48 hours and the growth inhibitory activity of demethylmaytansinoid compound (I) was assayed by the serial dilution method. The results showed that demethylmaytansinoid compound (I) was active against the test organism. The zones of growth inhibition and minimal inhibitory concentrations of compound (I) are shown in Table 1.

TABLE 1

| Test compound | Antifungal activity, (φ mm) Hamigera avellanea IFO 7721 | Antiprotozoan activity, MIC (μg/ml) Tetrahymena pyriformis W |
|---|---|---|
| 20-Demethoxy-20-hydroxy-maytansinol | <8 | 40 |
| 20-Demethoxy-20-hydroxy-maytanacine | 10 | 10 |
| 20-Demethoxy-20-hydroxy-maytansinol propionate | 15 | 2 to 4 |
| 20-Demethoxy-20-hydroxy-maytansinol 3-isobutyrate (PDM-3) | 21 | 2 |
| 20-Demethoxy-20-hydroxy-maytansinol 3-butyrate (PDM-3') | 21 | 2 |
| 20-Demethoxy-20-hydroxy-maytansinol 3-isovalerate (PDM-4) | 24 | 1 |
| 20-Demethoxy-20-hydroxy-maytansinol 3-hexanoate | 21 | 1 to 2 |
| 20-Demethoxy-20-hydroxy-maytansinol 3-cyclohexane-carboxylate | 20 | 1 to 2 |
| 20-Demethoxy-20-hydroxy-maytansinol 3-phenylacetate | 23 | 1 to 2 |
| 20-Demethoxy-20-hydroxy-maytansinol 3-p-chlorobenzoate | 10 | 4 |
| 20-Demethoxy-20-hydroxy-maytansinol 3-picolinate | 10 | ≧4 |
| 20-Demethoxy-20-hydroxy-maytansinol 3-N—phenylcarbamate | <8 | ≧8 |
| 20-Demethoxy-20-hydroxy-maytansine (L) | 19 | 2 to 4 |
| 20-Demethoxy-20-hydroxy-maytansine (L) | <8 | >16 |
| 20-Demethoxy-20-hydroxy-maytanprine (L) | 23 | 1 to 2 |
| 20-Demethoxy-20-hydroxy-maytanbutine (L) | 24 | 1 to 2 |
| 20-Demethoxy-20-hydroxy-maytanvaline (L) | 24 | 2 |
| 20-Demethoxy-20-hydroxy-dechloromaytansinol 3-isobutyrate | 16 | 4 to 8 |
| 20-Demethoxy-20-hydroxy-maytansinol 3-phenylacetate | 15 | 4 to 8 |

(B) Antitumour Activity

In a therapeutic test in mice into which P-388 tumor cells had been intraperitoneally transplanted, demethylmaytansinoid compound (I) administered intraperitoneally once daily for 9 consecutive days produced a definite prolongation of their life spans.

(C) Acute Toxicity

The acute toxicity test in mice by the intravenous route showed that demethylmaytansinoid compound (I) produced no death at all at the dose level of 1000 μg/kg.

Because demethylmaytansinoid compound (I) has thus strong growth-inhibitory activity against fungi and protozoa, it is useful as an antifungal or antiprotozoal agent. Moreover, since demethylmaytansinoid compound (I) has life-span extending activity in tumour-bearing mammalian animals (e.g. mouse), it is expected to be of value as an antitumour agent.

As an antifungal or antiprotozoal agent, demethylmaytansinoid compound (I) can be used with advantage for testing bacterial flora in samples of soil, active sludges or animal body fluids. Thus, when useful bacteria are to be isolated from soil samples or when the activity of bacteria to the exclusion of that of fungi is to be tested in the operation and analysis of an active sludge system for the disposal of waste water, compound (I) can be utilized to ensure selective growth of bacterial flora without permitting growth of the bacteria concomitantly present in the samples. By way of example, a test sample is added to a fluid or solid medium and 0.1 ml of a 10 to 100 μg/ml solution of maytansinoid compound (I) in 1% aqueous methanol is added per ml of the medium, followed by incubation.

Since the present compound (I) has life-span extending activity in for example mouse, it can also be used as an antitumor agent for treating tumor-bearing warm-blooded mammalian animals (e.g. mouse, rat, dog, cat).

As an antitumour agent, compound (I) according to this invention can be administered orally or by other routes. For administration by routes other than the oral route, injections are preferred. Thus, subcutaneous, intraperitoneal, intravenous and intramuscular injections, for instance, may be selectively employed. The dosage may range from 12.5 to 1000 μg, preferably from about 50 to about 800 μg per body weight per dose, although it may be increased or decreased according to the condition, animal species and other factors. Such an injection may be prepared, for example by dissolving about 500 μg to about 10 mg of compound (I) in about 0.5 ml of alcohol (e.g. methanol or ethanol) and making it up with a sufficient amount of physiological saline to make a total of 10 ml. When the dosage is small, this solution may be further diluted with physiological saline.

It has been found that the solubility of demethylmaytansinoid compound (I) in water is markedly higher.

In this specification, the compound of general formula (I) wherein $R_1 = -COCH(CH_3)_2$ and $X = Cl$ (i.e. 20-demethoxy-20-hydroxymaytansinol 3-isobutyrate) will hereinafter be referred to as PDM-3, the compound (I) in which $R_1 = -CO(CH_2)_2-CH_3$ and $X = Cl$ (i.e. 20-demethoxy-20-hydroxymaytansinol 3-butyrate) will be referred to as PDM-3', and the compound (I) in which $R_1 = -COCH_2-CH(CH_3)_2$ and $X = Cl$ (i.e. 20-demethoxy-20-hydroxymaytansinol 3-isovalerate) will be referred to as PDM-4.

The starting compound (II) wherein $R_1 = -CO-CH(CH_3)_2$ and $X = Cl$ will be called ansamitocin P-3, the compound (II) wherein $R_1 = -CO(CH_2)_2-CH_3$ and $X = Cl$ will be referred to as ansamitocin P-3' and the compound (II) wherein $R_1 = -COCH_2-CH(CH_3)_2$ and $X = Cl$ will be referred to as ansamitocin P-4.

The starting compound (II) may be one of the known maytansines, ansamitocins and other compounds. The maytansine compounds are described for example in U.S. Pat. No. 3,896,111. Maytanacine and maytansinol propionate can also be produced by a manner described in Journal of the American Chemical Society 97, 5294(1975) or by growing Nocardia sp. No.C-15003 (FEPM-P No.3992, IFO 13726, ATCC-31281) in a culture medium and isolating the metabolite from the culture broth. (See Japanese Patent Application Laid-Open No.121998/1978, laid open Oct. 24, 1978; Patent Application in the Federal Republic of Germany Laid-open as Offenlegungsschrift No. 2746 253 on Oct. 5, 1978). Ansamitocin P-3, ansamitocin P-3' and ansamitocin P-4 can be produced by cultivating the above-mentioned Nocardia sp. No.C-15003 (see Japanese Patent Application Laid-open No.130693/1978, laid open Nov. 14, 1979; Patent Application in the Federal Republic of German Laid-open as Offenlegungsschrift 2746 209, laid open Oct. 9, 1979.).

The compound (II) can also be produced by acylating maytansinol or dechloromaytansinol with a carboxylic acid of the formula $R_1OH$ [wherein $R_1$ is as previously defined] or a reactive derivative with respect to carboxyl function of said carboxylic acid.

Maytansinol, which is used for the production of compound (II), is a compound known as a plant principle [Kupchan et al., J. Amer. Chem. Soc. 97, 5294(1975)], which can also be obtained by the reductive cleavage of a maytansine compounds.

Moreover, maytansinol can also be produced by the steps of growing Nocardia sp. No.C-15003 (FERM-p No.3992, IFO 13726, ATCC-31281) in a culture medium to obtain maytanacine, maytansinol propionate or ansamitocins of the formula:

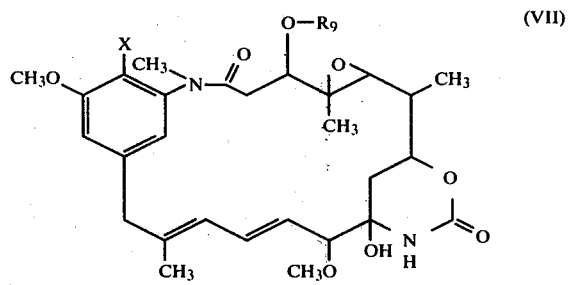

(wherein $R_9$ is acetyl, propionyl, iso-butyryl, n-butyryl or isovaleryl) and subjecting the same metabolite to a reductive ester cleavage reaction with a metal hydride compound, e.g. LiAlH$_4$ [see Nature Vol.270, 721(1977), or Japanese patent application Laid-open No.130693/1978; patent application in the Federal Republic of Germany Laid-open as Offenlegungschrift 2746 209].

Pechloromaytansinol can be produced by the reduction of compound (II) in which X is Cl with a metal hydride compound. The metal hydride compound is preferably a metal complex such as lithium aluminum hydride (LiAlH$_4$), which is used normally in the amount of about 1 to 25 moles, preferably of about 4 to 10 moles per mole of starting compound (II) (X=Cl). Normally this reduction is preferably conducted in a solvent which may for example be an ether (e.g. diethylether, tetrahydrofuran, etc.) and, preferably, tetrahydrofuran. The reaction can be carried out normally at about −70° C. to about +80° C. and preferably at about −40° C. to about +20° C. In many cases, this reaction gives rise to a compound corresponding to compound (II) (X=Cl) but its 3-acyl group of which has been removed, that is to say maytansinol, as a by-product. After the reduction, the excess reducing agent is destroyed, e.g. by the addition of water, acetic acid or ethyl acetate, and after the reaction mixture is made acidic, it is extracted with a suitable solvent (e.g. ethyl acetate). The resulting crude product is purified, for example by silica gel chromatography or high-pressure liquid chromatography, whereby the desired dechloromaytansinol is obtained.

The starting material maytansinoid compound (II) wherein R$_1$ is acyl, i.e. the compound of formula (II):

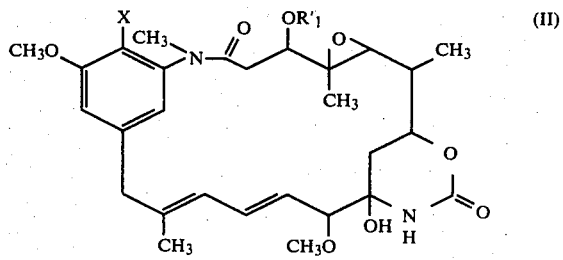
(II)

(wherein X and R$_1'$ have the meanings respectively defined hereinbefore) can be produced by reacting maytansinol or dechloromaytansinol with a carboxylic acid of formula:

R$'_1$—OH    (VIII)

(wherein R$'_1$ is as defined hereinbefore) or a reactive derivative with respect to carboxyl function of the same carboxylic acid.

The above acylation may be effected, for example by reacting maytansinol or dechloromaytansinol with carboxylic acid (VIII) in the presence of a carbodiimide.

The carboxylic acid (VIII) may be used in a proportion of about 1 to 500 mole equivalents based on maytansinol or dechloromaytansinol and, in many cases, is preferably used in a proportion of about 1 to 30 mole equivalents on the same basis. The carbodiimide may be used in an amount of about 1 to 700 mole equivalents based on maytansinol or dechloromaytansinol and, in many cases, is preferably used in an amount of about 1 to 50 mole equivalents on the same basis. The carbodiimide is a compound containing a carbodiimide linkage (—N=C=N—) which will be transformed into a urea bond (—NH—CO—NH—) during the acylation reaction. Thus, it may be a compound of formula (IX):

R$_{10}$—N=C=N—R$_{11}$    (IX)

(wherein R$_{10}$ and R$_{11}$ are organic residues which are capable of permitting the conversion of the carbodiimide linkage into a urea linkage).

As the organic residues R$_{10}$ and R$_{11}$, there may be mentioned cycloalkyl groups having or not having di-lower (C$_{1-6}$; the same applies hereinafter) alkylamino groups, lower alkyl groups having or not having di-lower alkylamino or morpholino groups and phenyl having or not having lower alkyl groups. As the carbodiimides, there may be mentioned dicyclohexylcarbodiimide being practically preferable. Thus, diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide and 1-ethyl-3-(3-diamethylaminopropyl)carbodiimide may be mentioned by way of example.

The acylation reaction may be carried out in the presence of a suitable solvent. As examples of such solvent there may be mentioned esters (e.g. ethyl acetate), ethers (e.g. diethyl ether, dioxane, tetrahydrofuran, etc.), halogenated hydrocarbons (e.g. methylene chloride, chloroform, etc.), nitriles (e.g. acetonitrile), aromatic hydrocarbons (e.g. benzene), nitromethane, pyridine, dimethylformamide, dimethylsulfoxide, sulforane and various suitable mixtures thereof.

Normally this acylation can be conducted at a suitable temperature from a temperature under ice cooling to the reflux temperature of the reaction system.

The acylation reaction can be conducted more advantageously in the presence of a catalyst which will promote the acylation of maytansinol or dechloromaytansinol. The catalyst may for example be a base catalyst or an acid catalyst. As examples of the base catalyst there may be mentioned tertiary amines [such as aliphatic tertiary amines (e.g. triethylamine, etc.) and aromatic amines (e.g. pyridine, α-, β- or γ-picoline, 2,6-lutidine, 4-dimethylaminopyridine, 4-pyrrolidinopyridine, dimethylaniline, diethylaniline, etc.)], alkali metal halides (e.g. potassium fluoride, anhydrous potassium iodide, etc.), salts of organic acids (e.g. sodium acetate, etc.) and so on. As examples of the acid catalyst there may be mentioned Lewis acids [e.g. anhydrous zinc chloride, anhydrous aluminum chloride (AlCl$_3$), anhydrous ferric chloride, titanium tetrachloride (TiCl$_4$), stannous tetrachloride (SnCl$_4$), antimony pentachloride, cobalt chloride, cupric chloride, boron trifluoride ethoxide, etc.], inorganic strong acids (e.g. sulfuric acid, perchloric acid, hydrogen chloride, hydrogen bromide, etc.), organic strong acids (e.g. benzenesulfonic acid, p-toluenesulfonic acid, trifluoroacetic acid, trichloroacetic acid, etc.), acidic ion exchange resins (e.g. polystyrene-sulfonic acid] and so on. When a carboxylic acid (VIII) having an acyl group R$'_1$ of the formula —CO—R$_2$ [where R$_2$ is as previously defined] is employed in the reaction, it is generally preferable that, as said catalyst, 4-dimethylaminopyridine or 4-pyrrolidino-pyridine or the like be employed. When a carboxylic acid (VIII) having an N-acyl-α-aminoacyl group (R$'_1$) of the formula:

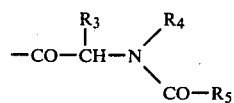

are as previously defined), which is among said acyl groups, is employed, anhydrous zinc chloride is a preferred catalyst.

The catalyst may be employed in a catalytic amount which will be sufficient to promote the acylation of maytansinol or dechloromaytansinol with carboxylic acid (VIII). Thus, it is used normally in the range of about 0.001 to 10 mole equivalents and preferably in the range of about 0.01 to 1 mole equivalents based on carboxylic acid (VIII). The use of such a catalyst often leads to marked increases in the yield of maytansinoid compound (II). It also helps save on the amount of carboxylic acid (VIII). Thus, the requirement of carboxylic acid (VIII) may often be reduced to about 1 to 10 mole equivalents based on maytansinol or dechloromaytansinol.

When isomerism exists in the carboxylic acid (VIII), e.g. one having an N-acyl-α-aminoacyl group 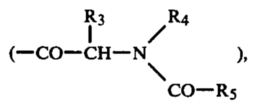 such isomers (e.g. D- or L-form) of carboxylic acid (VIII) may be employed either severally or as a mixture of optional proportions.

When an optically active acyl group is to be introduced into the 3-hydroxy function of maytansinol or dechloromaytansinol, it is sometimes useful to employ the corresponding optical isomer of carboxylic acid (VIII). At other times, the use of an optically active carboxylic acid (VIII) may yield maytansinoid compound (II) as a mixture of D- and L-isomer.

The acylation reaction with said reactive derivative of carboxylic acid (VIII) may for example be conducted using a derivative containing a functional group which is able to acylate the 3-position of maytansinol or dechloromaytansinol, e.g. an acid anhydride of carboxylic acid (VIII). The solvent and catalyst may be the same as those mentioned in connection with the acylation reaction in the presence of a carbodiimide compound. The reaction temperature is normally about −20° C. to 100° C. and preferably about 20° to 40° C., although the reaction may be conducted at a higher temperature in order to hasten the reaction.

The starting compound (II) in which $R'_1$ is 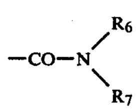 (where $R_6$ and $R_7$ have the meanings respectively defined hereinbefore) can be produced, for example, by carbamoylating maytansinol or dechloromaytansinol.

This carbamoylation may be effected, for example, by reacting maytansinol or dechloromaytansinol with a carbamic acid halide (X) of the formula:

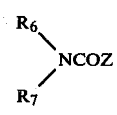

(X)

(wherein $R_6$ and $R_7$ have the meanings respectively defined hereinbefore) in the presence of a base. Referring to the above formula (X), halogen Z may for example be chlorine or bromine. As examples of the base just mentioned, there may be cited alkali metals (e.g. lithium, sodium, etc.) and alkali metal alkyls (e.g. n-butyllithium, sec-butyllithium, phenyllithium, naphthalenelithium, sodium methylsulfinylmethid, etc.). Particularly desirable is n-butyllithium.

The reaction is conducted in a solvent. As examples of the solvent, there may be mentioned ethers (e.g. tetrahydrofuran, dimethylether, diethyl ether, etc.), aromatic hydrocarbons (e.g. toluene, xylene, etc.) and suitable mixtures of such solvents, although tetrahydrofuran is the most versatile. To conduct the reaction, maytansinol or dechloromaytansinol is dissolved in such a solvent and, after the addition of said alkali metal compound, a carbamic acid halide of formula (X) is added. The alkali metal compound is desirably employed in a proportion of 3 to 10 mole equivalents and, for still better results, about 4 to 6 equivalents based on maytansinol or dechloromaytansinol. The carbamic halide is used in a proportion of 2 to 10 mole equivalents and, preferably, 3 to 5.5 equivalents on the same basis.

The reaction may be carried out at a suitable temperature within the range of −78° to +50° C., although it is normally preferable to conduct the reaction between 330° to +40° C.

After the reaction has been completed, the reaction product, as it is or after neutralization with dilute aqueous acid or after removal of the solvent by distillation, if necessary, can be isolated by conventional procedures as will be determined hereinafter. This reaction may in certain cases be conducted with a reactive derivative, with respect of the carboxyl function, of carbamic acid other than said carbamic acid halide.

An alternative carbamation procedure comprises reacting maytansinol or dechloromaytansinol with a compound (XI) of the formula:

$$R_6-N=C=O \qquad (XI)$$

(wherein $R_6$ has the same meaning as defined hereinbefore). This reaction procedure yields a maytansinoid compound (II) in which $R_7$ is hydrogen. This reaction is preferably conducted in solution. The solvent may be practically any solvent free from active hydrogen (e.g. the hydrogen atom of —OH or —NH—) which is reactive to compound (XI). Thus, examples of the solvent are ethers (e.g. diethyl ether, dimethoxyethane, dioxane, tetrahydrofurane, etc.), halogenated hydrocarbons (e.g. dichloromethane, chloroform, carbon tetrachloride, 1,2-dichloroethane, etc.), aromatic hydrocarbons (e.g. benzene, toluene, xylene, chlorobenzene, etc.), nitriles (e.g. acetonitrile, propionitrile, etc.) and esters (e.g. ethyl acetate, etc.) as well as suitable mixtures of such solvents may be employed. Such a solvent is desirably as dry as possible.

The amount of compound (XI) necessary for the reaction is about equivalent relative to maytansinol or dechloromaytansinol. However, it is desirable to employ an excess of compound (XI), for it may be partially consumed by the water contained in the solvent and, in certain cases, by the dimerization or other reaction of compound (XI) which per se is reactive. Thus, it is normally advisable to employ 2 to 20 mole equivalents and, preferably 2 to 5 equivalents. The reaction may be conducted at −20° to +80° C. and, preferably, at 5° to 40° C. In the case of reactive compound (XI) (normally compounds having nitro or polyhalogen substituents), it may be simply admixed with the mating compound. The use of a catalyst is normally desirable, however. As examples of the catalyst there may be mentioned the catalysts commonly employed in the carbamoylation of alcohols or phenols with isocyanic acid esters, e.g. bases e.g. tertiary amines (e.g. triethylamine, pyridine, etc.), alkalimetal alkoxides (e.g. potassium tert-butoxide, sodium methoxide, etc), alkali metal acetates (e.g. the acetates of lithium, sodium, potassium, rubidium and cesium), metal salts (e.g. chlorides and organic carboxylates of lead, bismuth, tin, cobalt, zinc, cadmium, manganese, titanium, iron, copper, etc.), metal complexes or organometallic compounds (e.g. 2,4-pentadiene-metal complexes, ferrocenes, dibutyltin oxide, dioctyltin oxide, dibutyltin dilaurate). Among these, anhydrous zinc chloride is used as especially suited catalyst for the reaction from the viewpoints of selectivity, reaction rate and so on. The catalyst is used in an amount sufficient to accelerate the reaction, and generally an amount of about 0.01 to about 10 moles, preferably about 0.1 to about 3 moles, per mole of compound (XI) is sufficient.

When cuprous chloride is used as the catalyst mentioned above, for example, there may be formed compounds of the formula

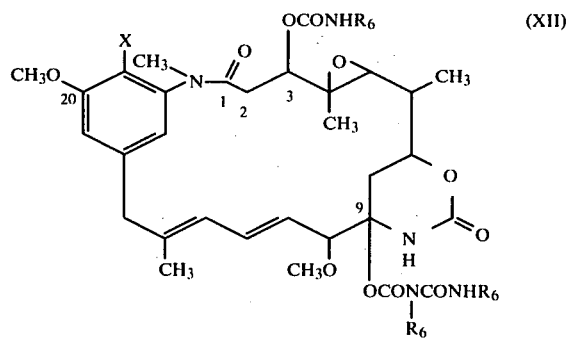

wherein X and $R_6$, have the same meaning as above. These compounds (XII), however can be easily converted into compounds (II) which have a hydrogen atom instead of

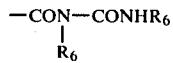

at position 9 by treatment with an acid. Acids usable for this reaction include mineral acids (e.g. hydrogen chloride, hydrochloric acid, sulfuric acid, phosphoric acid, etc.), organic strong acids (e.g. benzenesulfonic toluenesulfonic, methanesulfonic, trifluoroacetic and trichloroacetic acid, etc.) and so on. Trifluoroacetic acid is preferred among others, however. Preferably the reaction is carried out in the state of a solution, and the solvent may be the same one as is used in the carbamoylation of compound (XI) above. Generally this reaction proceeds rapidly at a temperature of about −20° C. to about 40° C. This reaction sometimes can also be effected only by passing the reaction mixture of carbamoylation containing compound (XII) through a silica gel column.

The starting compound (II) in which $R_1$ or $R'_1$ is —CO—O—$R_8$ [wherein $R_8$ has the same meaning defined hereinbefore] can be produced by allowing maytansinol or dechloromaytansinol to react with halogenocarbonic esters of the formula:

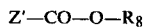

(wherein $R_8$ has the same meaning as defined hereinbefore, and Z' is halogen) in the presence of a base. As examples of halogen, there may be mentioned chlorine and bromine.

The reaction is conducted in any of the solvents exemplified for said carbamoylation.

As the base, any of the bases exemplified for carbamoylation can be employed. The base is desirably employed in a proportion of about 3 to 20 mole equivalents and, for still better results, about 4 to 10 mole equivalents based on maytansinol or dechloromaytansinol. The halogenocarbonic ester is used in a proportion of about 3 to 20 mole equivalents and, preferably, about 5 to 10 mole equivalents on the same basis. The reaction may be carried out at a suitable temperature within the range of −78° to +50° C., although it is normally to conduct the reaction between −30° to +40° C., preferably −20° to +30° C.

The maytansinoid compounds (II) of the invention produced by the above methods can be isolated and collected from the reaction mixtures by conventional methods, e.g. by appropriately applying such methods as concentration, solvent extraction, chromatography, recrystallization, etc. When compounds (II) are produced in the form of a mixture of isomers (e.g. D- and L-isomers), these isomers can generally be separated from each other by separating means known per se, e.g. by silica gel column chromatography. The maytansinoid compounds (II) of the present invention include these individual isomers as well as mixtures thereof.

The following Reference Examples and Examples are further illustrative of this invention but should not be considered to be limitative of the scope of the invention, wherein "percent (%)" is based on "weight/volume" unless otherwise noted. In the following Examples, "demethyl" stands for the abbreviation of "20-demethoxy-20-hydroxy".

REFERENCE EXAMPLE 1

In 5 ml of dry dichloroethane was dissolved 99.6 mg. (0.176 m mole) of maytansinol, followed by the addition of 377.2 mg. (1.76 m moles) of hexanoic anhydride (caproic anhydride) and 43.5 mg (0.366 m mole) of p-dimethylaminopyridine (DMAP). The mixture was stirred at room temperature (ca. 23° C.) for 6 hours, at the end of which 30.5 mg. (0.25 m mole) of DMAP was further added. The mixture was stirred at room temperature for an additional 18 hours. To the reaction mixture were added 5 ml of 1 N-HCl and 5 ml of water and the organic layer was taken, washed with 10% aqueous sodium hydrogen carbonate (10 ml) and dried over anhydrous sodium sulfate. The solvent was distilled off and the residue was chromatographed on a column of silica gel (75 g) with ethyl acetate (ca. 250 ml) and, then, with ethyl acetate/ethyl acetate saturated with water=2:1 (V/V) (ca. 900 ml). The eluate was collected in 16 g. fractions and fractions No.13 through No.30 were pooled and concentrated to remove the solvent, whereby 3.0 mg. of crude product was obtained. This residue was dissolved in ethyl acetate and after the addition of ether, a white powdery solid was recovered by filtration. By the above procedure there was obtained 34.3 mg. of maytansinol 3-hexanoate, m.p. 159°-162° C. (decomp.)

REFERENCE EXAMPLE 2

In 1.0 ml of dichloromethane was dissolved 23.5 mg. of maytansinol, and at about 22° C., 70.5 mg (ca. 10 m moles) of acetic-formic anhydride (prepared by cooling 2 ml. of acetic anhydride, adding 1 ml of 99% formic acid under stirring over ca. 10 minutes at −5° to 0° C., heating the mixture at 50° C. for 15 minutes and quenching it at 0° C.) and 11.7 mg of DMAP were added. The mixture was stirred at room temperature (ca. 22° C.) overnight. To this reaction mixture was added 10 drops of methanol and, after stirring for 3 hours, the mixture was concentrated to dryness under reduced pressure. The residue was spotted on a silica gel preparative TLC and developed twice with ethyl acetate saturated with water. The silica gel in the zone about 6.0 to 8.0 cm above the base line was scrapped up and extracted with 10% methanol-dichloromethane. The solvent was then distilled off under reduced pressure to recover 8.35 mg. of maytansinol 3-formate as a colorless glassy residue.

REFERENCE EXAMPLE 3

By the similar procedure as that described in Reference Example 1 or 2, the following compounds can be prepared.
(A) From maytansinol and octanoic anhydride (caprylic anhydride, there is obtained maytansinol 3-octanoate as a white sandy solid melting at 151°–160° C.(decomp.).
(B) From maytansinol and decanoic acid (capric acid), there is obtained maytansinol 3-decanoate as a white sandy solid melting at 130°–134° C.(decomp.).
(C) From maytansinol and heptanoic acid, there is obtained maytansinol 3-heptanoate, m.p. 158°–160° C.(decomp.).
(D) From maytansinol and tridecanoic acid, there is obtained maytansinol 3-tridecanoate, m.p. 110°–116° C.(decomp.).
(E) From maytansinol and hexadecanoic acid (palmitic acid), there is obtained maytansinol 3-hexadecanoate as a white powder melting at 105°–116° C.(decomp.).
(F) From maytansinol and valeric anhydride, there is obtained maytansinol 3-valerate, m.p. 165°–168° C.

REFERENCE EXAMPLE 4

To a mixed solution of maytansinol (103.2 mg. 0.183 m mole) and cyclohexanecarboxylic acid (140 mg, 1.094 m moles) in 5 ml of dry dichloromethane was added DCC (267 mg, 1.296 m moles), and after stirring at room temperature for a short while until insolubles began to separate out, DMAP (50.8 mg, 0.416 m mole) was added. The mixture was stirred at room temperature overnight. Then, the insolubles were filtered off, the filtrate washed with 0.5 N-HCl(ca. 10 ml) and saturated aqueous sodium hydrogen carbonate (ca. 10 ml) in that order, and dried over anhydrous sodium sulfate. The solvent was distilled off and the residue was chromatographed on a column of silica gel (75 g.). Elution was carried out with ethyl acetate, the eluate being collected in 16 g. fractions, and fractions No.14 through No.30 were pooled and concentrated to remove the solvent, whereupon 59 mg of crude product was obtained. This crude product was dissolved in ethyl acetate, followed by addition of diethyl ether. By the above procedure there was obtained 24.3 mg of maytansinol 3-cyclohexanecarboxylate as crystals melting at 202°–206° C.(decomp.).

REFERENCE EXAMPLE 5

The following compounds can be produced by similar procedure as that described in Reference Example 4.

(A) From maytansinol and cyclopropanecarboxylic acid, there is obtained maytansinol 3-cyclopropanecarboxylate, m.p. 182°–187° C.(decomp.).
(B) From maytansinol and phenylacetic acid, there is obtained maytansinol 3-phenylacetate, m.p. 180°–182° C.(decomp.).
(C) From maytansinol and benzoic acid, there is obtained maytansinol 3-benzoate, m.p. 174°–177° C.(decomp.).
(D) From maytansinol and p-chlorobenzoic acid, there is obtained maytansinol and 3-p-chlorobenzoate, m.p. 178°–183° C.(decomp.).
(E) From meytansinol and 2-furancarboxylic acid, there is obtained maytansinol 3-(2-furan)carboxylate, m.p. 180°–189° C.(decomp.).
(F) From maytansinol and phenylproponic acid, there is obtained maytansinol 3-phenylpropionate, m.p. 160°–163° C.(decomp.).
(G) From maytansinol and nicotinic acid, there is obtained maytansinol 3-nicotinate as a white powder melting at 184°–187° C.(decomp.).
(H) From maytansinol and picolinic acid, there is obtained maytansinol 3-picolinate, m.p. 190°–193° C.(decomp.).
(I) From maytansinol and isonicotinic acid, there is obtained maytansinol 3-isonicotinate as white crystals melting at 185°–187° C.(decomp.).
(J) From maytansinol and N-acetyl-L-proline, there is obtained maytansinol 3-(N-acetyl)-L-prolinate, both as white crystals melting at 195°–198° C.(decomp.) and as a glassy product with an UV spectrum ($\lambda_{max-MeOH}$) nm: 233, 244, 253, 282 and 292.
(K) From maytansinol and 2-thiophenecarboxylic acid, there is obtained maytansinol 3-(2-thiophene)carboxylate as a glassy solid melting at 161°–163° C.(decomp.).

REFERENCE EXAMPLE 6

In 800 ml of dry tetrahydrofuran (THF) was dissolved 15.0 g of antibiotic ansamitocin mixture (ansamitocin P-2=12%; ansamitocin P-3=71%; ansamitocin P-4=17%) and, in dry nitrogen gas streams, the solution was chilled to −50° C. in a Dry-Ice-ethanol bath. Then, 13.0 g of lithium aluminum hydride (LAH) was added at one time and the mixture was stirred at −50° C. to −22° C. for 2 hours. The mixture was cooled to −28° C. and an additional 3 g. of LAH was added. The mixture was stirred at −28° C. to −22° C. for 80 minutes, followed by cooling again to −50° C. Thereafter, 750 ml of 2 N-HCl was carefully added dropwise over 30 minutes. The reaction mixture was extracted three times with 2.6 l, 1.6 l and 0.8 l portions of ethyl acetate and the extracts were combined, washed with saturated aqueous sodium chloride (100 ml×2) and dried (250 g MgSO$_4$). The solvent was distilled off under reduced pressure and the residue (13.6 g) was chromatographed on a column of silica gel (1.2 kg), elution being carried out with ethyl acetate/water=98.5:1.5 (V/V). The eluate was collected in 400 g fractions and fractions No.35 through No.52 were pooled. The solvent was distilled off and the residue was dried in vacuo to recover 7.25 g of maytansinol. Then, by the same procedure, there was obtained 1.55 g of an approximately equimolar mixture of maytansinol and dechloromaytansinol from fractions No.53 through No.68. Similarly, 0.78 g of dechloromaytansinol was recovered from fractions No.69 through No.86. Recrystallization from chloroform-hexane yielded 0.71 g of dechloromaytansinol as a white powder. m.p. 174°–179° C.(decomp.).

REFERENCE EXAMPLE 7

In 15 ml of dry dichloromethane was dissolved 100.0 mg (0.189 m mole) of dechloromaytansinol, followed by the addition of 69 mg (0.476 m mole) of N-acetyl-N-methyl-L-alanine, 117 mg (0.568 m mole) of DCC and 39 mg (0.287 m mole) of anhydrous zinc chloride in the order mentioned. The mixture was stirred at room temperature (ca. 23° C.) for 30 minutes, after which 55 mg (0.379 m mole) of N-acetyl-N-methyl-L-alanine, 98 mg (0.476 m mole) of DCC and 31 mg (0.228 m mole) of anhydrous zinc chloride were further added. The mixture was stirred again at room temperature for 2 hours. The insolubles were filtered off, the filtrate was concentrated to dryness and the residue was dissolved in about 5 ml of ethyl acetate and chromatographed on a column of silica gel (25 mm out. dia.×500 mm). Elution was carried out with ethyl acetate/ethyl acetate saturated with water=2:1 (V/V) and ethyl acetate saturated with water in that order and the eluate was collected in 15 g fractions. Fractions No.55 through No.103 were pooled and the solvent was distilled off, whereupon 53 mg crude dechloromaytansine was obtained. This residue was dissolved in ethyl acetate, diethyl ether was added, followed by cooling. By the above procedure there was obtained 24 mg of L-dechloromaytansine as colorless crystals. m.p. 184°–186° C. (decomp.)

The chromatographic fractions No.168 through No.221 were pooled and the solvent was distilled of to recover 65 mg of D-dechloromaytansine. This residue was dissolved in chloroform, diethyl ether added, and the resulting crystals are recovered by filtration. By the above procedure there was obtained 21 mg of D-dechloromaytansine as colorless microcrystals. m.p. 175°–178° C.(decomp.).

REFERENCE EXAMPLE 8

The following compounds can be produced in the similar manner as Reference Example 7.
(A) From dechloromaytansinol and isobutyric anhydride, there is obtained dechloromaytansinol 3-isobutyrate as white prisms melting at 250°–252° C.(decomp.).
(B) From dechloromaytansinol and nicotinic acid, there is obtained dechloromaytansinol 3-nicotinate, m.p. 170°–173° C. (decomp.).
(C) From dechloromaytansinol and cyclohexanecarboxylic acid, there is obtained dechloromaytansinol 3-cyclohexanecarboxylate, m.p. 217°–220° C.(decomp.).
(D) From dechloromaytansinol and phenylacetic acid, there is obtained dechloromaytanisol 3-phenylacetate, m.p. 165°–170° C.(decomp).

REFERENCE EXAMPLE 9

In 30 ml of dry dichloromethane was dissolved 150.0 mg (0.265 m mole) of maytansinol, followed by the addition of 24.0 mg (0.663 m mole) of N-acetyl-N-methyl-L-leucine and 174.2 mg (0.846 m mole) of DCC. The mixture was stirred at room temperature for a while, after which 46 mg (0.338 m mole) of anhydrous zinc chloride was added. After mixing at room temperature for 30 minutes, an additional 46 mg of anhydrous zinc chloride was added and stirred at the same temperature for about 45 minutes. Then, 104.3 mg (0.558 m mole) of N-acetyl-N-methyl-L-leucine, 141 mg (0.686 m mole) of DCC and 46 mg of anhydrous zinc chloride were further added, followed by stirring at that temperature for another 2.5 hours. The reaction mixture was washed with water, the organic layer dried over $Na_2SO_4$ and the solvent distilled off. The residue was chromatographed on a column of silica gel (75 g.) and elution was carried out with ethyl acetate (ca. 600 ml) and ethyl acetate saturated with water in that order, the eluate being collected in 17 g fractions. Fractions No.14 through No.34 were pooled, the solvent distilled off and the residue (100 mg) was rechromatographed on a column of silica gel (35 g) (solvent system: chloroform/methanol=60:1 (V/V), the eluate being collected in 25 g fractions. Fractions No.16 through No.30 were pooled, the solvent distilled off and the residue dissolved in ethyl acetate. After cooling, the resultant crystals were recovered by filtration. By this procedure there was obtained 89 mg of compound A. The initial chromatographic Fractions No.35 through No.56 were pooled, the solvent distilled off and the residue rechromatographed on silica gel (40 g [solvent system: chloroform/methanol=60:1(V/V) (ca. 200 ml), do. 40:1 (1 l)], the eluate being collected in 25 g fractions. Fractions No.17 through No.35 were pooled, the solvent distilled off, the residue dissolved in ethyl acetate and, after addition of diethyl ether, the precipitate recovered by filtration. By this procedure, there was obtained 52 mg of compound B.

Both compounds A and B are the desired compounds and, based on the following physical data, are considered to be maytansinol 3-(N-acetyl-N-methyl)-L-leucine ester and maytansinol 3-(N-acetyl-N-methyl)-D-leucine ester, respectively.

Compound A: m.p. 172°–175° C.(decomp.)
Compound B: m.p. 157°–159° C.(decomp.)

REFERENCE EXAMPLE 10

The following compounds can be produced in the same manner as Reference Example 9.
(A) From maytansinol and N-acetyl-N-benzyl-D-alanine, there is obtained two maytansinol 3-(N-acetyl-N-benzyl) alamine esters only dissimilar with respect to the stereochemical arrangement of the 2'-substituent. m.p. 174°–177° C.(decomp.); 163°–166° C.(decomp.)
(B) From maytansinol and N-acetyl-N-methyl-L-phenylalanine, there are obtained two maytansinol 3-(N-acetyl-N-methyl)phenylalanine esters only dissimilar with respect to the stereochemical arrangement of the 2'-substituent. m.p. 189°–193° C.(decomp.); 212°–214° C.(decomp.)
(C) From maytansinol and N-tert-butoxycarbonyl-N-methyl-L-alanine, there are obtained maytansinol 3-(N-tert-butyloxycarbonyl-N-methyl-L-alanine) ester [UV spectrum ($\lambda_{max}^{MeOH}$)nm: 234, 244, 254, 282, 290)] and maytansinol 3-(N-tert-butyloxycarbonyl-N-methyl-D-alanine)ester [UV spectrum ($\lambda_{max}^{MeOH}$)nm: 234, 241(sh), 253.5, 282, 290.]
(D) From maytansinol and N-acetylsacrosine, there is obtained maytansinol 3-(N-acetyl)sacrosine ester as a glassy product.

NMR spectrum (CDCl$_3$) δ ppm: 0.87(3H, s), 1.28(3H, d, J=5 Hz), 1.68(3H, s), 2.14(3H, s), 2.19(1H, dd, J=3 Hz & 14 Hz), 2.55(1H, dd, J=11 Hz & 14 Hz), 2.76(1H, d, J=9 Hz), 3.07(2H, s), 3.13(3H, s), 3.18(3H, s), 3.35(3H, s), 3.47(1H, d, J=9 Hz), 3.52(1H, d, J=13 Hz), 3.98(3H,s), 4.18(1H, m), 4.92(1H, dd, J=3 Hz & 11 Hz), 5.74(1H, dd, J=9 Hz & 15 Hz), 6.18(1H, d, J=11 Hz), 6.44(1H, dd, J=11 Hz & 15 Hz), 6.53(1H, s), 6.82(2H, s), etc.

(E) From maytansinol and N-acetylglycine, there is obtained maytansinol 3-(N-acetyl)-glycine ester, m.p. 189°–192° C.(decomp.).

REFERENCE EXAMPLE 11

In 80 ml of dichloromethane were dissolved maytansinol (300 mg, 0.5315 m mole) and N-acetyl-N-methyl-L-alanine (1.585 g, 10.62 m moles), followed by the addition of 3.285 g of dicyclohexylcarbodiimide and 72.5 mg (0.532 m mole) of anhydrous zinc chloride. The mixture was stirred at about 20° C. for 6 hours and, then, allowed to stand at that temperature for 11 hours. Then, N-acetyl-N-methyl-L-alanine (530 mg), dicyclohexylcarbodiimide (1095 mg) and anhydrous zinc chloride (150 mg) were further added. After 2 hours, the reaction mixture was filtered and the filtrate was washed with about 150 ml of water and dried over anhydrous sodium sulfate. The insolubles were filtered off and the filtrate was chromatographed on a column of silica gel (60 g), elution being carried out with chloroform/methanol=40:1(V/V). After the forerun was discarded, the eluate was collected in 25 g fractions.

Fractions No.14 through No.25 were pooled, concentrated and rechromatographed on silica gel (65 g), elution being carried out with ethyl acetate/ethyl acetate saturated with water=2:1(V/V). The forerun was discarded and the subsequent eluate was collected in 16 g fractions. Fractions No.25 through No.60 yielded 149.3 mg of compound A. The rechromatographic fractions Nos.23 and 24 and Nos.61 through 100 were pooled and concentrated to dryness to recover 20.5 mg of product. This product was subjected to preparative silica gel TLC (Kieselgel 60F$_{254}$, Art. 5717, Merck) and the chromatogram was developed with 10% isopropyl alcohol-chloroform to recover an additional 6.3 mg of Compound A. The above rechromatographic fractions No.101 through No.105 were also pooled and concentrated to obtain 320 mg of product. This product was rechromatographed on a column of silica gel (75 g) (solvent system: chloroform/methanol=40:1 (V/V)) to recover 95.7 mg of compound B which was an isomer of compound A.

The total yield of compound A was 155.6 mg and that of compound B was 95.7 mg.

Compound A was identified with maytansine (L-form) obtained from the plant by comparison of the following data with the data on maytansine obtained from the plant as given in Journal of Organic Chemistry 42, No.14, 2349–2357(1977). UV spectrum (λmax, EtOH) nm: 289, 281, 254, 242(sh.), 233 Mass spectrum (m/e): 691, 630, 485, 470, 450, 128, 100, 58 $[\alpha]_D^{23}$ −136°±30° (c=0.055, CHCl$_3$)

Compound A was dissolved in a mixture of ethyl acetate and diethyl ether and allowed to stand, whereupon crystals were separated out. These crystals were recrystallized once from ethyl acetate-diethyl ether and, then, twice from dichloromethane-diethyl ether. By the above procedure there was obtained compound A as colourless plates melting at 191°–195° C.(decomp.).

Compound B was identified with an isomer of maytansine and assumed to be D-maytansine by comparison of the following data with the data on maytansine.

UV spectrum (λmax, EtOH) nm: 289, 281, 253, 240(sh.), 233 Mass spectrum (m/e): 691, 630, 485, 470, 450, 128, 100, 58 $[\alpha]_D^{23}$ −129°±30+ (c=0.055, CHCl$_3$)

A solution of compound B in chloroform was treated with diethyl ether to obtain crystals which were then recrystallized twice from the same solvent system. By the above procedure there was obtained compound B as crystals melting at 155°–178° C.(gradually decomposed.)

REFERENCE EXAMPLE 12

The following compound can be produced in the same manner as Reference Example 11.

(A) From maytansinol and N-methyl-N-propionyl-L-alanine, there are obtained natural type (L-form) maytanprine [colorless needles, m.p. 185°–189° C.(slightly decomp.)] and D-maytanprine [colorless needles, m.p. 192°–197° C.(decomp.)].

(B) From maytansinol and N-isobutyryl-N-methyl-L-alanine, there are obtained natural type (L-form) maytanbutine [colorless needles, m.p. 185°–187° C.(decomp.)] and D-maytanbutine [colorless needles, m.p. 195°–198° C.(decomp.)].

(C) From maytansinol and N-isovaleryl-N-methyl-L-alanine, there are obtained natural type (L-form) maytanvaline and D-maytanvaline.

Natural-type Maytanvaline

NMR spectrum (CDCl$_3$) δ: 0.79(3H,s), 0.91(3H, d, J=6 Hz), 0.95(3H, d, J=6 Hz), 1.27(3H, d, J=6 Hz), 1.30(3H, d, J=7 Hz), 1.64(3H, s), 2.13(2H, d, J=7 Hz), 2.15(1H, dd, J=14 Hz & 3 Hz), 2.60(1H, dd, J=14 Hz & 11 Hz), 2.83(3H, s), 3.00(1H, d, J=9 Hz), 3.07(1H, d, J=13 Hz), 3.17(3H, s), 3.34(3H, s), 3.47(1H, d, J=9 Hz), 3.59(1H, br.), 3.65(1H, d, J=13 Hz), 3.95(3H, s), 4.27(1H, m), 4.74(1H, dd, J=12 Hz & 3 Hz), 5.35(1H, q, J=7 Hz), 5.64(1H, dd, J=15 Hz & 9 Hz), 6.28(1H, br.s), 6.39(1H, dd, J=15 Hz & 11 Hz), 6.67(1H, d, J=2 Hz), 6.69(1H, d, J=11 Hz), 6.79(1H, d, J=2 Hz), 0.7–2.0(3H).

Mass spectrum (m/e): 733, 672, 485, 470, 450, 170.

D-maytanvaline

NMR spectrum (CDCl$_3$) δ: 0.89(3H, s), 0.93(3H, d, J=6 Hz), 0.96(3H, d, J=6 Hz), 1.26(3H, d, J=4 Hz), 1.49(3H, d, J=7 Hz), 1.69(3H, s), 2.66(1H, dd, J=15 Hz & 12 Hz), 3.02(3H, s), 3.12(3H, s), 3.18(1H, d, J=13 Hz), 3.32(3H, s), 3.42(1H, d, J=9 Hz), 3.50(1H, d, J=13 Hz), 3.96(3H, s), 4.29(1H, m), 4.92(1H, dd, J=11 Hz & 3 Hz), 5.00(1H, q, J=7 Hz), 5.05(1H, br.), 5.78(1H, dd, J=15 Hz & 9 Hz), 6.17(1H, d, J=11 Hz), 6.24(1H, s), 6.43(1H, dd, J=15 Hz & 11 Hz), 6.77(1H, d, J=1.5Hz), 6.83(1H, d, J=1.5 Hz), 0.8–2.5(7H).

Mass spectrum (m/e): 733, 672, 485, 470, 450, 170.

REFERENCE EXAMPLE 13

(i) In 600 ml of methanol was suspended 53.5 g (0.52 mole) of N-methyl-L-alanine, and under ice-cooling and stirring, 76 g of dry hydrogen chloride gas was dissolved. The suspension of the starting material was liquidated with the progress of the reaction, and after stirring at room temperature overnight, a homogeneous solution was obtained. After 85 g (0.8 mole) of methyl orthoformate was added, the reaction mixture was further allowed to stand at room temperature for 24 hours. The minor amounts of insolubles were filtered off and the filtrate was concentrated under reduced pressure. By the above procedure there was obtained the hydrochloride of N-methyl-L-alanine methyl ester as a solid product.

NMR spectrum (in DMSO-d$_6$) δ: 1.50(3H, d, J=7 Hz), 2.60(3H, m; after addition of D$_2$O, s), 3.75(3H, s), 4.12(1H,m; after addition of D$_2$O, q, J=7 Hz), 9.83(2H, br.).

(ii) In 300 ml of chloroform was dissolved 33.7 g (0.22 mole) of N-methyl-L-alanine methyl ester.hydrochloride, followed by the addition of 65 ml of acetic anhydride and 110 ml of triethylamine. The mixture was allowed to stand at room temperature for 24 hours and, after the excess acetic anhydride was decomposed with water, was neutralized with sodium hydrogen carbonate. The chloroform layer was separated, the water layer was extracted with ethyl acetate (120 ml×5), and the chloroform and ethyl acetate layers were combined and concentrated under reduced pressure. The brown oil thus obtained was dissolved in chloroform, washed with aqueous sodium hydrogen carbonate and concentrated under reduced pressure. By the above procedure there was obtained 31.8 g of N-acetyl-N-methyl-L-alanine methyl ester as brown oil.

NMR spectrum (CDCl$_3$) δ: 1.38(3H, d, J=7 Hz), 2.12(3H, s), 2.97(3H, s), 3.70(3H, s), 5.23(1H, q, J=7 Hz).

The ester obtained above was dissolved in a mixture of 100 ml methanol and 170 ml 1 N-aqueous sodium hydroxide. The solution was allowed to stand at room temperature for 2 hours, after which the methanol was removed under reduced pressure. The alkaline aqueous solution was extracted with chloroform. The water layer was brought to pH 1 with concentrated hydrochloric acid under ice-cooling and extracted with ethyl acetate (140 ml×5). The extract was dried over anhydrous sodium sulfate and concentrated under reduced pressure to recover a white solid. Recrystallization from ethyl acetate-hexane yielded 8.1 g colorless needles of N-acetyl-N-methyl-L-alanine.

$[\alpha]_D^{25}$ −58.5° (c=1, DMF); −74.3° (c=1, H$_2$O). m.p. 121°–122° C.

(iii) The following compounds can be produced in the same manner as above.
(A) From N-methyl-L-alanine methyl ester.HCl and propionic anhydride, there is obtained N-methyl-N-propionyl-L-alanine (colorless prisms), m.p. 108°–110° C.
(B) From N-methyl-L-alanine methyl ester.HCl and isobutyryl chloride, there is obtained N-isobutyryl-N-methyl-L-alanine (colorless prisms), m.p. 117°–118° C.
(C) From N-methyl-L-alanine methyl ester.HCl and isovaleryl chloride, there is obtained N-methyl-N-isovaleryl-L-alanine (colorless scales), m.p. 88°–89° C.

REFERENCE EXAMPLE 14

(i) Production of β-methoxycarbonylethyl isocyanate

In 600 ml of dry toluene was dissolved 26.4 g of monomethyl succinate, followed by the addition of 55 g of diphenylphosphorylazide and 22 g of triethylamine. The mixture was allowed to stand at room temperature with stirring for 3 hours, after which it was washed with water and dried. The solvent was concentrated to about one-third of its original volume and, finally, the mixture was refluxed for 2 hours. After the solvent was completely evaporated off, the residue was distilled under reduced pressure. By the above procedure there was obtained 13.6 g of the above-indicated compound. b.p.$_8$: 64°–66° C.

(ii) Production of 5-dimethylaminopentyl isocyanate

In 136 ml of ethanol were dissolved 23.5 g of methyl 6-N,N-dimethylaminocaproate and 10.2 g of hydrazine hydrate and the solution was allowed to stand under reflux overnight. To the reaction mixture was added an excess of ethanolic oxalic acid and the white precipitate was recovered by filtration and extracted with 300 ml of 50% aqueous ethanol while hot. After cooling, some insoluble matter was removed and the filtrate was concentrated to dryness, whereupon 23.3 g of white powder was obtained. The entire amount of this powdery residue was suspended in 136 ml of water and treated under cooling with 12.3 g of sodium nitrite. The reaction mixture was adjusted to pH 10.5 with 5 N-sodium hydroxide and extracted three times with 150 ml of benzene each. The benzene layers were combined, washed with water, dried and kept under reflux for an hour. The solvent was carefully evaporated off and the residue was distilled under reduced pressure. By the above procedure there was obtained 6.1 g of the above-indicated compound, b.p.$_{14}$: 110°–115° C.

REFERENCE EXAMPLE 15

In 10 ml of dry dichloromethane was dissolved 56 mg (0.099 m mole) of maytansinol, followed by the addition of 24 mg (0.202 m mole) of phenyl isocyanate. At room temperature (18°–23° C.), 30 mg (0.221 m mole) of anhydrous zinc chloride was added and the mixture was stirred at that temperature for 3 hours. The reaction mixture was washed with water, dried (Na$_2$SO$_4$) and concentrated. The residue was chromatographed on silica gel [solvent system: ethyl acetate/ethyl acetate saturated with water=4:1 (V/V) through 3:1 (V/V)], the eluate being collected in 17 g fractions. Fractions No.9 through No.17 were pooled and the solvent was distilled off. By the above procedure there was obtained 58 mg of maytansinol 3-N-phenylcarbamate. m.p. 187°–189° C.(recrystallized from ethyl acetate-hexane)

REFERENCE EXAMPLE 16

In 10 ml of dichloromethane was dissolved in 54 mg (0.0956 m mole) of maytansinol, followed by the addition of 50 mg (0.877 m mole) of methyl isocyanate and 30 mg of cuprous chloride. The mixture was stirred at room temperature for 4 hours, after which it was filtered and concentrated. The residue was chromatographed on a column (25 mm dia.×45 cm long) of silica gel and elution was carried out with chloroform/methanol=40:1(V/V), the eluate being collected in 25 g fractions. Fractions No.34 through No.44 were pooled and concentrated to dryness to obtain 44 mg of a white glassy product. This product was reprecipitated from chloroform-hexane. By the above procedure there was obtained 28 mg of maytansinol 3-(N-methyl)carbamate 9-(2,4-dimethyl)allophanate as a white powder. m.p. 149°–151° C. (decomp.)

In 0.2 ml of dichloromethane was dissolved 10 mg of maytansinol 3-(N-methyl)carbamate 9-(2,4-dimethyl)allophanate, followed by the addition of 2 drops of trifluoroacetic acid. The mixture was stirred at room temperature for 5 minutes and, after a further amount of dichloromethane was added, it was washed with aqueous sodium hydrogen carbonate. The solvent was distilled off and the residue was chromatographed on 12 g of silica gel. By the above procedure there was obtained 5.2 mg of maytansinol 3-(N-methyl)carbamate.

REFERENCE EXAMPLE 17

The following compounds can be produced in the same manner as Reference Examples 14 through 16.

(A) From maytansinol and methyl isocyanate, there is obtained maytansinol 3-(N-methyl)carbamate, m.p. 196°-200° C.(decomp.).

(B) From maytansinol and butyl isocyanate, there is obtained maytansinol 3-(N-butyl)carbamate, m.p. 162°-165° C.

(C) From maytansinol and octadecyl isocyanate, there is obtained maytansinol 3-(N-octadecyl)carbamate, m.p. 105°-109° C.

(D) From maytansinol and cyclohexyl isocyanate, there is obtained maytansinol 3-(N-cyclohexyl)carbamate, m.p. 175°-178° C.

(E) From maytansinol and α-naphthyl isocyanate, there is obtained maytansinol 3-(N-α-naphthyl)carbamate, m.p. 172°-175° C.

(F) From maytansinol and p-ethoxyphenyl isocyanate, there is obtained maytansinol 3-(N-p-ethoxyphenyl)-carbamate, m.p. 221°-223° C.

(G) From dechloromaytansinol and phenyl isocyanate, there is obtained dechloromaytansinol 3-(N-phenyl)-carbamate as a colorless glassy product.

NMR spectrum (CDCl$_3$) δppm: 0.87(3H, s), 1.26(3H, d, J=6 Hz), 1.70(3H, s), 2.03(3H, s), 2.23(1H, dd, J=2.5 Hz & 14 Hz), 2.69(1H, dd, J=11 Hz & 14 Hz), 2.87(1H, d, J=9 Hz), 3.23(3H, s), 3.30(3H, s), 3.42(1H, d, J=9 Hz), 3.49(1H, d, J=14 Hz), 3.85(3H, s), 4.30(1H, m), 4.78(1H, dd, J=2.5 Hz & 11 Hz), 5.37(1H, dd, J=9 Hz & 15 Hz), 6.10(1H, d, J=10.5 Hz), 6.39(1H, s), 6.43(1H, dd, J=10.5 Hz & 15 Hz), 6.57-7.56(ca. 9H, m), etc.

(H) From maytansinol and isopropyl isocyanate, there is obtained maytansinol 3-N-isopropylcarbamate. Mass spectrum, (m/e): 588(M+-61).

(I) From maytansinol and 3-pyridylisocyanate, there is obtained maytansinol 3-(N-m-pyridyl)carbamate. Mass spectrum (m/e), 623 (M+-61).

(J) From maytansinol and 5-dimethylaminopentyl isocyanate, there is obtained maytansinol 3-(N-5-dimethylaminopentyl)carbamate. Mass spectrum (m/e), 659(M+-61).

(K) From maytansinol and β-methoxycarbonylethyl isocyanate, there is obtained maytansinol 3-(N-β-methoxycarbonylethyl)carbamate. Mass spectrum (m/e), 632 (M+-61).

(L) From maytansinol and N,N-dimethylcarbamoyl chloride, there is obtained maytansinol 3-N,N-dimethylcarbamate. Rf=0.39(solvent: chloroform/methanol=95:5); mass spectrum (m/e), 574(M+-61).

REFERENCE EXAMPLE 18

A solution of 57 mg of maytansinol in 2.0 ml of dry tetrahydrofuran was treated with 5 molar equivalents of n-butyllithium (15% solution in hexane) at −20° C. in a stream of nitrogen. To this was added 61 mg of isopropyl chloroformate and the mixture was stirred for 15 minutes at the same temperature. Then, the reaction mixture was warmed up to 0° C., treated with 0.5 ml of saturated aqueous solution of sodium chloride and 2.0 ml of tetrahydrofuran. The organic layer was separated, dried and the solvent was evaporated. And, the residue was chromatographed on a silica gel column to give 5 mg of maytansinol 3-isopropylcarbonate.

Rf value in a silica gel thin-layer chromatography with chloroform/methanol=95/5 (V/V) on a precoated plate (Art. 5642, Merck, Germany).

Mass spectrum (m/e): 650(M+), 589(M+-61)

REFERENCE EXAMPLE 19

A solution of dechloromaytansinol (53 mg) in 2.0 ml of dry tetrahydrofuran was treated as in Reference Example 18 with 10 mole equivalent of n-butyllithium. To this was added 10 molar equivalents of benzyl chloroformate as a 30% solution in toluene. After 15 minutes' stirring at the same temperature, the reaction mixture was warmed up to 0° C. and treated with 0.5 ml of saturated aqueous solution of sodium bicarbonate. And then, the organic layer was separated, dried and the solvent evaporated. The residue was chromatographed as in Reference Example 18 to give 23 mg of dechloromaytansinol 3-benzylcarbonate.

Rf value (conditions are the same as in Reference Example 18)=0.54,

Mass spectrum (m/e): 603 (M+-61).

REFERENCE EXAMPLE 20

The following compound can be produced in the same manner as Reference Example 18 or 19.

(A) From maytansinol and n-octyl chloroformate, there is obtainwed maytansinol 3-n-octylcarbonate. Thin layer chromatography, silica gel (E Merck, HPTLC), Rf=0.61 (developing solvent: chloroform:methanol=95:5, Mass spectrum (m/e): 659 (M+-61).

(B) From maytansinol and phenyl chloroformate, there is obtained maytansinol 3-phenylcarbonate. Thin layer chromatography, silica gel (E. Merck), HPTLC), Rf=0.45 (developing solvent: chloroform:methanol=95:5); Mass spectrum (m/e): 623 (M+-61).

REFERENCE EXAMPLE 21

Maytansinol, maytanacine and maytansinol propionate producible Nocardia sp. No. C-15003(IFO 13726; FERM-P No. 3992, ATCC-31281) as grown on a slant medium (yeast extract-malt extract agar) was used to inoculate a 200 ml conical flask containing 40 ml of a seed culture medium (2% glucose, 3% soluble starch, 1% raw soybean meal, 1% corn steep liquor, 0.5% Polypepton, 0.3% NaCl, 0.5% CaCO$_3$, pH 7.0). The inoculated medium was incubated at 28° C. on a rotary shaker for 48 hours to obtain an inoculum. A 0.5 ml portion of the inoculum thus obtained was transferred to a 200 ml conical flask containing 40 ml of a fermentation medium composed of 5% dextrin, 3% corn steep liquor, 0.1% polypepton and 0.5% CaCO$_3$ (pH 7.0), and cultivated on rotary shaker at 28° C. for 90 hours to give seed culture.

As determined by the serial dilution method using *Tetrahymena pyriformis* W as an assay organism and maytansinol propionate as the standard product, production potency of the above culture was found to be 25 μg/ml. Polypepton: a product of Daigo Nutritive Chemicals Ltd., Japan.

REFERENCE EXAMPLE 22

A 10 ml portion of the seed culture obtained in Reference Example 21 was transferred to a 2 l Sakaguchi flask containing 500 ml of a seed culture medium and incubated on a rotary shaker at 28° C. for 48 hours. A 500 ml portion of the resultant culture was transferred to a 50 l tank of stainless steel containing 30 l of seed culture medium and cultivated for 48 hours at 28° C., 30 l/min. aeration, 280 r.p.m. ($\frac{1}{2}$DT) and 1 kg/cm$^2$ internal pressure to obtain a seed culture. This culture was used to seed a 200 l tank of stainless steel containing 100 l of a fermentation medium similar to the one used in Reference Example 21 at an inoculation rate of 10%. The inoculated medium was incubated for 90 hours at 28° C., 100 l/m. aeration, 200 r.p.m. (½DT) and 1 kg/cm$^2$ internal pressure. As determined by the same procedure as that described in Reference Example 21, production potency of the culture obtained above was found to be 25 μg/ml.

To 90 l of the culture obtained above was added 2 kg of Hyflo Super Cel (Johnes and Manville Product, U.S.A.) and, after thorough mixing, the mixture was filtered on a pressure filter to obtain 85 l of filtrate and 32 kg of moist cells. The filtrate (85 l) was stirred and extracted with 30 l of ethyl acetate. This procedure was repeated once again. The ethyl acetate layers were pooled, washed twice with 30 l portions of water, dried by the addition of 500 g of anhydrous sodium sulfate and concentrated under reduced pressure to 200 ml. Petroleum ether was added to the concentrate and the resultant precipitate was recovered by filtration (53 g). This crude product I was stirred with 100 ml of ethyl acetate and the insolubles were filtered off. The filtrate was stirred with 10 g of silica gel (E. Merck AG. Germany, 0.05–0.2 mm) and the ethyl acetate was removed under reduced pressure. The residue was applied to the top of a silica gel column (400 ml). Elution was carried out with 500 ml of n-hexane, 500 ml of hexane/ethyl acetate (3:1), 500 ml of hexane/ethyl acetate (1:1), 500 ml of hexane/ethyl acetate (1:3), 500 ml of ethyl acetate, 1 l of ethyl acetate/methanol (50:1), and 1 l of ethyl acetate-methanol (25:1), with the eluate being collected in 100 ml fractions. One ml portion of each fraction was concentrated to dryness, and 0.1 ml of ethyl acetate was added to the concentrate. The mixture was spotted at 2.5 cm from the bottom edge of a silica gel-glass plate (E. Merck, AG, Germany, Kieselgel 60 $F_{254}$, 0.25 mm, 20×20) and developed for about 17 cm with a solvent system of ethyl acetate/methanol (19:1). After development, detection was carried out with ultraviolet ray (2537 A). The active fractions No.25–No.30 of Rf 0.58–0.63 and the fractions No. 38–40 of Rf 0.25–0.30 were collected and concentrated under reduced pressure to about 20 ml, respectively. To these concentrates were added each 150 ml of petroleum ether to obtain 5 g of a crude product II and 2 g of crude maytansinol.

In 10 ml of ethyl acetate was dissolved 0.5 g of the crude product II obtained above and the solution was stirred well with 4 g of silica gel (E. Merck AG, Germany, 0.05–0.2 mm). The ethyl acetate was removed under reduced pressure. The residue was applied to the top of a column of 300 ml silica gel and the column was first washed with 500 ml of chloroform and then eluted with 500 ml of chloroform/methanol (50:1), 500 ml of chloroform/methanol (20:1) and 500 ml of chloroform/methanol (10:1). The eluate was collected in 25 ml fractions.

A 0.5 ml portion of each fraction was concentrated under reduced pressure. To the concentrate was added 0.05 ml of ethyl acetate, and the mixture as a sample was subjected to thin layer chromatography (developing system: chloroform/methanol=9:1). The fraction Nos. 40 and 41 absorbing at 2537 A in the zone of Rf 0.48–0.50 were collected and concentrated to dryness under reduced pressure. To the residue was added 0.5 ml of ethyl acetate and the mixture was allowed to stand, whereupon 50 mg mixed crystals of maytanacine and maytansinol propionate were obtained.

50 Milligrams of the above mixed crystals of maytanacine and maytansinol propionate was dissolved in 5 ml of methanol, followed by addition of 100 mg of sodium chloride and 5 ml of water. A column measuring 1.8 cm in diameter was packed with 200 ml of Diaion HP-10 (Mitsubishi Chemical Industries, Ltd., Japan) and washed with 600 ml of 50% methanol/water containing 5% of NaCl. The sample solution prepared above was passed through the column, and gradient elution was carried out using 1.5 l of 60% methanol/water containing 5% NaCl and 1.5 l of 95% methanol/water. The eluate was collected in 15 ml fractions and each fraction was investigated by thin layer chromatography. The fractions 130 to 135 contained maytanacine, and the fractions 138–142 contained maytansinol propionate.

Each group of fractions was concentrated and dissolved by the addition of 30 ml of water and 50 ml of ethyl acetate. The solution was shaken in a separatory funnel and the water layer was separated and, after washing twice with 30 ml portions of water, the ethyl acetate layer was dried over anhydrous sodium sulfate, concentrated and allowed to stand. In the above manner, crystals were obtained from each group of fractions. The crystals were collected by filtration and dried.

Maytanacine: 13 mg.

Maytansinol propionate: 25 mg.

In 3 ml of ethyl acetate was dissolved 0.2 g of the crude maytansinol obtained above and the solution was stirred well with 0.5 g of silica gel (E. Merck AG, Germany, 0.05–0.2 mm). The ethyl acetate was removed under reduced pressure. The residue was applied to the top of a column of 80 ml silica gel and the column was first washed with 150 ml of chloroform and then eluted with 150 ml of chloroform/methanol (50:1), 150 ml of chloroform/methanol (20:1) and 300 ml of chloroform/methanol (10:1). The eluate was collected in 10 ml fractions and a 0.5 ml portion of each fraction was concentrated under reduced pressure. To the concentrate was added 0.05 ml of ethyl acetate, and the mixture as a sample was subjected to thin layer chromatography (developing system: chloroform/methanol=9:1). The fractions which were detected as absorption band of 2537 A, having the Rf 0.33–0.38, were collected and concentrated to dryness under reduced pressure. To the residue was added 0.5 ml of ethyl acetate and the mixture was allowed to stand, whereupon 20 mg crystals of maytansinol were obtained.

The physico-chemical properties of thus obtained maytansinol, maytanacine and maytansinol propionate are shown in Table 2.

TABLE 2

| | Maytanacine $C_{30}H_{39}ClN_2O_9$ | Maytansinol propionate $C_{31}H_{41}ClN_2O_9$ | Maytansinol $C_{28}H_{37}ClN_2O_8$ |
|---|---|---|---|
| Melting point (°C.) | 235–236° C. | 188–190° C. | 172.5–174° C. |
| Specific rotation | $[\alpha]_D^{22°}$ −121° ± 10° (C = 0.25 CHCl$_3$) | $[\alpha]_D^{22°}$ −127° ± 10° (C = 0.35 CHCl$_3$) | $[\alpha]_D^{22°}$ −313° ± 10° (C = 0.22 CHCl$_3$) |
| Analysis Found (%) | C 59.62 H 6.93 N 4.28 Cl 5.74 | C 59.93 H 6.82 N 4.32 Cl 5.57 | C 59.28 H 6.38 N 5.02 Cl 6.15 |
| Analysis Calcd. (%) | C 59.85 H 6.48 N 4.61 Cl 5.84 | C 59.94 H 6.65 N 4.51 Cl 5.71 | C 59.52 H 6.60 N 4.96 Cl 6.27 |

TABLE 2-continued

| | Maytanacine $C_{30}H_{39}ClN_2O_9$ | Maytansinol propionate $C_{31}H_{41}ClN_2O_9$ | Maytansinol $C_{28}H_{37}ClN_2O_8$ |
|---|---|---|---|
| Ultraviolet absorption spectrum | 233(30330) 240(sh 28240) 252(27850) 280(5680) 288(5660) | 233(30240) 240(sh 28400) 252(27650) 280(5740) 288(5710) | 232(32750) 244(sh 30850) 252(31650) 281(5750) 288(5700) |
| Infrared absorption spectrum | 1740, 1730, 1670, 1580 | 1740, 1730, 1670, 1580 | 1715, 1670, 1580 |
| Mass spectrum m/e | 545, 485, 470, 450 | 559, 485, 470, 450 | 503, 485, 470, 450 |
| Acid, neutral or basic | lipophyl and neutral substance | lipophyl and neutral substance | lipophyl and neutral substance |
| Color reactions | Dragendorff: Positive Beilstein: Positive | Dragendorff: Positive Beilstein: Positive | Dragendorff: Positive Beilstein: Positive |

REFERENCE EXAMPLE 23

Nocardia sp. No. C-15003 (IFO 13726; FERM-P No. 3992; ATCC-31281) as grown on a slant medium (yeast extract-malt extract-sugar) was inoculated into a 200 ml conical flask containing 40 ml of a seed culture medium (2% glucose, 3% soluble starch, 1% raw soybean meal, 1% corn steep liquor, 0.5% Polypepton, 0.3% NaCl, 0.5% CaCO$_3$, pH 7.0) contained in a 200 ml conical flask. The inoculated medium was incubated at 28° C. on a rotary shaker for 48 hours to obtain an inoculum. A 0.5 ml portion of the inoculum thus obtained was transferred to a 200 ml conical flask containing 40 ml of a fermentation medium composed of 5% dextrin, 3% corn steep liquor, 0.1% Polypepton and 0.5% CaCO$_3$ (pH 7.0), and cultivated on a rotary shaker at 28° C. for 90 hours.

As determined by the serial dilution method using Tetrahymena pyriformis W as an assay organism and ansamitocin P-3 as the standard sample, production potency of the above culture was found to 25 μg/ml.

REFERENCE EXAMPLE 24

A 10 ml portion of the seed culture obtained in Reference Example 23 was transferred to a 2 l Sakaguchi flask containing 500 ml of a seed culture medium and incubated on a rotary shaker at 28° C. for 48 hours. A 500 ml portion of the resultant culture was transferred to a 50 l tank of stainless steel containing 30 l of seed culture medium and cultivated at 28° C., 30 l/min aeration, 280 r.p.m. (½DT) and 1 kg/cm$^2$ internal pressure to obtain a seed culture. This culture was used to seed a 200 l tank of stainless steel containing 100 l of a fermentation medium similar to the one used in Reference Example 23 at an inoculation rate of 10%. The inoculated medium was incubated at 28° C., 100 l/m. aeration, 200 r.p.m. (½DT) and 1 kg/cm$^2$ internal pressure for 90 hours. As determined by the same procedure as that described in Reference Example 23, production potency of the culture obtained above was found to be 25 μg/ml.

REFERENCE EXAMPLE 25

To 95 l of the culture obtained in Reference Example 24 was added 2 kg of Hyflo Super Cel (Johns and Manville Sales Corp., Products, U.S.A.) and, after thorough mixing, the mixture was filtered on a pressure filter to obtain 85 l of filtrate and 32 kg of moist cells. The filtrate (85 l) was stirred and extracted with 30 l of ethyl acetate. This procedure was repeated once again. The ethyl acetate layers were pooled, washed twice with 30 l portions of water, dried by the addition of 500 g of anhydrous sodium sulfate and concentrated under reduced pressure to 200 ml. Petroleum ether was added to the concentrate and the resultant precipitate was recovered by filtration (53 g). This crude product I was stirred with 100 ml of ethyl acetate and the insolubles were filtered off. The filtrate was stirred with 10 g of silica gel (E. Merck AG, Germany, 0.05–0.2 mm) and the ethyl acetate was removed under reduced pressure. The residue was applied to the top of a silica gel column (400 ml). Elution was carried out with 500 ml of hexane, 500 ml of hexane/ethyl acetate (3:1), 500 ml of hexane/ethyl acetate (1:1), 500 ml of hexane/ethyl acetate (1:3), 500 ml of ethyl acetate and 1 l of ethyl acetate/methanol (50:1), with the eluate being collected in 100 ml fractions.

One-ml portion of each fraction was concentrated to dryness, and 0.1 ml of ethyl acetate was added to the concentrate to give a mixture. The mixture was spotted at 2.5 cm from the bottom edge of a silica gel-glass plate (E. Merck AG, Germany, 60 F$_{254}$, 0.25 mm, 20×20) and developed for about 17 cm with a solvent system of ethyl acetate/methanol (19:1). After development, detection was carried out with ultraviolet light (2537 A). The active fractions No. 23–No. 28 of Rf 0.6–0.65 were collected and concentrated under reduced pressure to about 20 ml. To this concentrate was added 150 ml of petroleum ether to obtain 15 g of a crude product II.

REFERENCE EXAMPLE 26

With stirring, 32 kg of the cells obtained in Reference Example 25 were extracted with 50 l of 70% acetone-water for 3 hours under stirring and, then, filtered on a pressure filter. The extraction with 50 l of 70% acetone-water and subsequent filtration was repeated once again. The filtrate were pooled and the acetone was removed by concentration under reduced pressure. The resultant aqueous system was passed through a column of 5 l Diaion HP-10 (Mitsubishi Chemical Industries, Ltd., Japan). The column was washed with 20 l of water and 50% aqueous methanol, followed by elution with 15 l of 90% methanol-water. The eluate was concentrated under reduced pressure to 3 l and shaken with 3 l of water and 3 l of ethyl acetate. The above procedure was repeated once again. The ethyl acetate layers were combined, washed with water, dried by the addition of anhydrous sodium sulfate and concentrated under reduced pressure to 200 ml. Following the addition of petroleum ether, the precipitate was recovered by filtration (28 g). The above product was purified by means of a column of silica gel to recover 8.0 g of crude product II.

REFERENCE EXAMPLE 27

In 10 ml of ethyl acetate was dissolved 1.5 g of the crude product II obtained in Reference Example 25 and the solution was stirred well with 4 g of silica gel (E. Merck AG, Germany, 0.05–0.2 mm). The ethyl acetate was removed under reduced pressure. The residue was applied to the top of a column of 300 ml silica gel and the column was first washed with 500 ml of chloroform and then eluted with 500 ml of chloroform/methanol (50:1), 500 ml of chloroform/methanol (20:1) and 500 ml of chloroform/methanol (10:1). The eluate was collected in 25 ml fractions.

A 0.5 ml portion of each fraction was concentrated under reduced pressure. To the concentrate was added 0.05 ml of ethyl acetate, and the mixture as a sample was subjected to silica gel thin layer chromatography (developing system: chloroform-methanol=9:1).

The fraction which were detected as absorption band of 2537 Å, having the Rf values of 0.50–0.60, were collected and concentrated to dryness under reduced pressure. To the residue was added 2 ml of ethyl acetate and the mixture was allowed to stand, whereupon 150 mg crystals of a mixture of ansamitocin P-3, P-3' and P-4 were obtained.

The above crystals of the mixture of ansamitocin P-3, P-3' and P-4 (150 mg) were dissolved in 15 ml of methanol, followed by addition of 300 mg of sodium chloride and 15 ml of water. A column measuring 1.8 cm in diameter was packed with 200 ml of Diaion HP-10 (Mitsubishi Chemical Industries, Ltd.) and calibrated with 600 ml of 50% methanol-water containing 5% of NaCl. The sample solution prepared above was passed through the column, and gradient elution was carried out using 1.5 l of 60% methanol-water containing 5% NaCl and 1.5 l of 95% methanol-water. The eluate was collected in 15 ml fractions and each fraction was investigated by silica gel thin layer chromatography. The fractions 145 to 153 contained ansamitocin P-3, the fractions 167–180 contained ansamitocin P-3' and P-4 and the fractions 185–190 contained ansamitocin P-4.

Each group of fractions was concentrated and dissolved by the addition of 50 ml of water and 100 ml of ethyl acetate. The solution was shaken in a separatory funnel and the water layer was separated and, after washing with two 50 ml-portions of water, the ethyl acetate layer was dried over anhydrous sodium sulfate, concentrated and allowed to stand. In the above manner, crystals were obtained from each group of fractions. The crystals were collected by filtration and dried.

ansamitocin P-3: 70 mg
ansamitocin P-3', P-4: 18 mg
ansamitocin P-4: 15 mg

The mixed crystals of ansamitocin P-3' and P-4 (18 mg) were dissolved in 0.3 ml of ethyl acetate and spotted in a line at a distance of 2.5 cm from the bottom edge of a silica gel glass plate (E. Merck AG, Germany, Kieselgel 60 $F_{254}$, 0.25 mm, 20×20), followed by development with ethyl acetate/methanol (19:1). After development to about 18 cm, the absorption band at Rf 0.68 (P-4) and Rf 0.65 (P-3') were scraped up and each was independently extracted twice with ethyl acetate containing a small amount of water. The resultant ethyl acetate extract was washed with water, dried over anhydrous sodium sulfate, concentrated under reduced pressure and allowed to stand.

10 mg crystals of ansamitocin P-4 and 3 mg crystals of ansamitocin P-3' were obtained from the fractions of Rf 0.68 and Rf 0.65, respectively.

The physical and chemical properties of ansamitocin P-3, P-3' and P-4 obtained as above are shown in Table 3 below.

TABLE 3

| | Ansamitocin | | |
|---|---|---|---|
| | P-3 $C_{32}H_{43}ClN_2O_9$ = 635.169 | P-3' $C_{32}H_{43}ClN_2O_9$ = 635.169 | P-4 $C_{33}H_{45}ClN_2O_9$ = 649.196 |
| m.p. (°C.) | 190–192 | 182–185 | 177–180 |
| Specific rotation $[\alpha]_D^{22°}$ | $-136° \pm 10°$ (c = 0.375 $CHCl_3$) | $-134° \pm 10°$ (c = 0.11 $CHCl_3$) | $-142° \pm 10°$ (c = 0.522 $CHCl_3$) |
| Elemental analysis Found (%) | C 60.06 H 7.04 N 4.33 Cl 5.37 | C 60.09 H 7.02 N 4.34 Cl 5.99 | C 60.65 H 7.05 N 4.25 Cl 5.23 |
| Elemental analysis Calcd. (%) | C 60.51 H 6.82 N 4.41 Cl 5.58 | C 60.51 H 6.82 N 4.41 Cl 5.58 | C 61.05 H 6.99 N 4.32 Cl 5.46 |
| Ultraviolet absorption spectra nm ($\epsilon$) (in methanol) | 233(30250) 240(sh 28450) 252(27640) 280(5750) 288(5700) | 233(30155) 240(sh 28250) 252(27600) 280(5750) 288(5700) | 233(29900) 240(sh 28240) 252(27590) 280(5712) 288(5680) |
| Infrared absorption spectra ($cm^{-1}$) KBr | 1740, 1730, 1670, 1580, 1445, 1385, 1340, 1255, 1180, 1150, 1100, 1080 1038 | 1740, 1730, 1670, 1580, 1445, 1385, 1340, 1255, 1180, 1150, 1100, 1080, 1038 | 1740, 1730, 1670, 1580, 1445, 1385, 1340, 1255, 1180, 1150, 1100, 1080 1038 |
| Nuclear magnetic resonance spectra in 100 MHz $CDCl_3$ (ppm) | 1.27(d) (3H) 1.28(d) (3H) | 1.06(t) (3H) | 1.03(d) (6H) |
| Mass spectra m/e | 573, 485, 470, 450 | 573, 485, 470, 450 | 587, 485, 470, 450 |
| Solubility | Insoluble in petr. ether, n-hexane & water. Sparingly soluble in benzene & ether. Soluble in chloroform, | Insoluble in petr. ether, n-hexane & water. Sparingly soluble in benzene & ether. Soluble in chloroform, | Insoluble in petr. ether, n-hexane & water. Sparingly soluble in benzene & ether. Soluble in chloroform, |

TABLE 3-continued

| | Ansamitocin | | |
|---|---|---|---|
| | P-3<br>$C_{32}H_{43}ClN_2O_9 =$<br>635.169 | P-3'<br>$C_{32}H_{43}ClN_2O_9 =$<br>635.169 | P-4<br>$C_{33}H_{45}ClN_2O_9 =$<br>649.196 |
| | ethyl acetate,<br>acetone,<br>ethanol,<br>methanol,<br>pyridine,<br>tetrahydrofuran<br>& dimethyl-<br>sulfoxide. | ethyl acetate,<br>acetone,<br>ethanol,<br>methanol,<br>pyridine,<br>tetrahydrofuran<br>& dimethyl-<br>sulfoxide. | ethyl acetate,<br>acetone,<br>ethanol,<br>methanol,<br>pyridine,<br>tetrahydrofuran<br>& dimethyl-<br>sulfoxide. |
| Color<br>reactions | Dragendorff:<br>Positive<br>Beilstein:<br>Positive | Dragendorff:<br>Positive<br>Beilstein:<br>Positive | Dragendorff:<br>Positive<br>Beilstein:<br>Positive |

REFERENCE EXAMPLE 28

In 1 ml of tetrahydrofuran was dissolved 15 mg. of the mixture of ansamitocin P-3, P-3' and P-4 obtained in Reference Example 27 and, after the solution was cooled to $-5°$ C., 12 mg. of lithium aluminium hydride was added. The mixture was allowed to stand for 2 hours. Following the addition of 0.5 ml of a 1% aqueous solution of $H_2SO_4$, the reaction mixture was extracted with 2 ml of ethyl acetate. The ethyl acetate layer was washed with water, dried by the addition of anhydrous sodium sulfate and concentrated under reduced pressure. Preparative TLC with silica gel (solvent; ethyl acetate/methanol 19:1) was carried out on the concentrate and the zone in the neighborhood of 0.25–0.3 was scraped up and extracted with ethyl acetate containing a small volume of water. The extract was washed with water, dried over anhydrous sodium sulfate and concentrated under reduced pressure, whereupon crystals separated. The crystals were recovered by filtration and dried. By the above procedure was obtained 10 mg. of maytansinol, melting point 174° C.

Elemental analysis: Found: C, 59.65; H, 6.58; N, 5.02; Cl, 6.51; Calcd. for $C_{28}H_{37}ClN_2O_8$: C, 59.52; H, 6.60; N, 4.96; Cl, 6.27.

IR: 1715, 1670, 1580 (cm$^{-1}$).

UV(nm): 232(32750), 244(sh 30850), 252(31650), 281(5750), 288(5700).

In properties, this product is in good agreement with maytansinol obtained in Reference Example 22.

REFERENCE EXAMPLE 29

In 0.7 ml of pyridine was dissolved 100 mg of maytansinol. To the solution, cooled with ice, was added 0.35 ml of acetic anhydride. The mixture was left standing for 18 hours at room temperature (23°–25° C.). The reaction solution was poured into 5 ml of cold water and stirred. The precipitate separated out was collected by filtration and dried to obtain 85 mg of powdery substance. This powdery substance was dissolved in 1 ml of chloroform/methanol 10:1 (V/V). To the solution was added 0.2 g of silica gel, and mixed sufficiently. The mixture was then applied to the top of a silica gel column (80 ml). Elution was carried out with ethyl acetate saturated with water. The eluate was collected in 10 ml fractions. The fractions of No. 37–44 were collected, concentrated under reduced pressure. To the residue was added a small volume of ethyl acetate (about 0.5 ml) to dissolve the precipitating crystals again, then was left standing at room temperature. Precipitating crystals were collected by filtration, whereupon 36.0 mg. of maytanacine was obtained. The melting point of this was 231° C. and, when compared with maytanacine obtained in Reference Example 22 in mass spectrum, IR spectrum, UV-spectrum and thin layer chromatogram, this product was found to be identical with the maytanacine obtained in the above.

EXAMPLE 1

Bacillus megaterium IFO 12108 was inoculated into a culture medium (pH 7.5) containing 2% dextrin, 0.5% peptone, 0.5% yeast extract and 0.5% meat extract and the inoculated medium was shake-cultured at 30° C. for 16 hours. To 2.75 l of this culture was added 110 mg of ansamitocin P-4 and the reaction was carried out under shaking at 30° C. for 51 hours. As assayed by thin-layer chromatography (TLC), the ansamitocin P-4 had disappeared completely and, instead, PDM-4 had been produced in the reaction mixture.

EXAMPLE 2

To 2.75 l of the culture broth obtained in Example 1 was added 1.3 l of ethyl acetate and the mixture was stirred to extract. The mixture was suction-filtered through a filter coated with 30 g of Hyflo Super cel (Johns Manville Products Co., U.S.A.). This procedure was repeated for a second time. The ethyl acetate layers were combined, washed twice with 800 ml of 1/200 N-HCl and 400 ml of 0.5% aqueous sodium hydrogen carbonate in that order, and washed twice with 400 ml portions of water. It was dried with 10 g of anhydrous sodium sulfate and concentrated under reduced pressure to 2 ml. To this residue was added 50 ml of petroleum ether and the resultant precipitate was recovered by filtration (126 mg).

This crude product (i) of PDM-4 was dissolved in a small amount of chloroform and run onto a column (1 cm dia.) of 5 g of silica gel (E. Merck, AG, Germany, 0.05–0.2 mm). Elution was carried out with 100 ml of chloroform, 100 ml of chloroform/methanol (40:1) and 200 ml of chloroform/methanol (20:1), the eluate being collected in 10 ml fractions. Each fraction was spotted to a silica gel-glass plate (E. Merck AG, Germany, Kieselgel $^{60}F_{254}$, 0.25 mm, 20×20) at a distance of 2.5 cm from its bottom edge and the chromatogram was developed over about 17 cm with ethyl acetate/methanol (19:1). The fractions (Nos. 13 to 17) which were detected as absorption spots of 2537 A, having the Rf value of 0.64 were combined and concentrated under reduced pressure to about 1 ml. To the concentrate was added 30 ml of petroleum ether, whereby 79 mg of crude product (ii) of PDM-4 was obtained.

EXAMPLE 3

In a small amount of chloroform was dissolved 79 mg of the crude product (ii) of PDM-4 obtained in Example 2 and the solution was linearly applied to each of 4 silica gel-glass plates (E. Merck AG, Germany, Kieselgel $F_{254}$, 2 mm, 20×20) at a distance of 2.5 cm from its bottom edge. Each chromatogram was developed with ethyl acetate/methanol (19:1) and the absorbing zone at Rf 0.64 was scraped up and extracted twice with ethyl acetate containing a small amount of water. The ethyl acetate extract thus obtained was washed with water, dried over anhydrous sodium sulfate, concentrated under reduced pressure and treated with petroleum ether. By the above procedure there was obtained 68 mg of PDM-4 as a white powder.

EXAMPLE 4

To 5.5 l of the culture broth of *Bacillus megaterium* IFO 12108 as obtained in Example 1 was added 220 mg of maytansinol and the reaction was carried out under shaking at 30° C. for 30 hours. As assayed by TLC, maytansinol had decreased and, instead, demethylmaytansinol had been produced in the reaction system.

EXAMPLE 5

The culture broth obtained in Example 4 was purified as in Example 2 and subjected to TLC as in Example 2. The fractions at Rf$\approx$0.25 were collected to obtain 61 mg of a crude product of demethylmaytansinol. It was further purified as described in Example 3 to give 33 mg of demethylmaytansinol as a white powder.

EXAMPLE 6

To 12.5 l of the culture broth of *Bacillus megaterium* IFO 12108 obtained as in Example 1 was added 500 mg of maytansinol propionate and the reaction was carried out under shaking at 30° C. for 28 hours. As determined by TLC, maytansinol propionate had completely disappeared and, instead, demethylmaytansinol propionate had been produced in the culture broth.

EXAMPLE 7

With 12 l of ethyl acetate, 12.5 l of the culture broth obtained in Example 6 was purified as in Example 2 and TLC was performed thereon as in Example 2. The fractions at Rf$\approx$0.58 were collected, concentrated to dryness under reduced pressure, and allowed to stand with 5 ml of ethyl acetate. By the above procedure there was obtained 235 mg of crystals of demethylmaytansinol propionate.

EXAMPLE 8

To 1 l of a culture broth of *Bacillus megaterium* IFO 12108 as obtained in Example 1 was added a mixture (10 mg) of maytansinol, maytanacine, maytansinol propionate, ansamitocin P-3 and ansamitocin P-4 and the reaction was carried out under shaking at 30° C. for 24 hours. As assayed by TLC, the above mixture had decreased and, instead, the demethyl analogues of the above mixture had been formed in the culture broth. As the chromatogram was developed with a solvent of a mixture of ethyl acetate/methanol (19:1), there was detected demethylmaytansinol at Rf 0.25 to 0.30, demethylmaytanacine at Rf 0.54, demethylmaytansinol propionate at Rf 0.58, PDM-3 at Rf 0.61 and PDM-4 at Rf 0.64. With chloroform/methanol (9:1) as the developing solvent, there were detected demethylmaytansinol at Rf 0.30, demethylmaytanacine at Rf 0.38, demethylmaytansinol propionate at Rf 0.40, PDM-3 at Rf 0.42 and PDM-4 at Rf 0.44.

EXAMPLE 9

*Streptomyces flavotricini* IFO 12770 was inoculated into a culture medium (pH 7.2) containing 1% dextrin, 1% glucose, 1% glycerol, 0.5% peptone, 0.5% yeast extract, 0.5% meat extract, 0.3% sodium chloride and 0.5% calcium carbonate and shake culture was carried out at 28° C. for 48 hours. To 2 l of the resultant culture was added 20 mg of ansamitocin P-3 and the reaction was carried out under shaking at 28° C. for 48 hours. The culture broth was purified as Examples 2 and 3. By the above procedure there was obtained 12 mg of PDM-3 as a white powder.

EXAMPLE 10

To 2 l of a culture broth of *Streptomyces flavotricini* IFO 12770 obtained as in Example 9 was added 20 mg of maytanacine and the reaction was carried out under shaking at 28° C. for 48 hours. The culture broth was then purified and allowed to stand with a small amount of ethyl acetate as in Examples 2 and 3. By the above procedure there was obtained 6 mg of crystals of demethylmaytanacine.

EXAMPLE 11

*Actinomyces nigrescens* IFO 12894 was cultivated as in Example 9 and 10 mg of maytansinol propionate was added to 1 l of the culture. The reaction was carried out under shaking at 28° C. for 48 hours. As assayed by TLC, the maytansinol propionate had completely disappeared and instead, demethylmaytansinol propionate had been produced in the culture broth.

EXAMPLE 12

*Streptomyces platensis* IFO 12901 was cultivated as in Example 9 and 10 mg of maytansinol propionate was added to 1 l of the culture. The reaction was carried out under shaking at 28° C. for 48 hours. As assayed by TLC, the maytansinol propionate had completely disappeared and, instead, demethylmaytansinol propionate had been formed in the culture broth.

EXAMPLE 13

In 30 ml of tetrahydrofuran was dissolved 80 mg of crystals of demethylmaytansinol propionate obtained in Example 7 and the solution was cooled to $-5°$ C. To this solution was added 80 mg of lithium aluminum hydride. The reaction mixture was stirred in an ice-bath for 30 minutes, and after the addition of 10 ml of 1/200 N-hydrochloric acid, the mixture was extracted with 50 ml of ethyl acetate. The ethyl acetate layer was washed with water, dried by addition of anhydrous sodium sulfate and concentrated under reduced pressure.

Preparative TLC (silica gel) of the product was carried out on the concentrate with ethyl acetate/methanol (19:1) over a distance of 17 cm. The UV absorbing zone at Rf$\approx$0.25 to 0.40 was scraped up, extracted with ethyl acetate containing a small amount of water. The extract was washed with water, dried over anhydrous sodium sulfate and concentrated under reduced pressure. By the above procedure there was obtained 41 mg of demethylmaytansinol. The physico-chemical properties of this product were identical with those of the demethylmaytansinol obtained in Example 5.

EXAMPLE 14

In 20 ml of tetrahydrofuran was dissolved 50 mg of powder of PDM-3 obtained in Example 9 and after the solution was cooled to −5° C., 50 mg of lithium aluminum hydride was added. The reaction mixture was treated and purified as in Example 13 to obtain 27 mg of demethylmaytansinol as a white powder. The physicochemical properties of this product were identical with those of demethylmaytansinol obtained in Example 5.

EXAMPLE 15

The powder of PDM-4 (50 mg) obtained in Example 3 was treated and purified as in Example 13 to obtain 23 mg of demethylmaytansinol. Based on its physicochemical data, this product was identified with demethylmaytansinol obtained in Example 5.

EXAMPLE 16

The crystals of demethylmaytanacine (50 mg) obtained in Example 10 were treated and purified as in Example 13 to obtain 29 mg of demethylmaytansinol. Based on its physico-chemical data, this product was identified with the demethylmaytansinol obtained in Example 5.

EXAMPLE 17

In 20 ml of tetrahydrofuran was dissolved 30 mg of a mixture of demethylmaytanacine, demethylmaytansinol propionate, PDM-3 and PDM-4 obtained in Example 8, and after cooling to −5° C., 30 mg of lithium aluminum hydride was added. This reaction mixture was treated and purified as in Example 13 to obtain 12 mg of demethylmaytansinol. Based on its physicochemical data, this product was identified with the demethylmaytansinol obtained in Example 5.

EXAMPLE 18

*Streptomyces libani* IFO 13452 was cultivated as in Example 9 and 10 mg of ansamitocin P-3 was added to 1 l of the resultant culture. The reaction was carried out under shaking at 28° C. for 48 hours. As assayed by TLC, the ansamitocin P-3 had completely disappeared and, instead, PDM-3 has been formed in the culture broth.

The properties of the compounds obtained in the foregoing Examples are given in the following table.

TABLE 4

|  | Demethyl maytansinol $C_{27}H_{35}ClN_2O_8$ = 551.050 | Demethyl maytanacine $C_{29}H_{37}ClN_2O_9$ = 593.088 | Demethyl maytansinol propionate $C_{30}H_{39}ClN_2O_9$ = 607.115 | PDM-3 $C_{31}H_{41}ClN_2O_9$ = 621.142 | PDM-4 $C_{32}H_{43}ClN_2O_9$ = 635.169 |
|---|---|---|---|---|---|
| Molecular formula, Molecular weight | | | | | |
| Melting point (°C.) | 194–196 | 224–226 | 193–195 | 165–168 | 185–188 |
| Specific rotation $[\alpha]_D^{22}$ (CHCl$_3$) | −201° ± 10° (c = 0.215) | −115° ± 10° (c = 0.12) | −104° ± 10° (c = 0.22) | −132° ± 10° (c = 0.20) | −110° ± 10° (c = 0.22) |
| (MeOH) | −209° ± 10° (c = 0.50) | −98° ± 10° (c = 0.505) | −112° ± 10° (c = 0.54) | −120° ± 10° (c = 0.52) | −112° ± 10° (c = 0.51) |
| Elemental analysis Found (%) C | 58.53 | 58.66 | 59.23 | 59.61 | 60.17 |
| H | 6.69 | 6.43 | 6.68 | 6.92 | 7.08 |
| N | 4.81 | 4.67 | 4.55 | 4.36 | 4.27 |
| Cl | 6.28 | 5.79 | 5.69 | 5.47 | 5.33 |
| Elemental analysis Calculated (%) C | 58.85 | 58.73 | 59.35 | 59.94 | 60.51 |
| H | 6.40 | 6.29 | 6.48 | 6.65 | 6.82 |
| N | 5.08 | 4.72 | 4.61 | 4.51 | 4.41 |
| Cl | 6.43 | 5.98 | 5.84 | 5.71 | 5.58 |
| Ultraviolet ray absorption spectra nm ($\epsilon$) (MeOH) | 232 (31200) 242 (33400) 251 (34000) 280 (6890) 288 (6840) | 232 (29700) 242 (30700) 251 (31000) 280 (6110) 288 (6050) | 232 (30000) 242 (30900) 251 (31200) 280 (6380) 288 (6320) | 232 (28900) 242 (29200) 251 (29200) 280 (6150) 288 (5970) | 232 (30000) 242 (30400) 251 (30500) 280 (6360) 288 (6290) |
| Infrared ray absorption spectra cm$^{-1}$ (KBr) | 1726, 1697, 1640, 1587, 1435, 1390, 1345, 1305, 1276, 1175, 1155, 1107, 1080, 1005 | 1737 1697, 1660, 1594, 1443, 1397, 1378, 1335, 1280, 1234, 1180, 1158, 1100, 1083, 1030 | 1737, 1715, 1642, 1594, 1442, 1397, 1344, 1320, 1280, 1238, 1175, 1100, 1085, 1020 | 1740, 1710, 1642, 1593, 1443, 1397, 1355, 1320, 1283, 1238, 1185, 1155, 1110, 1085, 1018 | 1738, 1715, 1662, 1585, 1442, 1395, 1377, 1300, 1283, 1183, 1167, 1110, 1085, 1018 |
| Nuclear magnetic resonance spectra ppm (100 MHz) (solvent) | 3.06 (3H, s) 3.26 (3H, s) (d$_6$-DMSO) | 2.14 (3H, s) 3.06 (3H, s) 3.27 (3H, s) (d$_6$-DMSO) | 1.07 (3H, t) 3.04 (3H, s) 3.27 (3H, s) (d$_6$-DMSO) | 1.27 (3H, d) 1.29 (3H, d) 3.19 (3H, s) 3.38 (3H, s) (CDCl$_3$) | 1.03 (6H, d) 3.17 (3H, s) 3.39 (3H, s) (CDCl$_3$) |
| Mass spectra m/e | 489, 471 | 531, 471 456, 436 | 545, 471 456, 436 | 559, 471 456, 436 | 573, 471 456, 436 |
| Solubility | Freely soluble in pyridine, dimethyl sulfoxide. Soluble in chloroform, ethyl acetate, tetrahydrofrun, acetone, ethanol, methanol. Slightly soluble in benzene, ether. Very slightly | Freely soluble in pyridine, dimethyl sulfoxide. Soluble in chloroform, ethyl acetate, tetrahydrofrun, acetone, ethanol, methanol. Slightly soluble in benzene, ether. Very slightly | Freely soluble in pyridine, dimethyl sulfoxide. Soluble in chloroform, ethyl acetate, tetrahydrofrun, acetone, ethanol, methanol. Slightly soluble in benzene, ether. Very slightly | Freely soluble in pyridine, dimethyl sulfoxide. Soluble in chloroform, ethyl acetate, tetrahydrofrun, acetone, ethanol, methanol. Slightly soluble in benzene, ether. Very slightly | Freely soluble in pyridine, dimethyl sulfoxide. Soluble in chloroform, ethyl acetate, tetrahydrofrun, acetone, ethanol, methanol. Slightly soluble in benzene, ether. Very slightly |

TABLE 4-continued

| | Demethyl maytansinol | Demethyl maytanacine | Demethyl maytansinol propionate | PDM-3 | PDM-4 |
|---|---|---|---|---|---|
| Molecular formula, Molecular weight | $C_{27}H_{35}ClN_2O_8 =$ 551.050 | $C_{29}H_{37}ClN_2O_9 =$ 593.088 | $C_{30}H_{39}ClN_2O_9 =$ 607.115 | $C_{31}H_{41}ClN_2O_9 =$ 621.142 | $C_{32}H_{43}ClN_2O_9 =$ 635.169 |
| Color reactions | soluble in water. Practically insoluble in petroleum ether, n-hexane. Dragendorff: positive Beilstein: positive | soluble in water. Practically insoluble in petroleum ether, n-hexane. Dragendorff: positive Beilstein: positive | soluble in water. Practically insoluble in petroleum ether, n-hexane. Dragendorff: positive Beilstein: positive | soluble in water. Practically insoluble in petroleum ether, n-hexane. Dragendorff: positive Beilstein: positive | soluble in water. Practically insoluble in petroleum ether, n-hexane. Dragendorff: positive Beilstein: positive |

EXAMPLE 19

*Bacillus megaterium* IFO 12108 was inoculated into a culture medium (pH 7.5) containing 2% of dextrin, 0.5% of peptone, 0.5% of yeast extract and 0.5% of meat extract and shake culture was carried out at 28° C. for 16 hours. To 1.5 l of this culture was added 30 mg of maytansinol 3-picolinate and the reaction was carried out under shaking at 28° C. for 29 hours. As assayed by TLC, maytansinol 3-picolinate had completely disappeared and, instead, demethylmaytansinol 3-picolinate had been formed in the culture broth.

EXAMPLE 20

To 1.5 l of the culture broth obtained in Example 19 was added 750 ml of ethyl acetate and after extraction under stirring, the mixture was suction-filtered through a filtering setup with 15 g of Hyfro Super Cel (Johns-Manville Products, Corp., U.S.A.). This procedure was repeated for a second time. The ethyl acetate layers were combined, washed with 300 ml portions of water, dried over 10 g of anhydrous sodium sulfate and concentrated under reduced pressure.

By this procedure there was obtained crude product (i). This crude product (i) was dissolved in a small amount of chloroform and run onto a column (1 cm dia.) of 5 g silica gel (Merck, Germany, 0.05–0.2 mm.). Elution was carried out with 150 ml of chloroform and chloroform-methanol (20:1), the eluate being collected in 10 ml fractions. Each fraction was spotted on a silica gel-glass plate (Kieselgel 60 $F_{254}$, Merck, Germany, 0.25 mm, 20×20) at a distance of 2.5 cm from its bottom edge and the chromatogram was developed with chloroform-methanol (9:1). The fractions (Nos. 12 to 16) which were detected as absorption band of 2537 A, having the Rf value of 0.40 were collected and concentrated under reduced pressure to obtain 18 mg of crude product (ii). This crude product was dissolved in a small amount of chloroform and the solution was linearly applied to each of four silica gel-glass plates at a distance of 2.5 cm from its bottom edge and the chromatograms were developed with water-saturated ethyl acetate. The UV absorbing zones at Rf 0.30 were scraped up and extracted twice with ethyl acetate containing a small amount of water. The ethyl acetate extract was washed with water, dried over anhydrous sodium sulfate and concentrated under reduced pressure. The concentrate was treated with petroleum ether to obtain 6 mg of demethylmaytansinol 3-picolinate as a white powder.

UV spectrum ($\lambda_{max}^{MeOH}$)nm: 232, 243, 252, 280, 289.
Mass spectrum (m/e): 655, 594, 471, 456, 436.

EXAMPLE 21

To 2 l of a culture broth of *Bacillus megaterium* IFO 12108 obtained as in Example 19 was added 37 mg of maytansinol 3-(N-phenyl)carbamate and the reaction was carried out under shaking at 28° C. for 48 hours. As assayed by TLC, the maytansinol 3-(N-phenyl)carbamate had completely disappeared and, instead, demethylmaytansinol 3-(N-phenyl)carbamate had been formed in the culture broth.

EXAMPLE 22

The culture broth obtained in Example 21 was purified as in Example 20 and TLC was performed thereon as in Example 20. The fractions at Rf 0.40 were collected to obtain 27 mg of a crude product (ii) of demethylmaytansinol 3-(N-phenyl)carbamate. This product (ii) was further purified as in Example 20. By the above procedure there was obtained 12 mg of demethylmaytansinol 3-(N-phenyl)carbamate as a white powder.

UV spectrum ($\lambda_{max}^{MeOH}$) nm: 233, 252, 280, 288.
Mass spectrum (m/e): 608, 471, 456, 436.

EXAMPLE 23

To 2 l of a culture broth of *Bacillus megaterium* IFO 12108 obtained as in Example 19 was added 37 mg of dechloromaytansinol 3-phenylacetate and the reaction was carried out under shaking at 28° C. for 48 hours. As assayed by TLC, dechloromaytansinol 3-phenylacetate had disappeared and, instead, demethyldechloromaytansinol 3-phenylacetate had been formed in the culture broth.

EXAMPLE 24

The culture broth obtained in Example 23 was purified as in Example 20 and TLC was performed thereon as in Example 20. The fractions absorbing at Rf≈0.43 were collected to obtain 30 mg of a crude product (ii) of demethyldechloromaytansinol 3-phenylacetate. This crude product (ii) was further purified as in Example 20. By the above procedure there was obtained 14 mg of demethyldechloromaytansinol 3-phenylacetate as a white powder.

UV spectrum ($\lambda_{max}^{MeOH}$) nm: 230, 240, 249, 277, 285.
Mass spectrum (m/e): 634 (M+), 573, 437, 422.

EXAMPLE 25

To 1 of a culture broth of *Bacillus megaterium* IFO 12108 as obtained in Example 19 was added 18 mg of maytansinol 3-hexanoate and the reaction was conducted under shaking at 30° C. for 48 hours. As determined by TLC, the maytansinol 3-hexanoate had completely disappeared and, instead, demethylmaytansinol 3-hexanoate had been produced in the culture broth.

EXAMPLE 26

The culture broth obtained in Example 25 was purified as in Example 20 and TLC was carried out thereon as in Example 20. The fractions at Rf≈0.48 were collected to obtain 9 mg of a crude product (ii) of demethylmaytansinol 3-hexanoate. Thereafter, this product was further purified as in Example 20. By the above procedure there was obtained 4 mg of demethylmaytansinol 3-hexanoate as a white powder.

UV spectrum ($\lambda_{max}^{MeOH}$) nm: 233, 240, 252, 280, 289.
Mass spectrum (m/e): 257, 471, 456, 436.

EXAMPLE 27

To 1 l of a culture broth of *Bacillus megaterium* IFO 12108 as obtained in Example 19 was added 19.5 mg of maytansinol 3-p-chlorobenzoate and the reaction was carried out under shaking at 30° C. for 27 hours. As assayed by TLC, the maytansinol 3-p-chlorobenzoate had completely disappeared, demethylmaytansinol 3-p-chlorobenzoate had been produced in the culture broth.

EXAMPLE 28

The culture broth obtained in Example 27 was purified as in Example 20 and TLC was carried out thereon as in Example 20. The fractions at Rf≈0.43 were collected to obtain 12 mg of a crude product (ii) of demethylmaytansinol 3-p-chlorobenzoate. This crude product was further purified as in Example 20. By the above procedure there was obtained 6 mg of demethylmaytansinol 3-p-chlorobenzoate as a white powder.

UV spectrum ($\lambda_{max}^{MeOH}$) nm: 240, 252, 280, 289.
Mass spectrum (m/e): 627, 471, 456, 436.

EXAMPLE 29

*Streptomyces flavotricini* IFO 12770 was cultivated as in Example 9 and 15.9 mg of maytansinol 3-cyclohexanecarboxylate was added to 750 ml of the culture. The reaction was conducted under shaking at 28° C. for 48 hours. As assayed by TLC, the maytansinol 3-cyclohexanecarboxylate had completely disappeared and, instead, demethylmaytansinol 3-cyclohexanecarboxylate had been formed in the culture broth.

EXAMPLE 30

The culture broth obtained in Example 29 was purified as in Example 20 and TLC was carried out therein as in Example 20. The fractions at Rf≈0.45 were collected to obtain 9 mg of crude product (ii) of demethylmaytansinol 3-cyclohexanecarboxylate. This product was further purified as in Example 20. By the above procedure there was obtained 4 mg of demethylmaytansinol 3-cyclohexanecarboxylate as a white powder.

UV spectrum ($\lambda_{max}^{MeOH}$) nm: 233, 240, 252, 280, 289.
Mass spectrum (m/e): 599, 471, 456, 436.

EXAMPLE 31

*Streptomyces platensis* IFO 12901 was cultivated as in Example 9 and 40 mg of maytansinol 3-phenylacetate was added to 4 l of the culture. The reaction was carried out under shaking at 28° C. for 48 hours. As determined by TLC, the maytansinol 3-phenylacetate had decreased and instead, demethylmaytansinol 3-phenylacetate had been produced in the broth.

EXAMPLE 32

The culture broth obtained in Example 31 was purified as in Example 20 and TLC was performed thereon as in Example 20. The fractions at Rf≈0.43 were collected to obtain 22 mg of crude demethylmaytansinol 3-phenylacetate (ii). This crude product was further purified as in Example 20. By the above procedure there was obtained 8 mg of demethylmaytansinol 3-phenylacetate as a white powder.

UV spectrum ($\lambda_{max}^{MeOH}$) nm: 233, 240, 252, 280, 289
Mass spectrum (m/e): 607, 471, 456, 436

EXAMPLE 33

*Bacillus megaterium* IFO 12108 was cultivated as in Example 19 and 140 mg of dechloromaytansinol 3-isobutyrate was added to 2.8 l of the resultant culture. The reaction was conducted under shaking at 28° C. for 50 hours. As assayed by TLC, the dechloromaytansinol 3-isobutyrate had disappeared and, instead, demethyldechloromethylansinol 3-isobutyrate had been formed in the broth.

EXAMPLE 34

The broth obtained in Example 33 was purified as in Example 20 and TLC was carried out thereon as in Example 20. The fractions at Rf≈0.42 were collected to obtain 113 mg of crude demethyldechloromaytansinol 3-isobutyrate (ii). This crude product (ii) was washed with a small amount of diethyl ether, dissolved in ethyl acetate and allowed to stand. By the above procedure there was obtained 76 mg crystals of demethyldechloromaytansinol 3-isobutyrate.

m.p. 213°–215° C.
Specific rotation: −116.6°(c=0.47, CHCl$_3$).
Elemental analysis (%): Found: C, 63.27; H, 7.33; N, 4.61; Calcd. for C$_{31}$H$_{42}$N$_2$O$_9$: C, 63.46; H, 7.22; N, 4.78.
UV spectrum ($\lambda_{max}^{MeOH}$) nm (ε): 230(27200), 240(29700), 248(29700), 277(4100), 285(3700).
Mass spectrum (m/e): 525, 437, 422.

EXAMPLE 35

*Streptomyces platensis* IFO 12901 was cultivated as in Example 9 and 440 mg of L-maytansine was added to 4.4 l of the culture. The reaction was carried out under shaking at 28° C. for 48 hours. As assayed by TLC, the maytansine had completely disappeared and, instead, L-demethylmaytansine had been formed in the broth.

EXAMPLE 36

To 4.4 l of the broth obtained in Example 35 was added 2.2 l of ethyl acetate and the resultant extract was suction-filtered through a strainer with 40 g of Hyflo Super Cel (Johns Manville Products Co., U.S.A.). This procedure was repeated for a second time. The extracts were combined, washed with 1.2 l of 1/200 N-hydrochloric acid and 1 l of 0.5% aqueous sodium hydrogen carbonate in that order, dried with 20 g. of anhydrous sodium sulfate and concentrated under reduced pressure to 2 ml. To the residue was added 50 ml of petroleum ether and the resulting precipitate was recovered by filtration (252 mg.). This crude L-demethylmaytansine (i) was dissolved in a small amount of chloroform and run onto a column (1.2 cm dia.) of 10 g. silica gel (Merck, Germany, 0.05–0.2 mm), elution being carried out with 100 ml of chloroform, 200 ml of chloroform/methanol (20:1) and 200 ml of chloroform/methanol (10:1). The eluate was collected in 2 ml fractions and each fractions was applied to a silica gel-glass plate (Merck, Germany, Kieselgel 60 F$_{254}$, 0.25 mm, 20×20) at a distance of 2.5 cm from its bottom edge. The chromatogram was developed over a distance of about 17 cm with ethyl acetate/methanol (19:1) and the UV absorbing zone (2537 A) was detected. Fractions No. 13 through No. 17 which absorbed at Rf≈0.23 were collected and concentrated under reduced pressure to about 1 ml. To the concentrate was added 30 ml of petroleum ether. By the above procedure there was obtained 183 mg of crude L-demethylmaytansine (ii).

EXAMPLE 37

In a small amount of chloroform was dissolved 183 mg of the crude L-demethylmaytansine (ii) obtained in Example 36 and the solution was linearly applied to each of 6 silica gel-glass plate (Merck, Germany, Kieselgel F$_{254}$, 2 mm, 20×20) at a distance of 2.5 cm from its bottom edge. The chromatogram was developed with ethyl acetate/methanol (19:1) and the zone absorbing at Rf 0.23 was scraped up and extracted twice with ethyl acetate containing a small amount of water. The resulting ethyl acetate extract was washed with water, dried over anhydrous sodium sulfate and concentrated under reduced pressure. To the concentrate was added hexane and the mixture allowed to stand, whereby 147 mg crystals of L-demethylmaytansine were obtained.

EXAMPLE 38

*Streptomyces platensis* IFO 12901 was cultivated as in Example 9 and 260 mg of D-maytansine was added to 2.6 l of the culture. The mixture was incubated at 28° C. and under shaking for 31 hours. As assayed by TLC, the D-maytansine had disappeared and, instead, D-demethylmaytansine had been formed in the broth.

EXAMPLE 39

The broth obtained in Example 38 was purified as in Example 36 and TLC was carried out thereon as in Example 36. The fractions absorbing at Rf≈0.08 were collected to obtain 166 mg of crude D-demethylmaytansine. This crude product was further purified as in Example 37. By the above procedure there was obtained 63 mg of D-demethylmaytansine as a white powder.

EXAMPLE 40

*Actiomyces nigrescens* IFO 12894 was cultivated as in Example 9 and 217 mg of maytanprine (DL) was added to 2.2 l of the culture. The mixture was incubated at 28° C. and under shaking for 48 hours. As assayed by TLC, the maytanprine (D,L) had disappeared and, instead, demethylmaytanprine (D,L) had been formed in the broth.

EXAMPLE 41

The broth obtained in Example 40 was purified as in Example 36 to obtain 153 mg of crude demethylmaytanprine (D,L). Thereafter, as in Example 37, the above product was linearly applied to each of 5 silica gel-glass plates at a distance of 2.5 cm from its bottom edge. The chromatogram was similarly developed with ethyl acetate/methanol (19:1) and the zones absorbing at Rf 0.40 and Rf 0.28 were each scraped up and extracted twice with ethyl acetate containing a small amount of water. The extracts were respectively washed with water, dried over anhydrous sodium sulfate, concentrated under reduced pressure and treated with petroleum ether. In the above manner, 47 mg of L-demethylmaytanprine was obtained as a white powder from the fraction absorbing at Rf 0.40 and 38 mg of D-demethylmaytanprine was obtained as a white powder from the fraction absorbing at Rf 0.28.

EXAMPLE 42

*Actinomyces nigrescens* IFO 12894 was cultivated as in Example 9 and 315 mg of maytanbutine (D, L) was added to 3.5 l of the culture. The mixture was reacted at 28° C. and under shaking for 48 hours. As assayed by TLC, the maytanbutine (D,L) had disappeared and, instead, demethylmaytanbutine had been formed in the broth.

EXAMPLE 43

The broth obtained in Example 42 was purified as in Example 36 to obtain 189 mg of crude demethylmaytanbutine (D,L.). Then, preparative TLC was carried out on this crude product and the chromatogram was developed with ethyl acetate/methanol (19:1). The zones absorbing at Rf 0.47 and Rf 0.31 were respectively scraped up and treated as in Example 37. By the above procedure, 85 mg of L-demethylmaytanbutine was obtained as white powder from the fraction absorbing at Rf 0.47 and 78 mg of D-demethylmaytanbutine was obtained as white powder from the zone absorbing at Rf 0.31.

EXAMPLE 44

*Actinomyces nigrescens* IFO 12894 was cultivated as in Example 9 and 530 mg of maytanvaline (D,L) was added to 5.3 l of the culture. The mixture was incubated at 28° C. and under shaking for 48 hours. As assayed by TLC, the maytanvaline (D,L) had disappeared and, instead, demethylmaytanvaline had been produced in the broth.

EXAMPLE 45

The broth obtained in Example 44 was purified as in Example 36 to obtain 223 mg of crude demethylmaytanvaline (D,L). Then, preparative TLC was carried out by the same procedure as Example 37 and the chromatogram was developed with ethyl acetate-methanol. The zones absorbing at Rf 0.55 and Rf 0.40 were respectively scraped up and treated as in Example 37. In this manner, 95 mg of L-demethylmaytanvaline was obtained as white powder from the fraction absorbing at Rf 0.55 and 88 mg of L-demethylmaytanvaline was obtained as white powder from the fraction absorbing at Rf 0.40.

EXAMPLE 46

*Streptomyces flavotricini* IFO 12770 was cultivated as in Example 9 and 40 mg of L-maytansine was added to 4 l of the resultant culture. The mixture was incubated at 28° C. under shaking for 48 hours and the resultant broth was purified as in Examples 36 and 37. By the above procedure there was obtained 5 mg of L-demethylmaytansine as white powder.

EXAMPLE 47

*Streptomyces flavotricini* IFO 12770 was cultivated as in Example 9 and 40 mg of D-maytansine was added to 4 l of the culture broth. The mixture was incubated at 28° C. and under shaking for 48 hours, and, then, treated as in Examples 36 and 37. To the broth was added a small amount of ethyl acetate and the mixture allowed to stand. By the above procedure there were obtained 6 mg crystals of D-demethylmaytansine.

EXAMPLE 48

*Actinomyces nigrescens* IFO 12894 was cultivated as in Example 9 and 10 mg of L-maytansine was added to 1 l of the culture. The mixture was incubated at 28° C. and under shaking for 48 hours. As assayed by TLC, the L-maytansine had decreased and, instead, L-demethylmaytansine had been produced in the broth.

EXAMPLE 49

*Streptomyces libani* IFO 13452 was cultivated as in Example 9 and 10 mg of L-maytansine was added to 1 l of the culture. The mixture was reacted at 28° C. and under shaking for 48 hours. As assayed by TLC, the titer of L-maytansine had been reduced and, instead, L-demethylmaytansine had been formed in the broth.

The physico-chemical properties of the compounds obtained in the foregoing Examples are shown in the following table.

33 to 34 were conducted to obtain the following compounds. The table sets forth the starting compounds, product compounds and the Rf values of the product compounds [developer solvent: $CHCl_3$/MeOH 9:1; plate: silica gel glass plate (Merck, Germany 60 $F_{254}$, 0.25 mm thick)]

| Starting compound (II) | Product compound (III) | Rf value |
| --- | --- | --- |
| Maytansinol | Demethylmaytansinol | 0.30 |
| Maytanacine | Demethylmaytanacine | 0.38 |
| Maytansinol propionate | Demethylmaytansinol propionate | 0.40 |
| Ansamitocin P-3 | PDM-3 | 0.42 |
| Ansamitocin P-3' | PDM-3' | 0.43 |
| Ansamitocin P-4 | PDM-4 | 0.44 |
| Maytansinol 3-valerate | Demethylmaytansinol 3-valerate | 0.45 |
| Maytansinol 3-hexanoate | Demethylmaytansinol 3-hexanoate | 0.48 |
| Maytansinol 3-heptanoate | Demethylmaytansinol 3-heptanoate | 0.49 |
| Maytansinol 3-octanoate | Demethylmaytansinol 3-octanoate | 0.50 |
| Maytansinol 3-phenylacetate | Demethylmaytansinol 3-phenylacetate | 0.43 |

TABLE 5

| | Demethyl-maytansine (L) | Demethyl-maytansine (D) | Demethyl-maytanprine (L) | Demethyl-maytanprine (D) |
| --- | --- | --- | --- | --- |
| m.p. | 194–196° C. | | | |
| Specific rotation | $-117.9°\ (c = 0.56,\ EtOH)$ | | | |
| Mol. formula | $C_{33}H_{44}ClN_3O_{10}$ | $C_{33}H_{44}ClN_3O_{10}$ | $C_{34}H_{46}ClN_3O_{10}$ | $C_{34}H_{46}ClN_3O_{10}$ |
| Mass spectrum, m/e | 616, 471, 456, 436, 128 | 616, 471, 456, 436, 128 | 630, 471, 456, 436, 142 | 630, 471, 456, 436, 142 |
| $UV\lambda_{max}^{MeOH}$ nm | 288, 281, 252, 243, 232 | 288, 281, 252, 243, 232 | 288, 281, 252, 243, 232 | 288, 281, 252, 243, 232 |
| NMR Main peaks (methyl signals) | 0.82, 3H, s<br>1.29, 3H, d, J = 6<br>1.33, 3H, d, J = 7<br>1.66, 3H, s<br>2.14, 3H, s<br>2.89, 3H, s<br>3.23, 3H, s<br>3.39, 3H, s | 0.87, 3H, s<br>1.28, 3H, d, J = 6<br>1.52, 3H, d, J = 7<br>1.72, 3H, s<br>2.19, 3H, s<br>3.06, 3H, s<br>3.18, 3H, s<br>3.38, 3H, s | 0.83, 3H, s<br>1.13, 3H, t, J = 7<br>1.29, 3H, d, J = 6<br>1.33, 3H, d, J = 7<br>1.65, 3H, s<br>2.87, 3H, s<br>3.23, 3H, s<br>3.38, 3H, s | 0.89, 3H, s<br>1.16, 3H, d, J = 7<br>1.28, 3H, d, J = 6<br>1.52, 3H, d, J = 7<br>1.72, 3H, s<br>3.04, 3H, s<br>3.18, 3H, s<br>3.37, 3H, s |
| TLC $H_2O$-saturated ethyl-acetate | 0.12 | 0.04 | 0.21 | 0.15 |
| Ethyl acetate-methanol (19:1) | 0.23 | 0.08 | 0.40 | 0.28 |

| | Demethyl-maytanbutine (L) | Demethyl-maytanbutine (D) | Demethyl-maytanvaline (L) | Demethyl-maytanvaline (D) |
| --- | --- | --- | --- | --- |
| Mol. formula | $C_{35}H_{48}ClN_3O_{10}$ | $C_{35}H_{48}ClN_3O_{10}$ | $C_{36}H_{50}ClN_3O_{10}$ | $C_{36}H_{50}ClN_3O_{10}$ |
| Mass spectrum, m/e | 644, 471, 456, 436, 156 | 644, 471, 456, 436, 156 | 658, 471, 456, 436, 170 | 658, 471, 456, 436, 170 |
| $UV\lambda_{max}^{MeOH}$ nm | 288, 281, 252, 243, 232 | 288, 281, 252, 243, 232 | 288, 281, 252, 243, 232 | 288, 281, 252, 243, 232 |
| NMR Main peaks (methyl signals) | 0.83, 3H, s<br>1.12, 6H, d, J = 7<br>1.29, 3H, d, J = 6<br>1.33, 3H, d, J = 7<br>1.67, 3H, s<br>2.86, 3H, s<br>3.21, 3H, s<br>3.41, 3H, s | 0.89, 3H, s<br>1.18, 6H, d, J = 7<br>1.29, 3H, d, J = 6<br>1.52, 3H, d, J = 7<br>1.72, 3H, s<br>3.08, 3H, s<br>3.21, 3H, s<br>3.37, 3H, s | 0.82, 3H, s<br>0.94, 3H, d, J = 6<br>0.98, 3H, d, J = 6<br>1.29, 3H, d, J = 6<br>1.33, 3H, d, J = 7<br>1.67, 3H, s<br>2.89, 3H, s<br>3.22, 3H, s<br>3.39, 3H, s | 0.92, 3H, s<br>0.96, 3H, d, J = 6<br>0.99, 3H, d, J = 6<br>1.29, 3H, d, J = 6<br>1.52, 3H, d, J = 7<br>1.72, 3H, s<br>3.04, 3H, s<br>3.17, 3H, s<br>3.37, 3H, s |
| TLC $H_2O$-saturated ethyl acetate | 0.25 | 0.16 | 0.30 | 0.20 |
| Ethyl acetate-methanol (19:1) | 0.47 | 0.31 | 0.55 | 0.40 |

EXAMPLE 50

Using *Bacillus megaterium* IFO-12108, the procedures similar to those of Examples 1 to 8, 19 to 28 and

| Starting compound (II) | Product compound (III) | Rf value |
|---|---|---|
| Maytansinol 3-phenylpropionate | Demethylmaytansinol 3-phenylpropionate | 0.45 |
| Maytansinol 3-benzoate | Demethylmaytansinol 3-benzoate | 0.42 |
| Maytansinol 3-cyclohexanecarboxylate | Demethylmaytansinol 3-cyclohexanecarboxylate | 0.45 |
| Maytansinol 3-p-chlorobenzoate | Demethylmaytansinol 3-p-chlorobenzoate | 0.43 |
| Maytansinol 3-nicotinate | Demethylmaytansinol 3-nicotinate | 0.31 |
| Maytansinol 3-isonicotinate | Demethylmaytansinol 3-isonicotinate | 0.30 |
| Maytansinol 3-picolinate | Demethylmaytansinol 3-picolinate | 0.40 |
| Maytansinol 3-(2-furan)carboxylate | Demethylmaytansinol 3-(2-furan)carboxylate | 0.38 |
| Maytansinol 3-cyclopropanecarboxylate | Demethylmaytansinol 3-cyclopropanecarboxylate | 0.39 |
| Dechloromaytansinol | Demethyldechloromaytansinol | 0.28 |
| Dechloromaytansinol 3-isobutyrate | Demethyldechloromaytansinol 3-isobutyrate | 0.42 |
| Dechloromaytansinol 3-phenylacetate | Demethyldechloromaytansinol 3-phenylacetate | 0.43 |
| Dechloromaytansinol 3-nicotinate | Demethyldechloromaytansinol 3-nicotinate | 0.31 |
| Dechloromaytansinol 3-cyclohexanecarboxylate | Demethyldechloromaytansinol 3-cyclohexanecarboxylate | 0.45 |
| D-Maytanvaline | Demethyl-D-maytanvaline | 0.47 |
| Maytansinol 3-(N—methyl)carbamate | Demethylmaytansinol 3-(N—methyl)carbamate | 0.27 |
| Maytansinol 3-(N—butyl)carbamate | Demethylmaytansinol 3-(N—butyl)carbamate | 0.39 |
| Maytansinol 3-(N—phenyl)carbamate | Demethylmaytansinol 3-(N—phenyl)carbamate | 0.40 |
| Maytansinol 3-(N—cyclohexyl)carbamate | Demethylmaytansinol 3-(N—cyclohexyl)-carbamate | 0.39 |
| Maytansinol 3-(3-pyridyl)carbamate | Demethylmaytansinol 3-(3-pyridyl)carbamate | 0.22 |
| Maytansinol 3-isopropylcarbonate | Demethylmaytansinol 3-isopropylcarbonate | 0.43 |
| Dechloromaytansinol 3-benzylcarbonate | Demethyldechloromaytansinol 3-benzylcarbonate | 0.44 |
| Maytansinol 3-phenylcarbonate | Demethylmaytansinol 3-phenylcarbonate | 0.38 |

EXAMPLE 51

Using *Streptomyces flavotricini* IFO 12770, the procedures similar to those of Examples 9, 29, 30 and 46 were conducted to obtain the following compounds.

The table sets forth the starting compounds, product compounds and the Rf values of the product compounds [developer solvent: $CHCl_3/MeOH$ 9:1; plate: silica gel-glass plate (Merck, Germany 60 $F_{254}$, 0.25 mm thick)].

| Starting compound (II) | Product compound (III) | Rf value |
|---|---|---|
| Maytansinol | Demethylmaytansinol | 0.30 |
| Maytanacine | Demethylmaytanacine | 0.38 |
| Maytansinol propionate | Demethylmaytansinol propionate | 0.40 |
| Ansamitocin P-3 | PDM-3 | 0.42 |
| Ansamitocin P-3' | PDM-3' | 0.43 |
| Ansamitocin P-4 | PDM-4 | 0.44 |
| Maytansinol 3-valerate | Demethylmaytansinol 3-valerate | 0.45 |
| Maytansinol 3-hexanoate | Demethylmaytansinol 3-hexanoate | 0.48 |
| Maytansinol 3-heptanoate | Demethylmaytansinol 3-heptanoate | 0.49 |
| Maytansinol 3-octanoate | Demethylmaytansinol 3-octanoate | 0.50 |
| Maytansinol 3-phenylacetate | Demethylmaytansinol 3-phenylacetate | 0.43 |
| Maytansinol 3-phenylpropionate | Demethylmaytansinol phenylpropionate | 0.45 |
| Maytansinol 3-benzoate | Demethylmaytansinol 3-benzoate | 0.42 |
| Maytansinol 3-cyclohexanecarboxylate | Demethylmaytansinol 3-cyclohexanecarboxylate | 0.45 |
| Maytansinol 3-p-chlorobenzoate | Demethylmaytansinol 3-p-chlorobenzoate | 0.43 |
| Maytansinol 3-nicotinate | Demethylmaytansinol 3-nicotinate | 0.31 |
| Maytansinol 3-isonicotinate | Demethylmaytansinol 3-isonicotinate | 0.30 |
| Maytansinol 3-picolinate | Demethylmaytansinol 3-picolinate | 0.40 |
| Maytansinol 3-(2-furan)carboxylate | Demethylmaytansinol 3-(2-furan)carboxylate | 0.38 |
| Maytansinol 3-cyclopropanecarboxylate | Demethylmaytansinol 3-cyclopropanecarboxylate | 0.39 |
| Dechloromaytansinol 3-isobutylate | Demethyldechloromaytransinol 3-isobutylate | 0.42 |
| Dechloromaytansinol 3-phenylacetate | Demethyldechloromaytansinol 3-phenylacetate | 0.43 |
| Dechloromaytansinol 3-nicotinate | Demethyldechloromaytansinol 3-nicotinate | 0.31 |
| Dechloromaytansinol 3-cyclohexanecarboxylate | Demethyldechloromaytansinol 3-cyclohexanecarboxylate | 0.45 |
| Maytansinol 3-(N—acetyl-N—benzyl)alanine ester [m.p. 174–177° C. (decomp.)] | Demethylmaytansinol 3-(N—acetyl-N—benzyl)-alanine ester | 0.46 |
| Maytansinol 3-(N—acetyl-N—methyl)-L-leucine ester | Demethylmaytansinol 3-(N—acetyl-N—methyl)-L-leucine ester | 0.43 |
| Maytansinol 3-(N—acetyl-N—methyl)-phenylalanine ester [m.p. 189–193° C. (decomp.)] | Demethylmaytansinol 3-(N—acetyl-N—methyl)-phenylalanine ester | 0.45 |
| L-maytansine | Demethyl-L-maytansine | 0.39 |
| D-maytansine | Demethyl-D-maytansine | 0.39 |
| L-maytanprine | Demethyl-L-maytanpurine | 0.43 |
| D-maytanprine | Demethyl-D-maytanpurine | 0.44 |
| L-maytanbutine | Demethyl-L-maytanbutine | 0.44 |
| D-maytanbutine | Demethyl-D-maytanbutine | 0.46 |
| D-maytanvaline | Demethyl-D-maytanvaline | 0.47 |
| Dechloro-D-maytansine | Demethyldechloro-D-maytansine | 0.39 |
| Maytansinol 3-(N—methyl)carbamate | Demethylmaytansinol 3-(N—methyl)carbamate | 0.27 |
| Maytansinol 3-(N—butyl)carbamate | Demethylmaytansinol 3-(N—butyl)carbamate | 0.39 |
| Maytansinol 3-(N—phenyl)carbamate | Demethylmaytansinol 3-(N—phenyl)carbamate | 0.40 |
| Maytansinol 3-(N—cyclohexyl)carbamate | Demethylmaytansinol 3-(N—cyclohexyl)-carbamate | 0.39 |
| Maytansinol 3-(3-pyridyl)carbamate | Demethylmaytansinol 3-(3-pyridyl)carbamate | 0.22 |
| Maytansinol 3-isopropylcarbonate | Demethylmaytansinol 3-isopropylcarbonate | 0.43 |
| Dechloromaytansinol 3-benzylcarbonate | Demethyldechloromaytansinol 3-benzylcarbonate | 0.44 |

-continued

| Starting compound (II) | Product compound (III) | Rf value |
|---|---|---|
| Maytansinol 3-phenylcarbonate | Demethylmaytansinol 3-phenylcarbonate | 0.38 |

EXAMPLE 52

Using *Streptomyces platensis* IFO 12901, the procedures similar to those of Examples 12, 31, 32 and 35 through 39 were conducted to obtain the following compounds. The table sets forth the starting compounds, product compounds and the Rf values of the product compounds (developer solvent: $CHCl_3$/MeOH 9:1; plate: silica gel-glass plate (Merck, Germany 60 $F_{254}$, 0.25 mm thick)).

| Starting compound (II) | Product compound (III) | Rf value |
|---|---|---|
| Maytanacine | Demethylmaytanacine | 0.38 |
| Maytansinol propionate | Demethylmaytansinol propionate | 0.40 |
| Ansamitocin P-3 | PDM-3 | 0.42 |
| Ansamitocin P-3' | PDM-3' | 0.43 |
| Ansamitocin P-4 | PDM-4 | 0.44 |
| Maytansinol 3-valerate | Demethylmaytansinol 3-valerate | 0.45 |
| Maytansinol 3-hexanoate | Demethylmaytansinol 3-hexanoate | 0.48 |
| Maytansinol 3-heptanoate | Demethylmaytansinol 3-heptanoate | 0.49 |
| Maytansinol 3-octanoate | Demethylmaytansinol 3-octanoate | 0.50 |
| Maytansinol 3-phenylacetate | Demethylmaytansinol 3-phenylacetate | 0.43 |
| Maytansinol 3-phenylpropionate | Demethylmaytansinol 3-phenylpropionate | 0.45 |
| Maytansinol 3-benzoate | Demethylmaytansinol 3-benzoate | 0.42 |
| Maytansinol 3-cyclohexanecarboxylate | Demethylmaytansinol 3-cyclohexanecarboxylate | 0.45 |
| Maytansinol 3-p-chlorobenzoate | Demethylmaytansinol 3-p-chlorobenzoate | 0.43 |
| Maytansinol 3-nicotinate | Demethylmaytansinol 3-nicotinate | 0.31 |
| Maytansinol 3-isonicotinate | Demethylmaytansinol 3-isonicotinate | 0.30 |
| Maytansinol 3-picolinate | Demethylmaytansinol 3-picolinate | 0.40 |
| Maytansinol 3-cyclopropanecarboxylate | Demethylmaytansinol 3-cyclopropanecarboxylate | 0.39 |
| Dechloromaytansinol 3-isobutyrate | Demethyldechloromaytansinol 3-isobutyrate | 0.42 |
| Dechloromaytansinol 3-phenylacetate | Demethyldechloromaytansinol 3-phenylacetate | 0.43 |
| Dechloromaytansinol 3-nicotinate | Demethyldechloromaytansinol 3-nicotinate | 0.31 |
| Dechloromaytansinol 3-cyclohexanecarboxylate | Demethyldechloromaytansinol 3-cyclohexanecarboxylate | 0.45 |
| Maytansinol 3-(N—acetyl-N—benzyl)alanine ester [m.p. 174–177° C. (decomp.)] | Demethylmaytansinol 3-(N—acetyl-N—benzyl) alanine ester | 0.46 |
| Maytansinol 3-(N—acetyl-N—benzyl)alanine ester [m.p. 163–166° C. (decomp.)] | Demethylmaytansinol 3-(N—acetyl-N—benzyl) alanine ester | 0.45 |
| Maytansinol 3-(N—acetyl-N—methyl)-L-leucine ester | Demethylmaytansinol 3-(N—acetyl-N—methyl)-L-leucine ester | 0.43 |
| Maytansinol 3-(N—acetyl-N—methyl)phenylalanine ester [m.p. 189–193° C. (decomp.)] | Demethylmaytansinol 3-(N—acetyl-N—methyl) phenylalanine ester | 0.45 |
| Maytansinol 3-(N—acetyl-N—methyl)phenylalanine ester [m.p. 212–214° C. (decomp.)] | Demethylmaytansinol 3-(N—acetyl-N—methyl) phenylalanine ester | 0.42 |
| L-maytansine | Demethyl-L-maytansine | 0.39 |
| D-maytansine | Demethyl-D-maytansine | 0.39 |
| L-maytanprine | Demethyl-L-maytanprine | 0.43 |
| D-maytanprine | Demethyl-D-maytanprine | 0.44 |
| L-maytanbutine | Demethyl-L-maytanbutine | 0.44 |
| D-maytanbutine | Demethyl-D-maytanbutine | 0.46 |
| L-maytanvaline | Demethyl-L-maytanvaline | 0.45 |
| D-maytanvaline | Demethyl-D-maytanvaline | 0.47 |
| Dechloro-D-maytansine | Demethyldechloro-D-maytansine | 0.39 |
| Maytansinol 3-(N—butyl)carbamate | Demethylmaytansinol 3-(N—butyl)carbamate | 0.39 |
| Maytansinol 3-(N—phenyl)carbamate | Demethylmaytansinol 3-(N—phenyl)carbamate | 0.40 |
| Maytansinol 3-(N—cyclohexyl)carbamate | Demethylmaytansinol 3-(N—cyclohexyl)carbamate | 0.39 |
| Maytansinol 3-(3-pyridyl)carbamate | Demethylmaytansinol 3-(3-pyridyl)carbamate | 0.22 |
| Maytansinol 3-isopropylcarbonate | Demethylmaytansinol 3-isopropylcarbonate | 0.43 |

EXAMPLE 53

In 20 ml of tetrahydrofuran was dissolved 50 mg of crystals of demethyldechloromaytansinol 3-isobutyrate crystals obtained in Example 34. After the solution was cooled to −5° C., 50 mg of lithium aluminum hydride was added. The reaction mixture was treated as in Example 13 and preparative TLC on silica gel was carried out with ethyl acetate/methanol (19:1) over a distance of 17 cm and the zone absorbing at Rf≈0.20 to 0.25 was scraped up and extracted with ethyl acetate containing a small amount of water. The extract was washed with water, dried over anhydrous sodium sulfate and concentrated under reduced pressure. By the above procedure there was obtained 43 mg of demethyldechloromaytansinol as powdery residue. It was then dissolved in a small amount of ethyl acetate, the solution was allowed to stand and the resultant crystals were collected by filtration and dried. Yield 33 mg. m.p. 198°–201° C.(decomp.).

Elemental analysis (%): Found: C, 62.48; H, 7.25; N, 5.19; O 24.89; Calcd. for $C_{27}H_{36}N_2O_8$: C, 62.77; H, 7.02; N, 5.42; O, 24.77.

Mass spectrum (m/e): 455, 437.

UV spectrum $(\lambda_{max}^{MeOH})$nm: 230, 240, 248, 277, 285.

EXAMPLE 54

In 20 ml of tetrahydrofuran were dissolved 50 mg of crystals of L-demethylmaytansine obtained in Example 37. After the solution was cooled to −5° C., 50 mg of lithium aluminum hydride was added. The reaction mixture was put in a water bath and stirred for 30 minutes. After the addition of 10 ml ethyl acetate and 10 ml of 1/200 N-HCl, the mixture was extracted with 50 ml of ethyl acetate. The ethyl acetate layer was washed with water, dried by the addition of anhydrous sodium sulfate and concentrated under reduced pressure. Preparative TLC of the product was carried out on the residue with silica gel with ethyl acetate/methanol (19:1) over a distance of 17 cm. The zone absorbing at Rf=0.25 was scraped up and extracted with ethyl acetate containing a small amount of water. The extract was washed with water, dried over anhydrous sodium sulfate and concentrated under reduced pressure. By the above procedure there was obtained 41 mg of demethylmaytansinol.

The physico-chemical properties of this product were identical with those of the demethylmaytansinol obtained in Example 5. m.p.195° C.

Elemental analysis (%): Found: C, 58.67; H, 6.54; N, 4.83; Cl, 6.19; Calcd. for $C_{27}H_{35}ClN_2O_8$: C, 58.85; H, 6.40; N, 5.08; Cl, 6.43.

Mass spectrum (m/e): 489, 471.

UV spectrum (nm): 232, 242, 251, 280, 288.

EXAMPLE 55

In 14 ml of tetrahydrofuran was dissolved 35 mg of the D-demethylmaytansine in powder form obtained in Example 39. The solution was cooled to −5° C., and 35 mg of lithium aluminum hydride was added. The mixture was treated and the product purified as in Example 54 to give 19 mg of demethylmaytansinol as a white powder. The physico-chemical properties of this product were identical with those of the demethylmaytansinol obtained in Example 54. m.p.196° C.

EXAMPLE 56

In 14 ml of tetrahydrofuran was dissolved 30 mg of the demethylmaytansinol 3-(N-phenyl)carbamate powder obtained in Example 22. After the solution was cooled to −5° C. or below, 30 mg of lithium aluminum hydride was added. The similar treatment and purification procedure to those in Example 54 gave 17 mg of demethylmaytansinol as a white powder. The physico-chemical properties of this product were identical with those of the demethylmaytansinol obtained in Example 54. m.p.194° C.

EXAMPLE 57

*Streptomyces flavotricini* IFO 12770 was inoculated into a culture medium (pH 7.2) containing 1% dextrin, 1% glucose, 1% glycerol, 0.5% peptone, 0.5% yeast extract, 0.5% meat extract, 0.3% sodium chloride and 0.5% calcium carbonate and shake culture was carried out at 28° C. for 24 hours. To 5 l of the resultant culture was added 50 mg of maytansinol 3-phenylcarbonate and the reaction was carried out under shaking at 28° C. for 48 hours. As assayed by thin layer chromatography (TLC), maytansinol 3-phenylcarbonate had been produced in the reaction mixture.

The culture broth thus obtained was purified as in Example 2 and subjected to thin layer chromatography as in Example 2. The fractions at Rf=0.38 were collected to give a crude product (ii) of demethylmaytansinol 3-phenylcarbonate (24 mg). It was further purified as described in Example 3 to give white powder of demethylmaytansinol 3-phenylcarbonate (13 mg).

TLC Rf=0.38 (Silica gel, Merck; developing solvent: chloroform: methanol=9:1).

MS-spectrum (m/e) 609 (M+-61).

EXAMPLE 58

To 5 l of the culture broth of *Bacillus megaterium* IFO 12108 obtained as Example 1 was added 100 mg of dechloromaytansinol 3-benzylcarbonate and the reaction was carried out under shaking at 28° C. for 48 hours.

Five liters of the culture broth thus obtained was purified as in Example 2 and TLC was performed thereon as in Example 2. The fractions at Rf=0.44 were collected to give a crude product (ii) (63 mg). It was further purified as in Example 3 to give white powder of demethyldechloromaytansinol 3-benzylcarbonate (48 mg).

TLC Rf=0.44 (Silica gel, Merck; developing solvent: chloroform: methanol=9:1).

MS-spectrum (m/e) 589 (M+-61).

EXAMPLE 59

In 4 ml of tetrahydrofuran was dissolved 10 mg of powders of demethyldechloromaytansinol 3-benzylcarbonate obtained in Example 58. After the solution was cooled at −5° C., 10 mg of lithium aluminum hydride was added. The reaction mixture was stirred in an ice-bath for 30 minutes, and after the addition of 2 ml of ethyl acetate and 1.2 ml of 1/200 N-hydrochloric acid, the mixture was extracted with further addition of 10 ml of ethyl acetate. The ethyl acetate layer was washed with water, dried by addition of anhydrous sodium sulfate and concentrated under reduced pressure. The concentrate was subjected to preparative TLC on silica gel with ethyl acetate/methanol (19:1) as the solvent system. The zone absorbing at Rf=0.20 to 0.25 was scraped up and extracted with ethyl acetate containing a small amount of water. The extract was washed with water, dried over anhydrous sodium sulfate and concentrated under reduced pressure. By the above procedure there was obtained 6.2 mg of demethyldechloromaytansinol as powdery residue. It was then dissolved in a small amount of ethyl acetate, the solution was allowed to stand and the resultant crystals were collected by filtration and dried. Yield 4.8 mg. m.p. 198°–201° C. (decomp.).

Elemental analysis (%): Found: C, 62.68; H, 7.21; N, 5.16; O, 24.92; Calcd. for $C_{27}H_{36}N_2O_8$: C, 62.77; H, 7.02; N, 5.42; O, 24.77.

Mass spectrum (m/e): 455, 437.

UV spectrum ($\lambda_{max}^{MeOH}$)nm: 230, 240, 248, 277, 285.

EXAMPLE 60

To 5 l of culture broth of *Streptomyces platensis* IFO 12901 obtained as Example 9 was added 50 mg of maytansinol 3-isopropylcarbonate. The reaction was carried out under shaking at 28° C. for 48 hours.

As assayed by TLC, the maytansinol 3-isopropylcarbonate had completely disappeared and, instead, demethylmaytansinol 3-isopropylcarbonate had been formed in the culture broth.

The culture broth thus obtained was purified as in Example 2 and TLC was performed thereon as in Example 2. The fractions at Rf=0.43 were collected to give a crude product (ii) of demethylmaytansinol 3-isopropylcarbonate (18 mg), and it was further purified as in Example 3 to give white powder of demethylmaytansinol 3-isopropylcarbonate (14 mg).

TLC Rf=0.43 (Silica gel, Merck; developing solvent: chloroform: methanol=9:1).

MS-spectrum (m/e) 575 (M+-61).

EXAMPLE 61

In 4 ml of tetrahydrofuran was dissolved 10 mg of powders of demethylmaytansinol 3-isopropylcarbonate obtained in Example 60. After the solution was cooled to −5° C., 10 mg of lithium aluminium hydride was added. The reaction mixture was treated as in Example 59 and preparative TLC or silica gel was carried out with ethyl acetate/methanol (19:1) over a distance of 17 cm and the zone absorbing at Rf=0.25–0.32 was scraped up and extracted with ethyl acetate containing a small amount of water. The extract was washed with water, dried over anhydrous sodium sulfate and concentrated under reduced pressure. By the above procedure there was obtained 6.8 mg of demethylmaytansinol as white powder.

m.p. 196° C. (decomp.).

Elemental analysis (%): Found: C, 58.62; H, 6.54; N, 4.82; Cl, 6.21; Calcd. for $C_{27}H_{35}ClN_2O_8$: C, 58.85; H, 6.40; N, 5.08; Cl, 6.43.

Mass spectrum (m/e): 489, 471.

UV spectrum $(\lambda_{max}{}^{MeOH})$nm: 232, 242, 251, 280, 288.

What we claim is:

1. A method for producing a demethylmaytansinoid compound of the formula:

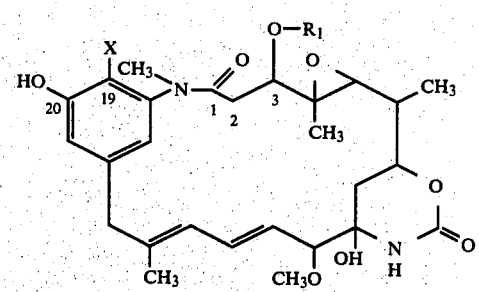

(wherein X is Cl or H; $R_1$ is H or acyl) characterized in that a maytansinoid compound of the formula:

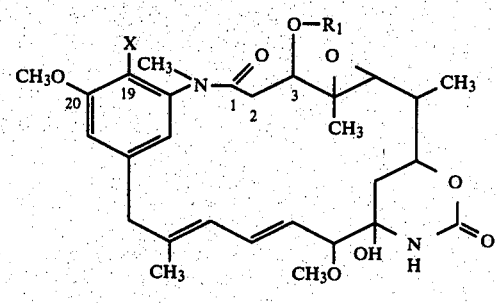

(wherein X and $R_1$ are as respectively defined above) is contacted with a culture broth, inclusive of a processed matter of the culture broth, of a microorganism belonging to the genus Bacillus, the genus Streptomyces or the genus Actinomyces which is able to transform the 20-methoxy group of said maytansinoid compound into a hydroxy group.

2. A method as claimed in claim 1, wherein the microorganism is *Bacillus megaterium*, *Streptomyces flavotricini*, *Streptomyces platensis*, *Streptomyces libani* or *Actinomyces nigrescens*.

3. A method as claimed in claim 2, wherein the microorganism is *Bacillus megaterium* IFO 12108 *Streptomyces flavotricini* IFO 12770, *Streptomyces platensis* IFO 12901, *Streptomyces libani* IFO 13452 or *Actinomyces nigrescens* IFO 12894.

4. A method for producing a demethylmaytansinoid compound of the formula:

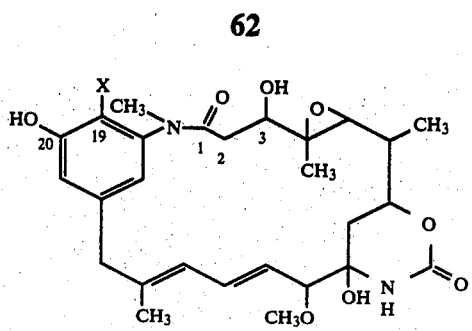

(wherein X is Cl or H) characterized in that a maytansinoid compound of the formula:

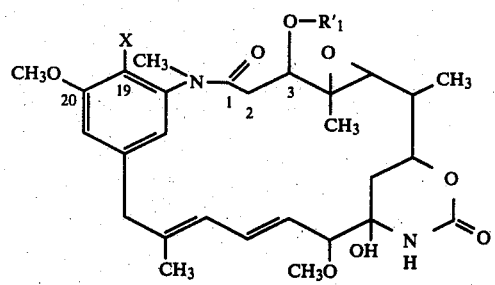

(wherein X is as defined above; $R_1'$ is acyl group) is contacted with a culture broth, inclusive of a processed matter of the culture broth, of a microorganism of the genus Bacillus, the genus Streptomyces or the genus Actinomyces which is able to transform the 20-methoxy group of said maytansinoid compound into a hydroxy group to obtain a compound of the formula:

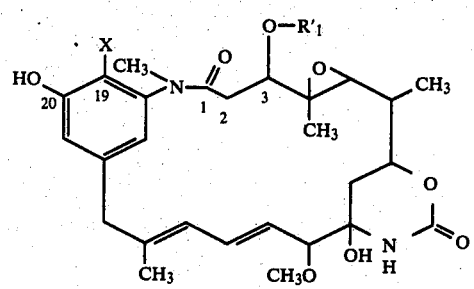

(wherein X and $R_1'$ are as respectively defined above) and this latter compound is then subjected to deacylation.

5. A method as claimed in claim 4, wherein the microorganism is *Bacillus megaterium*, *Streptomyces flavotricini*, *Streptomyces platensis*, *Streptomyces libani* or *Actinomyces nigrescens*.

6. A method as claimed in claim 5, wherein the microorganism is *Bacillus megaterium* IFO 12108, *Streptomyces flavotricini* IFO 12770, *Streptomyces platensis* IFO 12901, *Streptomyces libani* IFO 13452 or *Actinomyces nigrescens* IFO 12894.

7. A method as claimed in claim 4, wherein the deacylation is conducted by employing a complex metal hydride.

8. A method as claimed in claim 7, wherein the complex metal hydride is lithium aluminum hydride.

* * * * *